(12) United States Patent
Stein et al.

(10) Patent No.: US 9,492,238 B2
(45) Date of Patent: Nov. 15, 2016

(54) SYSTEM AND METHOD FOR MEASURING MUSCULAR-SKELETAL ALIGNMENT TO A MECHANICAL AXIS

(71) Applicant: Orthosensor Inc., Dania Beach, FL (US)

(72) Inventors: Marc Stein, Chandler, AZ (US); Martin Roche, Fort Lauderdale, FL (US)

(73) Assignee: ORTHOSENSOR INC, Dania Beach, FL (US)

( * ) Notice: Subject to any disclaimer, the term of this patent is extended or adjusted under 35 U.S.C. 154(b) by 252 days.

(21) Appl. No.: 14/026,605

(22) Filed: Sep. 13, 2013

(65) Prior Publication Data

US 2014/0276885 A1 Sep. 18, 2014

Related U.S. Application Data

(60) Provisional application No. 61/803,078, filed on Mar. 18, 2013.

(51) Int. Cl.
*A61F 2/46* (2006.01)
*A61B 5/103* (2006.01)
(Continued)

(52) U.S. Cl.
CPC ............ *A61B 34/20* (2016.02); *A61B 5/1036* (2013.01); *A61B 5/1072* (2013.01); *A61B 5/1121* (2013.01); *A61B 5/4528* (2013.01); *A61B 5/4571* (2013.01); *A61B 5/4585* (2013.01); *A61B 5/4851* (2013.01); *A61B 5/686* (2013.01); *A61B 17/154* (2013.01); *A61B 17/155* (2013.01); *A61B 17/157* (2013.01);
(Continued)

(58) Field of Classification Search
CPC ............ A61F 2/4657; A61F 2002/4658; A61F 2002/4668
See application file for complete search history.

(56) References Cited

U.S. PATENT DOCUMENTS 3,727,616 A    4/1973   Lenzkes
4,066,082 A    1/1978   Arcan et al.
(Continued)

FOREIGN PATENT DOCUMENTS

EP         1800097 B1    5/2008
WO     WO 0048507 A1 *  8/2000  ............. A61B 5/103
(Continued)

*Primary Examiner* — Nicholas Woodall

(57) ABSTRACT

A system and method is disclosed herein for measuring alignment of the muscular-skeletal system. The system comprises a sensored module that can be placed within a prosthetic component to measure load, position of load, and joint alignment. The system further includes a remote system for receiving, processing, and displaying quantitative measurements from the sensors. Alignment relative to a mechanical axis is measured. In a two bone system with a joint therebetween the total alignment measured comprises offsets measured for each bone. The joint is placed in a predetermined flexion that supports measurement of the joint as it is moved. The joint pivots on a point that is along the mechanical axis. Points along the arc made by the joint rotating between a first and second point are measured. An arc maximum is determined. The arc maximum is then converted to varus or valgus offset relative to the mechanical axis.

15 Claims, 60 Drawing Sheets

(51) Int. Cl.
*A61B 5/00* (2006.01)
*A61B 17/15* (2006.01)
*A61B 5/11* (2006.01)
*A61B 17/17* (2006.01)
*A61F 2/38* (2006.01)
*A61B 5/107* (2006.01)
*G06F 3/0481* (2013.01)

(52) U.S. Cl.
CPC ............ *A61B 17/1764* (2013.01); *A61B 34/10* (2016.02); *A61B 34/25* (2016.02); *A61B 90/37* (2016.02); *A61F 2/3836* (2013.01); *A61F 2/461* (2013.01); *A61F 2/4657* (2013.01); *A61F 2/4684* (2013.01); *G06F 3/0481* (2013.01); *A61B 5/4887* (2013.01); *A61B 2034/102* (2016.02); *A61B 2034/104* (2016.02); *A61B 2034/105* (2016.02); *A61F 2/38* (2013.01); *A61F 2002/4658* (2013.01); *A61F 2002/4668* (2013.01)

(56) References Cited

U.S. PATENT DOCUMENTS

| | | | |
|---|---|---|---|
| 4,092,597 A | 5/1978 | Place |
| 4,127,110 A | 11/1978 | Bullara |
| 4,277,758 A | 7/1981 | Mishiro |
| 4,480,485 A | 11/1984 | Bradshaw et al. |
| 4,731,762 A | 3/1988 | Hanks |
| 4,764,804 A | 8/1988 | Sahara et al. |
| 4,857,893 A | 8/1989 | Carrol |
| 4,899,761 A | 2/1990 | Brown et al. |
| 4,902,958 A | 2/1990 | Cook, II |
| 4,920,279 A | 4/1990 | Charlet et al. |
| 4,986,281 A | 1/1991 | Preves et al. |
| 5,042,489 A | 8/1991 | Weiner et al. |
| 5,119,676 A | 6/1992 | Bower et al. |
| 5,456,724 A | 10/1995 | Yen et al. |
| 5,470,354 A | 11/1995 | Hershberger et al. |
| 5,650,571 A | 7/1997 | Freud et al. |
| 5,733,292 A | 3/1998 | Gustilo et al. |
| 5,900,592 A | 5/1999 | Sohns et al. |
| 6,072,784 A | 6/2000 | Agrawal et al. |
| 6,165,142 A | 12/2000 | Bar |
| 6,385,475 B1 * | 5/2002 | Cinquin et al. ............... 600/407 |
| 6,425,920 B1 | 7/2002 | Hamada |
| 6,429,585 B1 | 8/2002 | Kitazume et al. |
| 6,443,891 B1 | 9/2002 | Grevious |
| 6,447,448 B1 | 9/2002 | Ishikawa et al. |
| 6,621,278 B2 | 9/2003 | Ariav |
| 6,739,068 B1 | 5/2004 | Rinner |
| 6,796,988 B2 | 9/2004 | Melkent et al. |
| 6,856,141 B2 | 2/2005 | Ariav |
| 6,993,393 B2 | 1/2006 | Von Arx et al. |
| 7,080,554 B2 | 7/2006 | Ariav et al. |
| 7,097,662 B2 | 8/2006 | Evans, III et al. |
| 7,153,281 B2 | 12/2006 | Holmes |
| 7,173,749 B2 | 2/2007 | Maleki et al. |
| 7,195,645 B2 | 3/2007 | Disilvestro et al. |
| 7,215,599 B2 | 5/2007 | Nishimori et al. |
| 7,283,867 B2 | 10/2007 | Strother et al. |
| 7,347,817 B2 | 3/2008 | Glukhovsky et al. |
| 7,378,916 B2 | 5/2008 | Oita et al. |
| 7,384,403 B2 | 6/2008 | Sherman |
| 7,396,336 B2 | 7/2008 | Orszulak et al. |
| 7,412,897 B2 | 8/2008 | Crottet et al. |
| 7,442,196 B2 | 10/2008 | Fisher et al. |
| 7,454,972 B2 | 11/2008 | Heyman et al. |
| 7,477,926 B2 | 1/2009 | McCombs |
| 7,481,780 B2 * | 1/2009 | De Guise et al. ............ 600/595 |
| 7,519,422 B2 | 4/2009 | Lippert et al. |
| 7,559,951 B2 | 7/2009 | DiSilvestro et al. |
| 7,575,602 B2 | 8/2009 | Amirouche et al. |
| 7,578,821 B2 | 8/2009 | Fisher et al. |
| 7,615,055 B2 | 11/2009 | DiSilvestro |
| 7,630,774 B2 | 12/2009 | Karni et al. |
| 7,632,283 B2 | 12/2009 | Heldreth |
| 7,668,201 B2 | 2/2010 | Sharony et al. |
| 7,725,288 B2 | 5/2010 | Boillot |
| 7,769,947 B2 | 8/2010 | Ranganathan et al. |
| 7,819,826 B2 | 10/2010 | Diederich et al. |
| 7,918,887 B2 | 4/2011 | Roche |
| 8,000,926 B2 | 8/2011 | Roche |
| 8,098,544 B2 | 1/2012 | Roche |
| 8,099,168 B2 | 1/2012 | Roche |
| 8,141,437 B2 | 3/2012 | Amirouche et al. |
| 8,167,823 B2 | 5/2012 | Nycz |
| 8,169,185 B2 | 5/2012 | Partovi et al. |
| 8,197,549 B2 | 6/2012 | Amirouche et al. |
| 8,211,041 B2 | 7/2012 | Fisher et al. |
| 8,270,253 B1 | 9/2012 | Roche |
| 8,295,920 B2 | 10/2012 | Bouton et al. |
| 8,372,147 B2 | 2/2013 | Roche |
| 8,372,153 B2 | 2/2013 | Roche |
| 8,421,642 B1 | 4/2013 | Roche |
| 8,444,654 B2 | 5/2013 | Roche |
| 8,449,556 B2 | 5/2013 | Roche |
| 8,494,805 B2 | 7/2013 | Roche |
| 8,498,711 B2 | 7/2013 | Roche |
| 2002/0049394 A1 | 4/2002 | Roy et al. |
| 2003/0004518 A1 | 1/2003 | Perren et al. |
| 2003/0036713 A1 | 2/2003 | Bouton et al. |
| 2003/0036764 A1 | 2/2003 | Hamada |
| 2003/0069644 A1 | 4/2003 | Kovacevic et al. |
| 2003/0114898 A1 | 6/2003 | Von Arx et al. |
| 2003/0153978 A1 * | 8/2003 | Whiteside .................. 623/20.21 |
| 2003/0187351 A1 | 10/2003 | Franck et al. |
| 2004/0011365 A1 | 1/2004 | Govari et al. |
| 2004/0064073 A1 | 4/2004 | Heldreth |
| 2004/0131013 A1 | 7/2004 | Ise et al. |
| 2004/0152970 A1 | 8/2004 | Hunter et al. |
| 2004/0184351 A1 | 9/2004 | Nishimori et al. |
| 2004/0215079 A1 | 10/2004 | Omura et al. |
| 2005/0010299 A1 | 1/2005 | Disilvestro |
| 2005/0010302 A1 | 1/2005 | Dietz et al. |
| 2005/0234555 A1 | 10/2005 | Sutton |
| 2005/0251148 A1 * | 11/2005 | Friedrich et al. ............... 606/88 |
| 2005/0252294 A1 | 11/2005 | Ariav |
| 2005/0267485 A1 | 12/2005 | Cordes et al. |
| 2005/0273170 A1 | 12/2005 | Navarro et al. |
| 2006/0069436 A1 | 3/2006 | Sutton et al. |
| 2006/0132120 A1 | 6/2006 | Luber et al. |
| 2006/0161051 A1 | 7/2006 | Terrill-Grisoni et al. |
| 2006/0206014 A1 | 9/2006 | Ariav |
| 2006/0241569 A1 | 10/2006 | DiSilvestro |
| 2007/0129776 A1 | 6/2007 | Robins et al. |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0242652 A1 | 10/2007 | Dahlman et al. |
| 2007/0258674 A1 | 11/2007 | Wang |
| 2008/0082118 A1 | 4/2008 | Edidin et al. |
| 2008/0129486 A1 | 6/2008 | Jeckelmann et al. |
| 2008/0133016 A1 | 6/2008 | Heinz |
| 2008/0191584 A1 | 8/2008 | Malkin |
| 2008/0228195 A1 | 9/2008 | Von Jako et al. |
| 2008/0228231 A1 | 9/2008 | Raphael et al. |
| 2009/0167719 A1 | 7/2009 | Woolley |
| 2010/0010494 A1 | 1/2010 | Quirno |
| 2010/0022874 A1 | 1/2010 | Wang et al. |
| 2010/0076505 A1 | 3/2010 | Borja |
| 2010/0100130 A1 | 4/2010 | Carl et al. |
| 2010/0151946 A1 | 6/2010 | Wilson et al. |
| 2010/0198067 A1 | 8/2010 | Mahfouz et al. |
| 2010/0204575 A1 | 8/2010 | Roche |
| 2010/0204955 A1 | 8/2010 | Roche |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0320973 A1 | 12/2010 | Nishida |
| 2010/0331633 A1 | 12/2010 | Stein |
| 2010/0331737 A1 | 12/2010 | Stein et al. |

(56) References Cited

U.S. PATENT DOCUMENTS

| | | |
|---|---|---|
| 2011/0029913 A1 | 2/2011 | Boillot |
| 2011/0032184 A1 | 2/2011 | Roche |
| 2011/0060220 A1 | 3/2011 | Roche |
| 2011/0092972 A1 | 4/2011 | Allen |
| 2011/0102455 A1 | 5/2011 | Temple |
| 2011/0160572 A1 | 6/2011 | McIntosh et al. |
| 2011/0160738 A1 | 6/2011 | McIntosh et al. |
| 2011/0257491 A1 | 10/2011 | Robertson et al. |
| 2012/0016362 A1 | 1/2012 | Heinrich et al. |
| 2012/0035868 A1 | 2/2012 | Roche |
| 2012/0209117 A1 | 8/2012 | Roche |
| 2013/0225982 A1 | 8/2013 | Roche |

FOREIGN PATENT DOCUMENTS

| | | |
|---|---|---|
| WO | 2006098759 A1 | 9/2006 |
| WO | 2008120215 A2 | 10/2008 |

\* cited by examiner

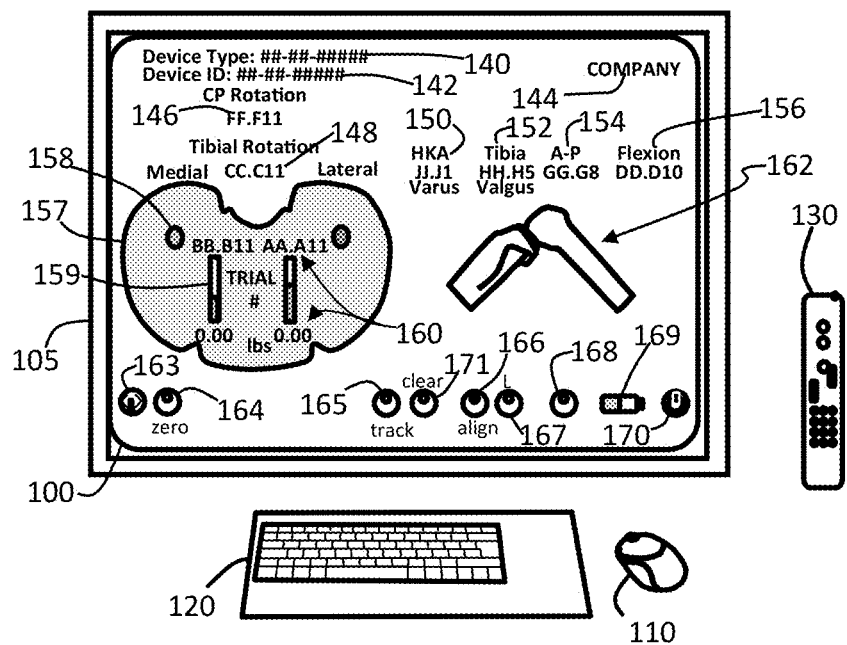
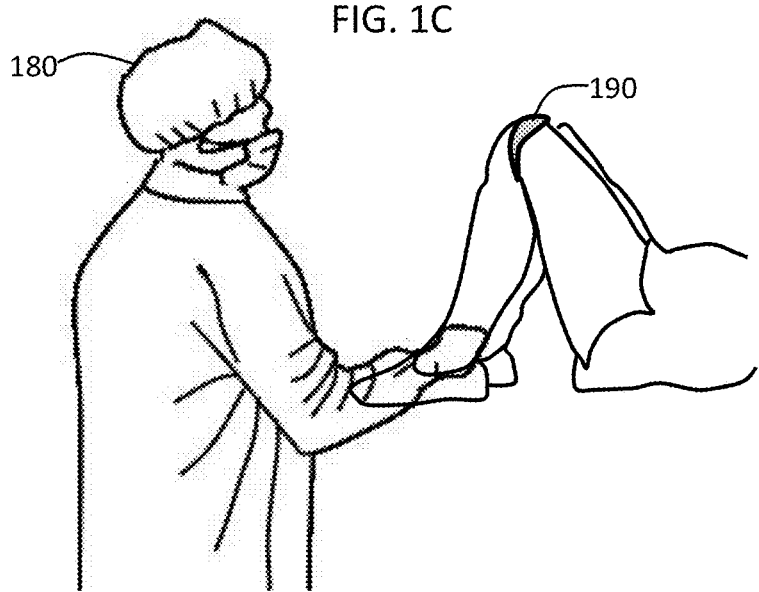
FIG. 1C

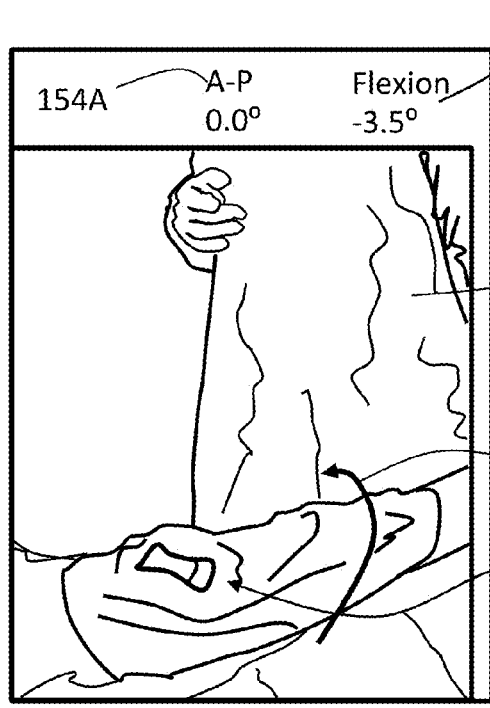
Fig. 7
Fig. 8
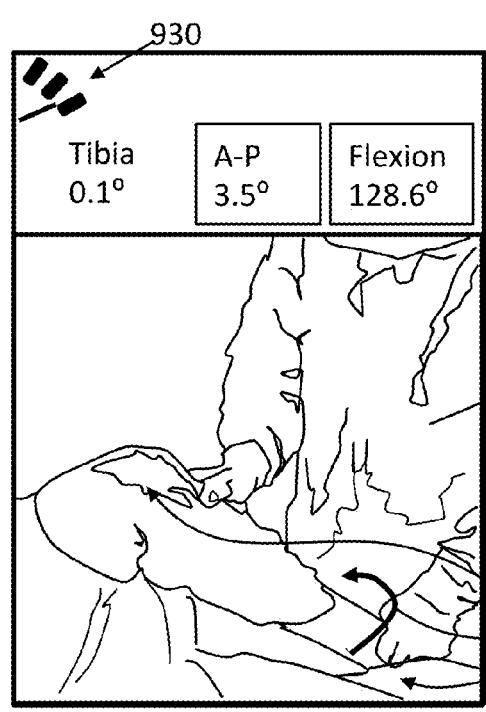
Fig. 9
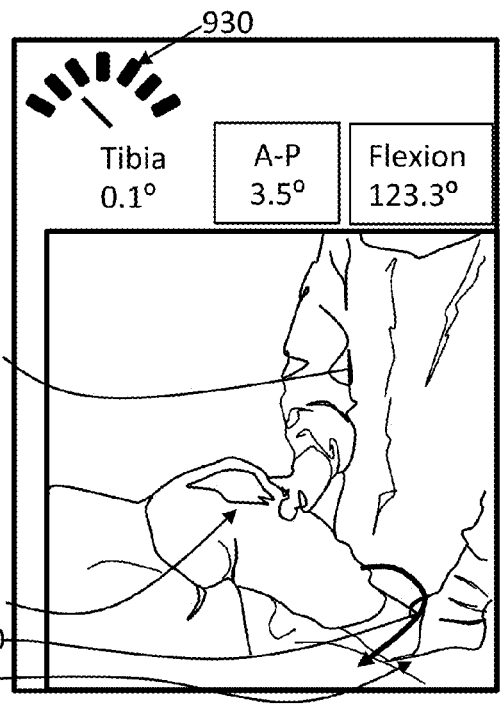
Fig. 10

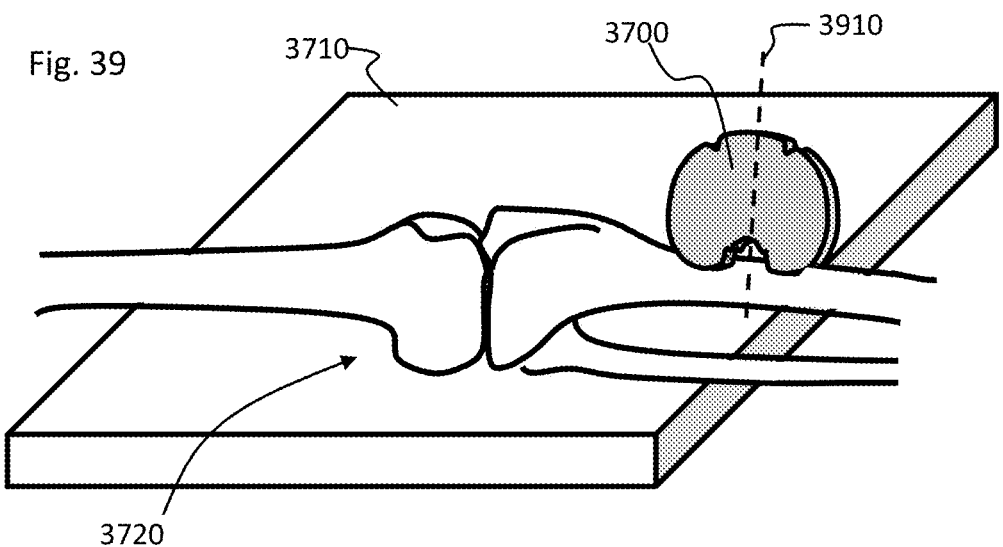
Fig. 39
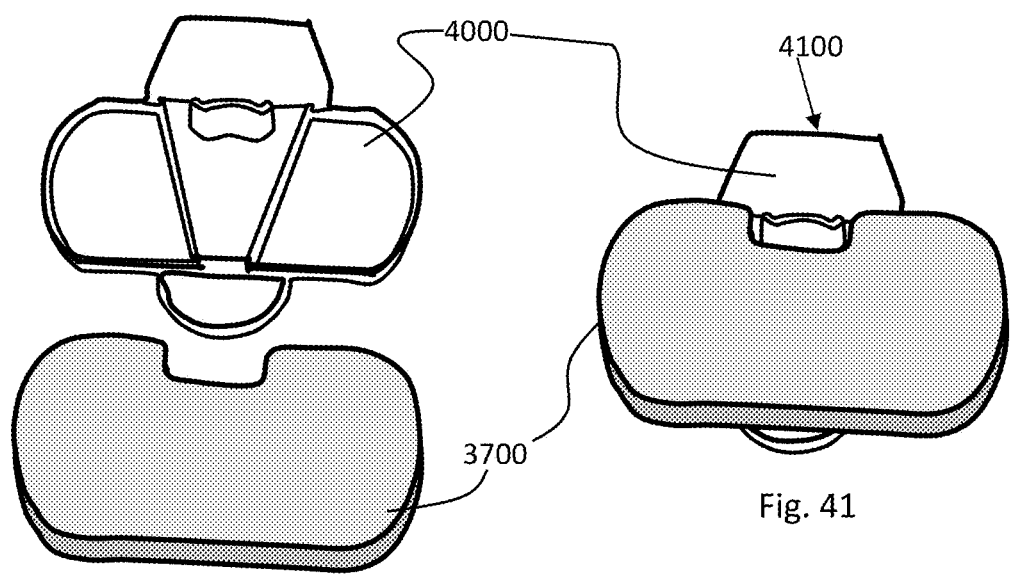
Fig. 40
Fig. 41

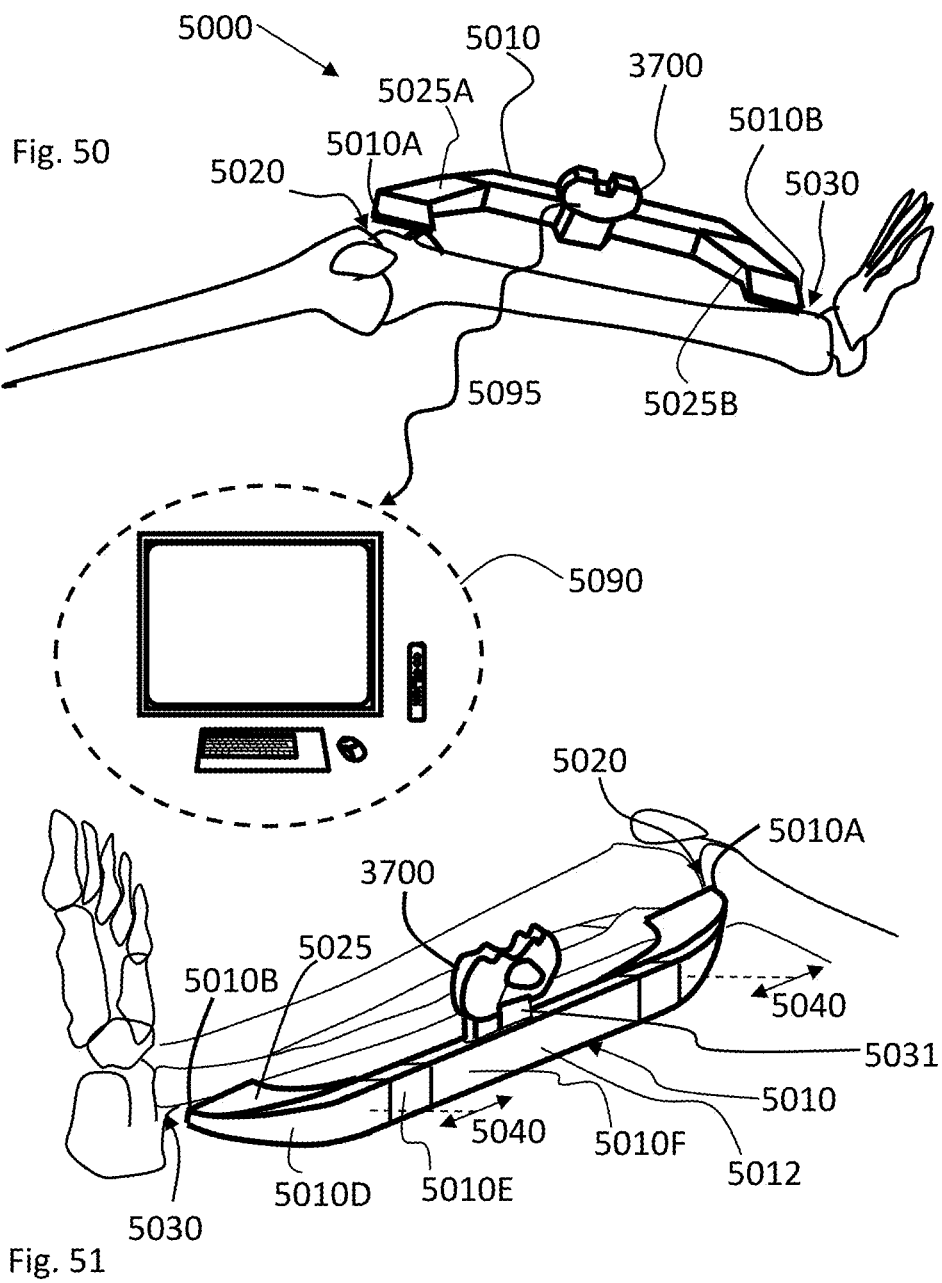

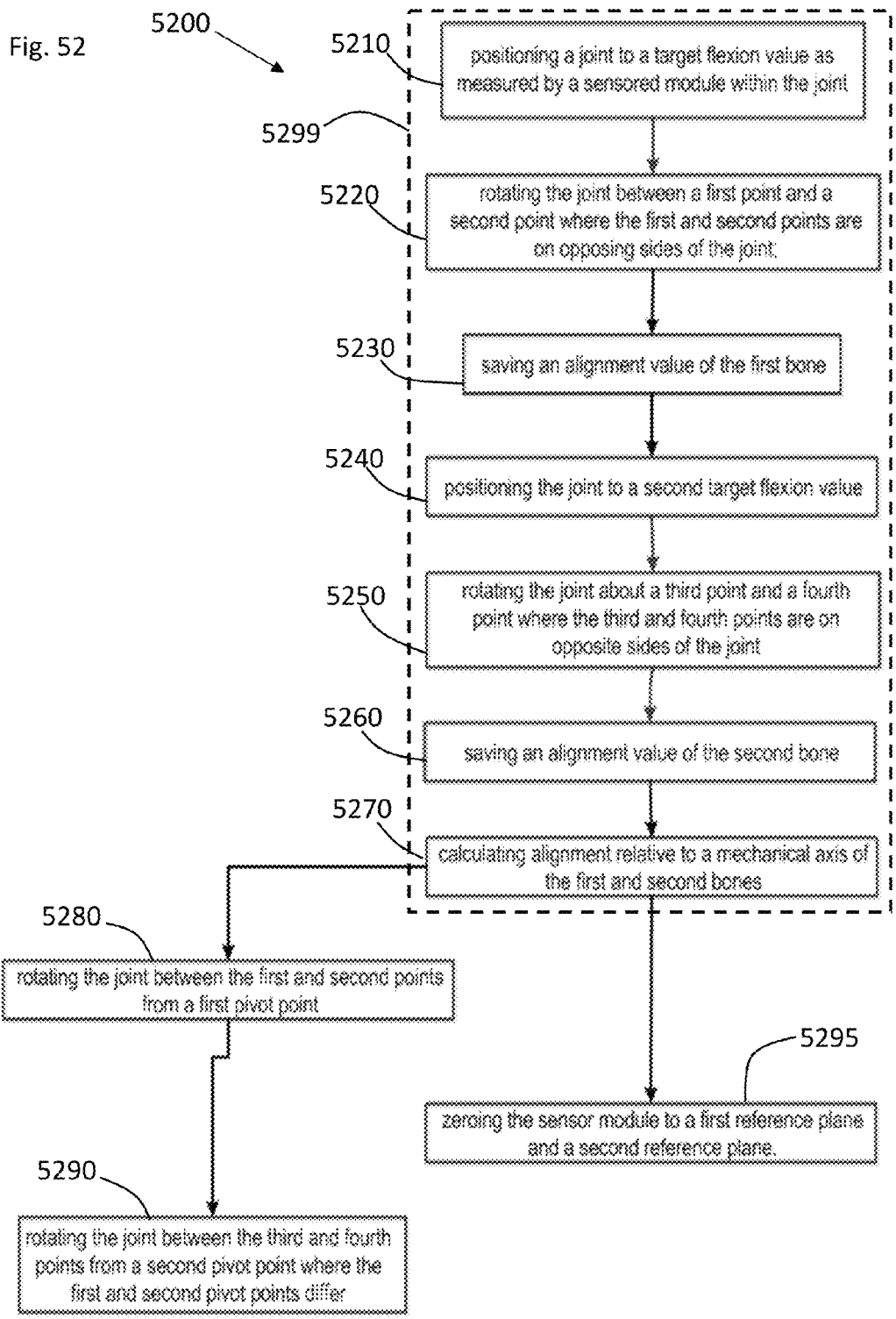

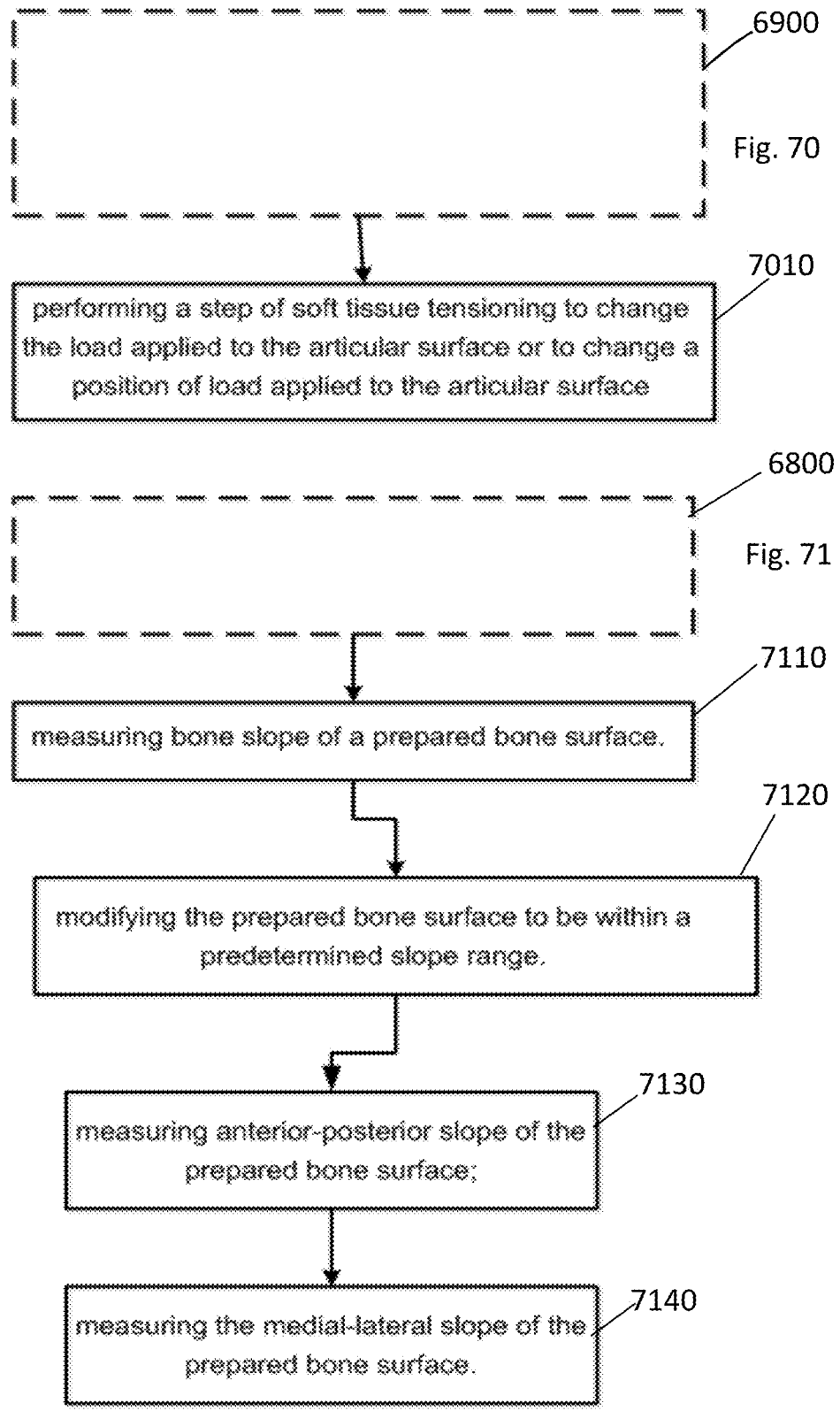

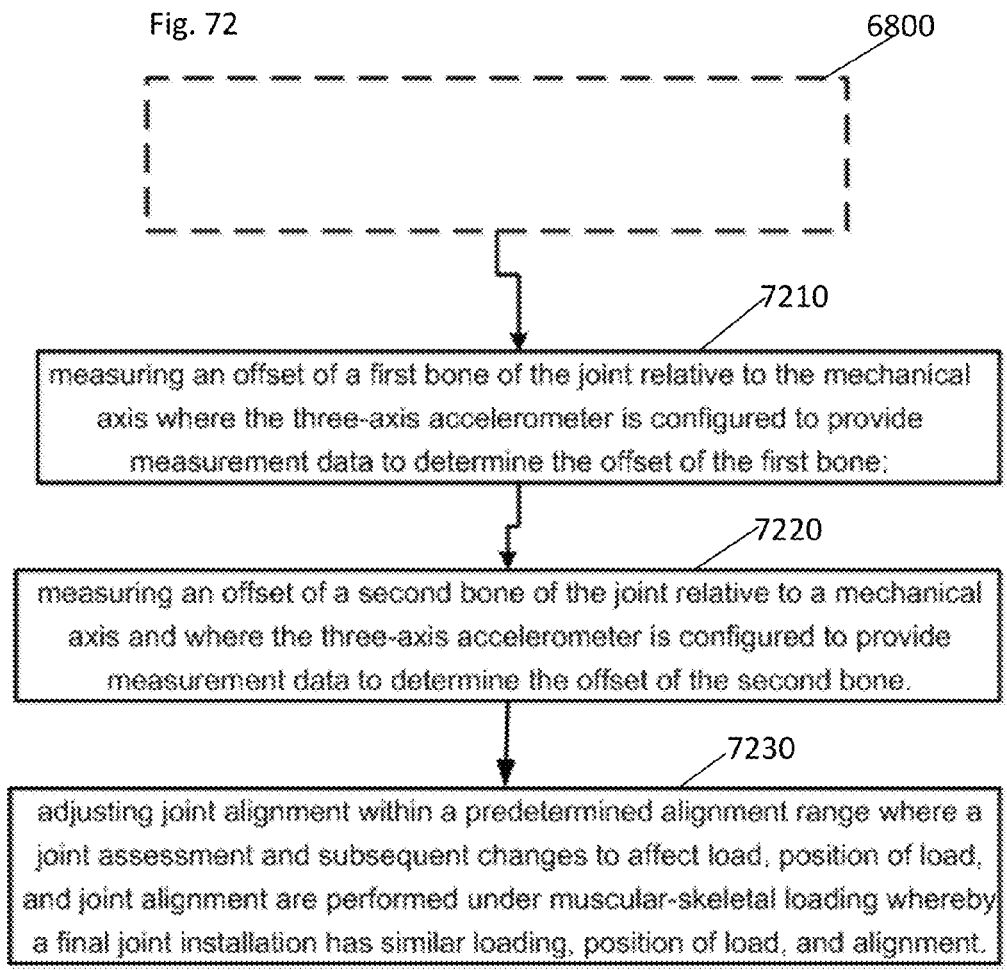

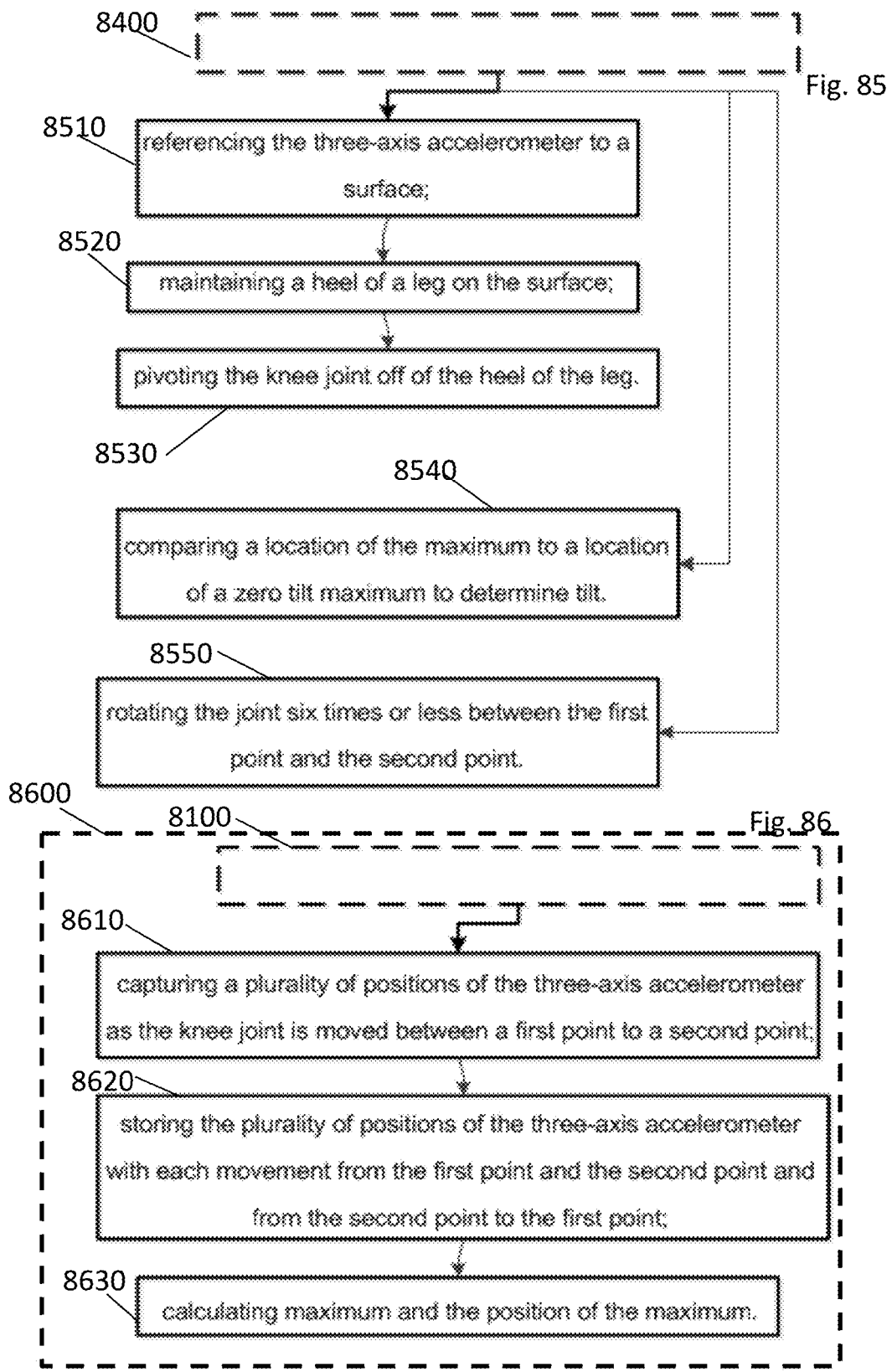

Output Acceleration vs. Angle of Inclination
for Single-Axis Inclination Sensing

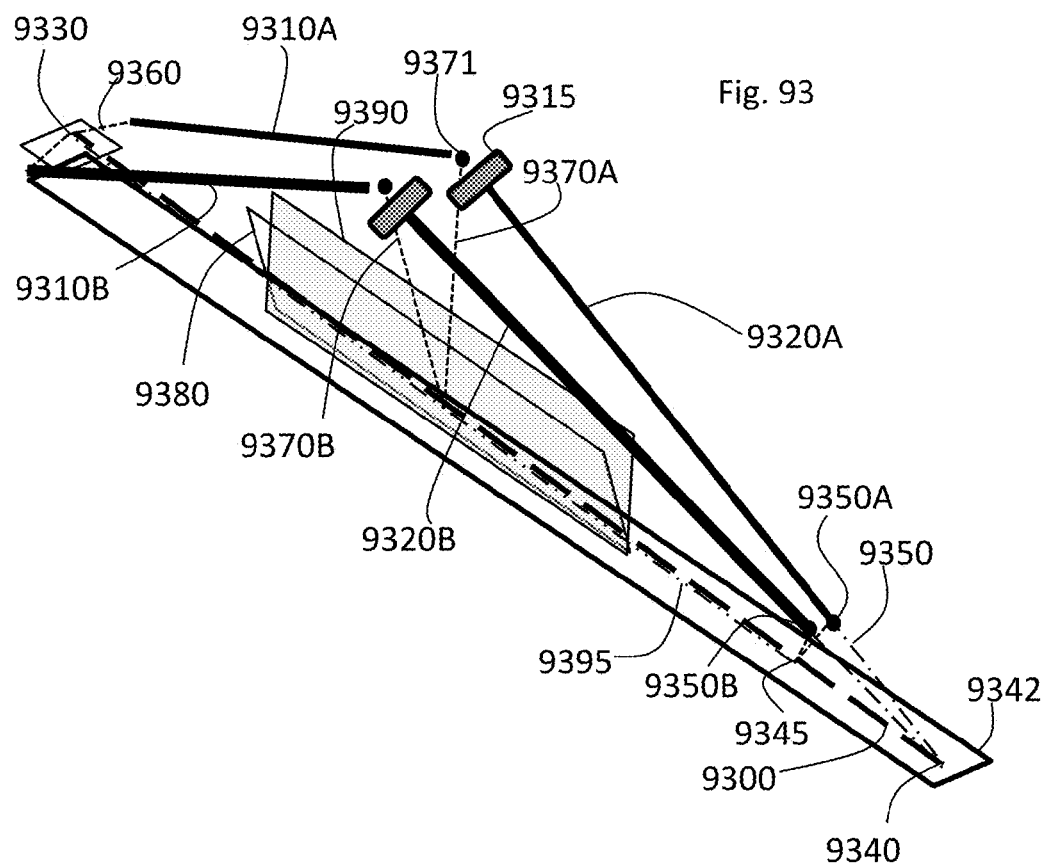

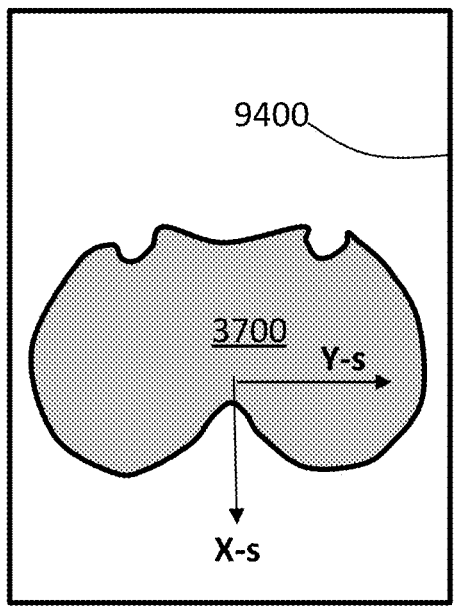
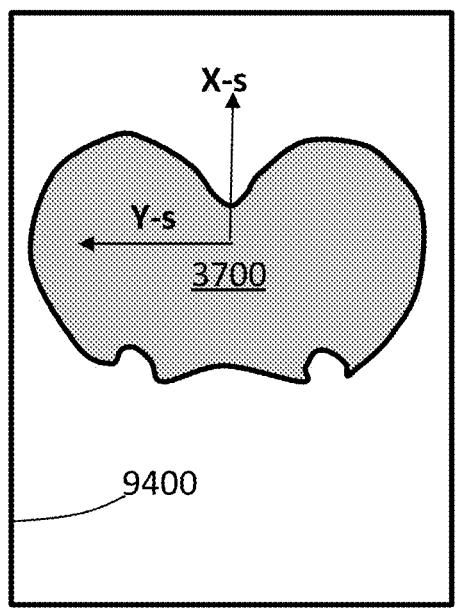
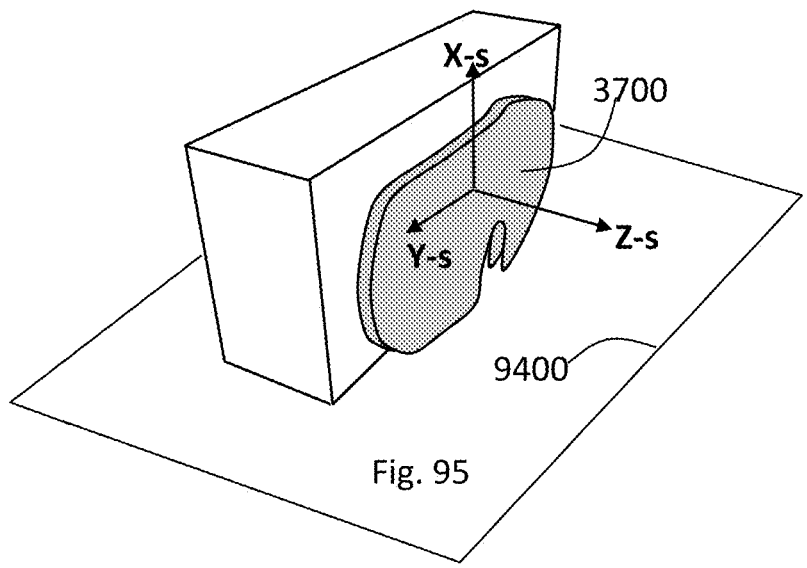

SYSTEM AND METHOD FOR MEASURING MUSCULAR-SKELETAL ALIGNMENT TO A MECHANICAL AXIS

CROSS-REFERENCE TO RELATED APPLICATIONS

This application claims the benefit of U.S. provisional patent application No. 61/803,078 filed 18 Mar. 2013. The disclosure of which is incorporated herein by reference in its entirety.

FIELD OF THE INVENTION

The invention relates in general to medical and surgical procedures and more particularly to aligning medical devices to precise locations on or within a patient's body.

BACKGROUND OF THE INVENTION

Orthopedic alignment currently involves cycles of trial and error. For example, leg alignment requires a technique that approximates alignment in which the surgeon makes one of the distal femoral cut and the proximal tibial cut based on experience, mechanical jigs, and visual alignment. Typically, the proximal tibial cut is made so as to remove the least amount of the proximal tibia, while ensuring sufficient removal of diseased or otherwise undesirable bone. The remaining femoral cuts are made to complete shaping of the femur to receive a femoral prosthesis. After the femoral and tibial cuts are complete, the femoral prosthesis and the tibial prosthesis, or trial versions thereof, are temporarily implanted and the surgeon reviews leg alignment. Typically, no adjustments are made if the leg is within a few degrees varus or valgus of the mechanical axis. An insert has a bearing surface that allows articulation of the leg. A set of shims can be coupled to the insert. The shims are used to change the thickness of the insert. A shim and insert combination is chosen that produces the best subjective movement characteristics of the joint through a full the range of motion. The surgeon may modify the bone or perform soft tissue tensioning to affect load, rotation or alignment characteristics. In general, the implant procedure is performed using the subjective skills of the surgeon to achieve appropriate leg alignment, rotation, balance, and soft tissue tension-loading.

Even with mechanical jigs, trialing, and advanced prosthetic components, outcomes including functional efficacy, patient comfort, and longevity of the prosthesis may not always be highly predictable, especially if procedures are performed by physicians and surgeons with different levels of skill, experience, and frequency of repeating an individual procedure. This may be confirmed by various reports in the literature that suggest a positive relationship between outcomes and the numbers of procedures performed annually by individual surgeons.

Accurately determining and aligning an implant orientation is a difficult process requiring expensive equipment. A simple, efficient method is needed to reduce medical costs and time of the surgical procedure, while maintaining accuracy.

BRIEF DESCRIPTION OF THE DRAWINGS

Embodiments of present invention will become more fully understood from the detailed description and the accompanying drawings, wherein:

FIG. 1C illustrates a simplified view of a physician using at least one embodiment of a motion and orientation sensing device (e.g., a surgical tracking system) with a computer display (e.g., a surgical tracking display system);

FIGS. 7 and 8 illustrates a user moving an orthopedic system in extension to obtain alignment data;

FIGS. 9 and 10 illustrates a user moving an orthopedic system in flexion to obtain alignment data;

FIG. 39 illustrates a device orientation to obtain reference axis data;

FIG. 40 illustrates an adapter and device that can be coupled to a cutting jig;

FIG. 41 illustrates the adapter and device coupled together;

FIG. 50 illustrates a tibia reference tool used for alignment;

FIG. 51 illustrates another view of the tibia reference tool used for alignment;

FIG. 52 illustrates a method of measuring joint alignment between first and second bones;

FIG. 70 illustrates another method of kinetic assessment, joint modification, and installation of a final prosthetic joint;

FIG. 71 illustrates another method of kinetic assessment, joint modification, and installation of a final prosthetic joint;

FIG. 72 illustrates another method of kinetic assessment, joint modification, and installation of a final prosthetic joint;

FIG. 85 illustrates another method of measuring medial-lateral tilt of a prepared bone surface of a knee joint;

FIG. 86 illustrates another method of measuring tilt of a prepared bone surface of a muscular-skeletal joint;

FIG. 93 illustrates a descriptive figure of a method in accordance with an embodiment;

FIGS. 94A and 94B illustrate horizontal orientations used in calibration in accordance with an embodiment; and FIG. 95 illustrates a vertical orientation used in calibration in accordance with an embodiment.

DETAILED DESCRIPTION OF EMBODIMENTS

Figure 1A:
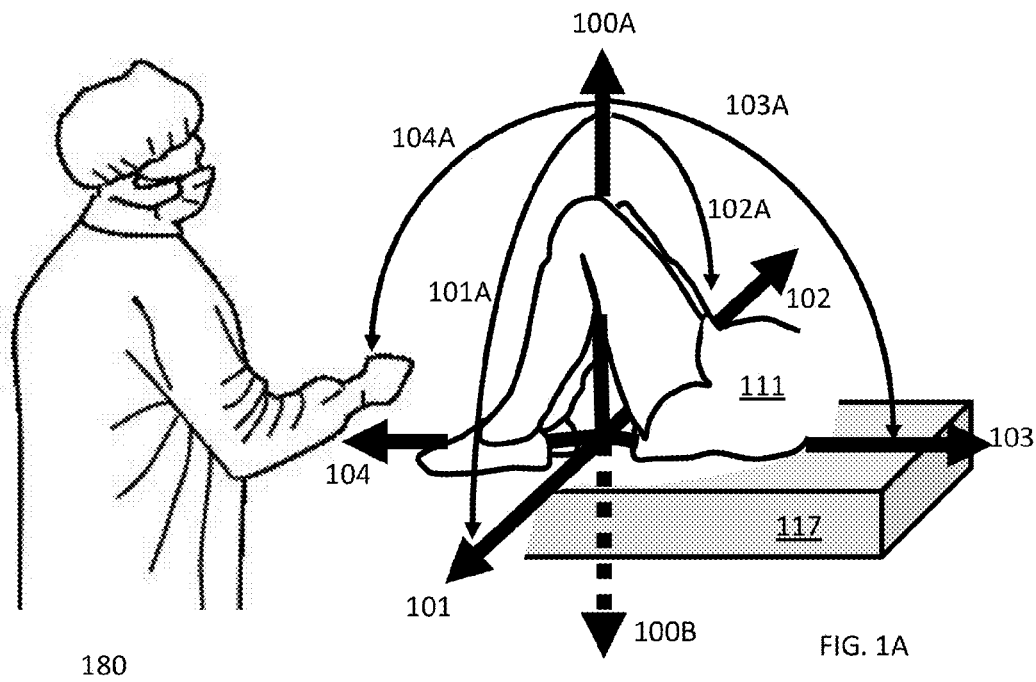
FIG. 1A illustrates a simplified view of directions of motion referred to herein.

The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

It will be appreciated by those skilled in the art that the words "during", "while", and "when" as used herein relating to circuit operation are not exact terms that mean an action takes place instantly upon an initiating action but that there may be some small but reasonable delay, such as a propagation delay, between the reaction that is initiated by the initial action. Additionally, the term "while" means that a certain action occurs at least within some portion of duration of the initiating action. The use of the word "approximately" or "substantially" means that a value of an element has a parameter that is expected to be close to a stated value or position. However, as is well known in the art there are always minor variances that prevent the values or positions from being exactly as stated.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate. For example specific methods of attaching a surgical device onto the surgical device holder, however one of ordinary skill would be able, without undo experimentation, to establish the steps using the enabling disclosure herein.

The terms precision and resolution can be used herein to specifically have the standard definitions. Precision will connate the variation from exactness. Resolution will have the customary definition of the smallest measurable interval. The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device.

The orientation of the x, y, z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

The terms 'motion sensing' and 'tilt sensing' and 'orientation' is also intended to have specific meaning. 'Motion sensing' indicates the detection of movement of a body that exceeds a specified threshold in one or more coordinate axes, for example the specific threshold in one or more Cartesian axes in terms of both static and dynamic acceleration. 'Heading' is defined as the orientation of longitudinal axis of the motion of the motion and orientation sensing module or device and movement in a direction. 'Tilt' is defined as the orientation of a body with respect to a zenith. The term slope is used interchangeable with the term "tilt." Tilt sensing' indicates the measurement of acceleration attributable to gravity in one or more axes. 'Orientation' includes yaw as well as 'tilt.' Note that although accelerometers are provided as enabling examples n the description of embodiments, any tracking device (e.g., a GPS chip, acoustical ranging, magnetometer, gyroscope, inclinometers, MEMs) can be used within the scope of the embodiments described.

Note that the term flexion value is used herein. For purposes of this disclosure a flexion value of approximately 180 degrees is full extension, and any value other than 180 degrees is a joint in flexion where the bones on either side of the joint intersect form an angle. Note also tolerance values are those known by one of ordinary skill in the arts, for example subjective tolerance on angle measurements can be 1 to 3 degrees.

At least one embodiment is directed to a kinetic orthopedic (e.g., knee) balancer system to aid a surgeon in determining real time alignment and loading of orthopedic implants. Although the system is generic to any orthopedic surgery (e.g., spinal, shoulder, knee, hip) the following examples deal with knee surgery as a non-limiting example of an embodiment of the invention.

The non-limiting embodiment described herein is related to quantitative measurement based orthopedic surgery and referred to herein as the kinetic system. The kinetic system includes a sensor system that provides quantitative data and feedback that is displayed visually and/or audibly and/or haptically to a surgeon. The kinetic system provides the surgeon real time dynamic data regarding loads in each compartment of the knee, tibio-femoral implant contact and congruency through a full range of motion, and information regarding angular bony cuts and leg alignment.

In general, kinetics is the study of the effect of forces upon the motion of a body or system of bodies. Disclosed herein is a system for kinetic assessment of the muscular-skeletal system. The kinetic system can be for the installation of prosthetic components or for monitoring and assessment of permanently installed components to the muscular-skeletal system. For example, installation of a prosthetic component can require one or more bone surface to be prepared to receive a device or component. The bone surfaces are cut to place the prosthetic component in a relational position to a mechanical axis of a joint. The kinetic system is designed to take quantitative measurements of at least the load, position of load, and alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

Measurements data supplement the subjective feedback of the surgeon to ensure optimal installation. The quantitative measurements can also be used to determine adjustments to bone, prosthetic components, or tissue prior to final installation or to fine tune the installation. Permanent sensors in the final prosthetic components can provide periodic data related to the status of the implant in use. Data collected intra-operatively and long term can be used to determine parameter ranges for surgical installation and to improve future prosthetic components. The physical parameter or parameters of interest can include, but are not limited to, measurement of load, force, pressure, position, displacement, density, viscosity, pH, spurious accelerations, and localized temperature. Often, several measured parameters or different measurements are used to make a quantitative assessment. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

FIG. 1A illustrates the basic directions and motions discussed herein with reference to a surgeon/user 180 and a patient 111. For example, the vertical axis 100A is perpendicular to the table 117 upon which the patient 111 lies. The vertical axis 100A points to the anterior direction. The axis 100B is parallel but opposite to the vertical axis 100A and points to the posterior direction. In the patient configuration shown corresponding to the left leg of patient 111 the axis 101 points to the lateral side of the knee while the axis 102 points to the medial side of the left knee. Thus, if a device is situated at the vertical axis 100A in the left knee and pivoted about the 103 and 104 axis in the 101 axis direction the device is being rotated in the lateral direction. Conversely, if the device is pivoted about the 103 and 104 axis in the 102 axis direction the device is being rotated in the medial direction. The knee joint move through an arc corresponding to axis 101A and axis 102A when rotated laterally and medially. In a first example of a pivot point the heel of the foot can be placed at a fixed position on the operating table along axis 104 to 103. The knee joint pivots off of heel of the leg but can be rotated along the axis 101A and the axis 102A. In a second example of a pivot point, the heel is lifted off of the operating table and the leg is pivoted off of the hip joint. The pivot point is the femoral head of the femur. Typically, the hip joint is at a fixed position on the operating table. The knee joint pivots off of the femoral head of the femur but can be rotated along the axis 101A and the axis 102A. The angle of the device in the knee joint can be changed by moving the pivot point of the heel in the direction 104 or the direction 103. For example, moving the heel in direction of the axis 104 will move the joint towards the posterior position 100B that correspondingly changes the angle of flexion.

Figure 1B:
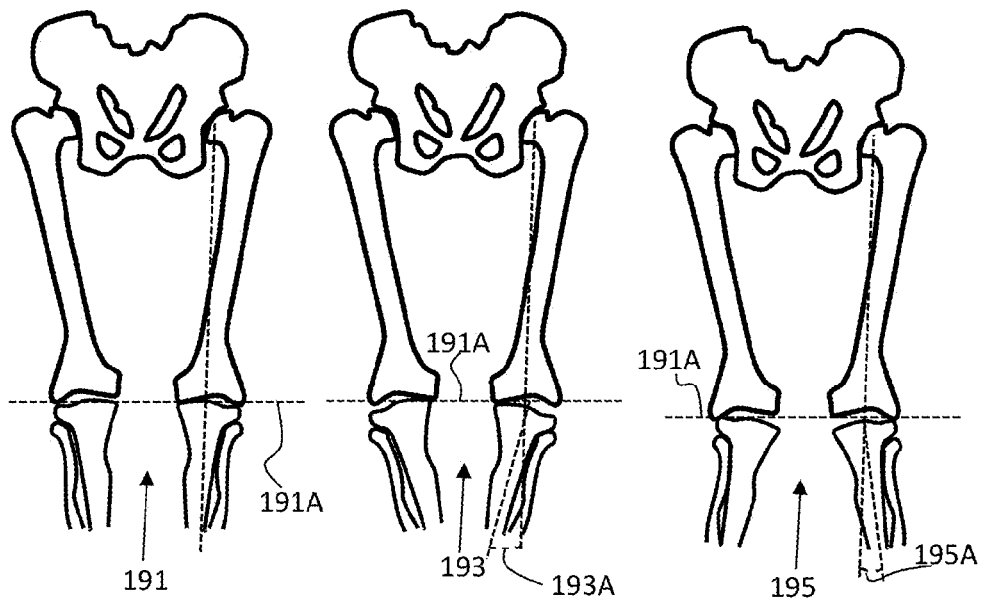
FIG. 1B illustrates the comparison between vargus and valgus.

FIG. 1B illustrates a muscular skeletal system showing a medial lateral line 191A. The mechanical axis of a non-deformed leg is illustrated by the vertical dashed line 191B as illustrated in view 191. View 193 illustrates a leg having a varus deformity. A varus angle 193A illustrates a varus offset with respect to the mechanical axis of a non-deformed leg. View 195 illustrates a valgus deformity. A valgus angle 195A illustrates a valgus offset with respect to the mechanical axis of a non-deformed leg.

FIG. 1C illustrates a kinetic system that includes data displayed in a GUI 100 that can provide feedback to a surgeon 180 before/during/and after surgery on a patient 190. The GUI 100 is displayed on a screen 105, which can be interacted with verbally (e.g., via microphone), or haptically via a hand held control 130, and/or a mouse 110, and/or a keyboard 120. The GUI 100 can provide quantitative measurement data from sensors (e.g., placed in implants, sensor on probes or surgical instruments). A computer, processor, digital signal process coupled to screen 105 can run software programs that use the quantitative measurements from the sensors to visualize the on-going procedure, review measurement data, positions of the muscular-skeletal system, support modifications, and generate workflows based on the quantitative measurement data to support an optimal fit of the prosthetic components. Some non-limiting examples of information include: device type 140, device ID 142, company 144, CP rotation 146, Tibial rotation 148, HKA (Hip Knee Angle) 150, Tibia angle 152, A-P angle 154, flexion 156, implant 157 (e.g., tibial insert), localized load indicators 158, medial and lateral load scales 159 with ranges 160, joint orientation display 162, a signal indicator button 163, a zeroing initiation button 164, a track button 165, a clear button 171, an align button 166, a power indicator 169, a power on button 170, and several other buttons that can be used for other features 167 and 168.

Figure 2:
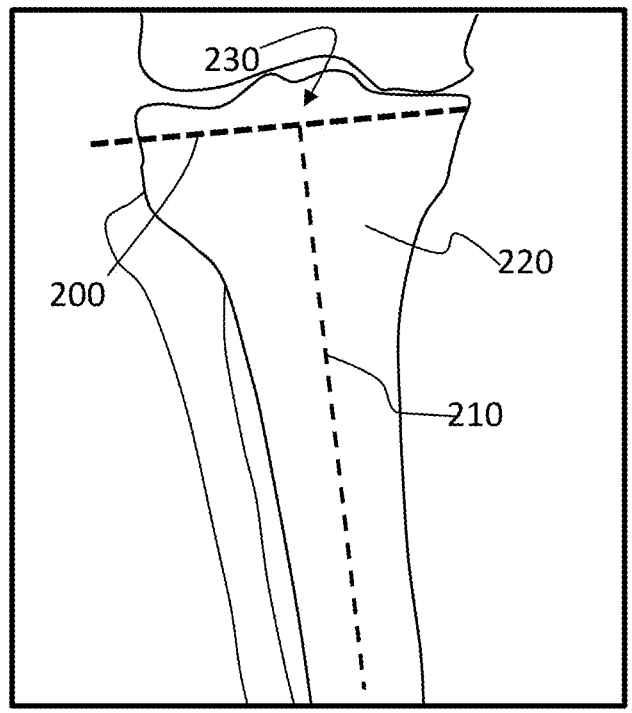
FIG. 2 illustrates a top view of a tibia and associated reference axis.

Initial setup for a knee replacement surgery can involve evaluating a patient's x-rays of the knee joint. FIG. 2 illustrates an AP (anterior-posterior) view of the tibia/knee region. From the view in FIG. 2 the surgeon can define the varus/valgus plane (e.g. plane defined by plane intersecting line 200 and 210) and the depth of proposed bone cuts.

Figure 3:
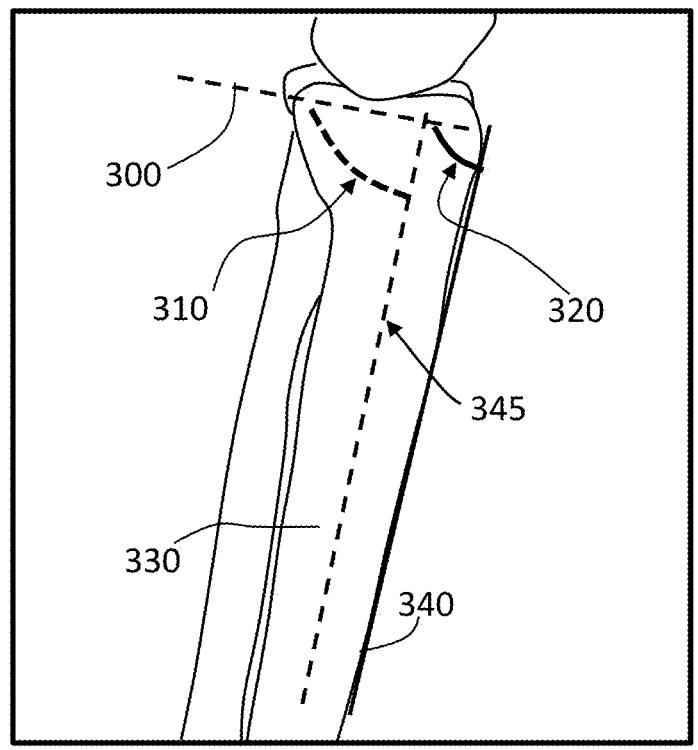
FIG. 3 illustrates a side view of a tibia and associated reference axis.

In addition to AP views the surgeon uses lateral views to determine posterior slope or determine cut angles. FIG. 3 illustrates a lateral view of the tibia knee area. As mentioned the lateral view allows the surgeon to determine the anterior-posterior slope or how much of an angle to cut from anterior to posterior of the proximal tibia trying to recreate the patients natural slope. A bone jig can be attached to the proximal end of the tibia to prepare a proximal end of the tibia 220 for receiving a prosthetic component. The bone jig can be adjusted to provide a medial-lateral bone slope and an anterior-posterior bone slope. As disclosed herein below, quantitative measurements are used to determine kinetic bone cuts under forces that are similar to what the final installed components will see. The kinetic system will provide measurements of the misalignment of the tibia to the mechanical axis of the leg that will be compensated for in the bone jig adjustment for the medial-lateral portion of the tibial bone cut. Similarly, the kinetic system will measure the misalignment of a femur to the mechanical axis of the leg, which can also be compensated for by one or more bone cuts.

In the non-limiting embodiment discussed herein we can use medial-lateral views to determine an AP (anterior-posterior) slope. For example, two lines (330 and 340) intersecting the proximal tibial line 300, will be defined below, but for now make angles 310 and 320 respectively with the proximal tibial line 300, where the difference in the angles (i.e., 320-310) can used in a tibial bone cut calculation. The first line, 330 bisects the tibial canal from the ankle to the insertion of the ACL (e.g., on the anterior ⅓ of the tibial plateau) to the native slope of the tibial plateau. The second line 340 runs parallel to the tibial crest 345 that intersects the tibial plateau native line as well. In the example embodiment, the anterior-posterior slope of the bone cutting jig is adjusted by quantitative measurement under forces similar to that of the final prosthetic component installation as will be disclosed herein below. The amount of anterior-posterior slope cut into tibia 220 is often dictated by the knee joint and the knee joint components being used. For example, if the posterior cruciate ligament is removed an insert with a post is often used to provide support to the joint. An anterior-posterior slope is cut into tibia 220 to support range of motion of the joint in flexion in conjunction with the post.

The measurement device or sensored device comprises at least a pressure sensor system to measure load magnitude and position of load magnitude. The measurement device further includes at least one three-axis accelerometer. In one embodiment, the three-axis accelerometer is referenced to gravity to measure position, rotation, and tilt or slope. The sensing system can be integrated into a prosthetic component. In the example, the sensored device is an intra-operative trial insert. The trial insert includes at least one articular surface that supports movement of the joint. As shown, herein the insert has two articular surfaces. The trial insert is substantially similar in size to a final insert. The trial insert allows all the ligaments, tendons, tissue, and bone structures that apply forces to the joint to be in place during the kinetic assessment to provide quantitative data on load, position of load, and alignment. The trial insert can be wired or wireless for transmitting data to a remote system. The remote system can include a display, software, and a microprocessor, microcontroller, or digital signal process. The remote system is typically outside the surgical field but can be viewed by the surgical team. The sensing system can also be in a trial tibial prosthetic component or a femoral prosthetic component. Similarly, the measurement device can be integrated into a permanent prosthetic component. An example for a knee application integrating the measurement device into a tibial prosthetic component. Alternatively it could be integrated into the permanent femoral prosthetic component or insert.

Figure 4:
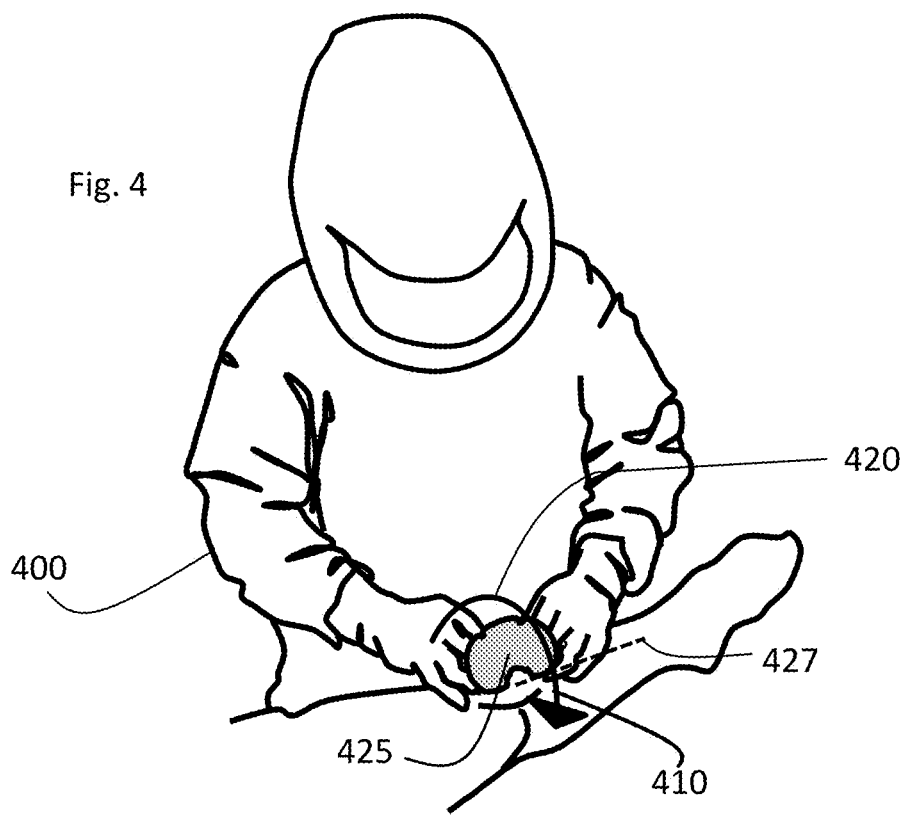
FIG. 4 illustrates a user obtaining a reference axis by moving a sensor.

In FIG. 4 a trial insert or sensored insert 425 is referenced to establish reference planes for position, rotation, and tilt or slope. The insert 425 is referenced to a first plane. In the example, insert 425 is referenced to the operating table. The insert 425 is then referenced to a second plane. The second plane is perpendicular to the first plane. The accelerometer in the sensored insert 425 measures the plane of the operating table in a first direction and then the sensored insert is rotated 180 degrees and a second measurement is taken. The two accelerometer measurements are averaged to remove any slope the operating table may have. The accelerometer is zeroed to the plane of the operating table. The accelerometer is then zeroed to the plane that is perpendicular to the table. A block can be held at a 90 degree angle to the plane of the table and insert 425 held against the block and zeroed to the plane. Alternatively, a structure can be attached or coupled to the table that has a reference plane that is perpendicular to the surface of the table. Insert 425 can be held to the structure and zeroed to plane perpendicular to the operating table surface. A more detailed explanation of the referencing process is disclosed in FIGS. 37 and 38.

A reference position of the joint is established to support further measurement and positioning of the joint. In the example, the leg is placed in a position of approximately extension. The position does not have to be in extension in the strictest definition of the term but a position that the surgeon can repeatably place the leg in. In one embodiment, a tibia reference is captured. The tibia reference represents the position of the tibia when the leg is in full extension. For example, the leg can be placed with the heel touching the operating table at a fixed location. Alternatively, the distal portion of the leg can be placed in a leg holder for repeatable placement and positioning. Upon placing the leg in approximately extension insert 425 will be referenced to a bone landmark or other repeatable reference related to the leg in extension. In the example, the position or angle of a tibial crest 427 is measured by the surgeon 400 when the leg is in extension. Posterior edges of insert 425 are held against a tibial crest 427. The tibial crest is below the tibial tubercle and provides a large surface area to contact. Insert 425 is held approximately perpendicular to the plane of the surface of the operating table on the tibial ridge. The surgeon will move 420 the posterior of insert 425 against the tibial crest until it is stabilized against the crest. A three axis accelerometer 410 in insert 425 measures the an angle of tibial crest 427 in extension. The measurement data is transmitted to a remote system having a GUI. The GUI displays the angle of insert 425 relative to vertical and the angle of tibial crest 427. With the leg in extension the angle of insert 425 is held within −2 and 2 degrees of vertical to ensure an accurate measurement. In one embodiment the system captures the angle of the tibial crest when the angle of insert 425 is within −2 degrees and +2 degrees. Typically, the angle of the tibial crest is approximately 3 degrees for a large portion of the population. The GUI will show the angle of the tibial crest on an indicator from the measurement data transmitted from accelerometer 410 to the remote system. Insert 425 is then referenced to this angle whereby the GUI indicates that the leg is in extension when the tibia is placed in the same position. In one embodiment, a flexion indicator of the GUI is used to display the angle of insert 425 measured to vertical. A tray rotation indicator of the GUI is used to display the angle of tibial crest 427. Thus, a bone landmark has been referenced by the system. A position of extension is indicated on the GUI when the bone landmark is placed in the reference position. In the example, GUI indicators are used more than once to indicate certain steps of a procedure to reduce the number of indicators and reduce clutter on the display. The user of the system can then rapidly synthesize the information being displayed to reduce surgical time. In one embodiment, the AP (anterior-posterior) slope or tilt indicator will be displayed on the display of the remote system after reference the tibia for a position of extension.

Figure 5:
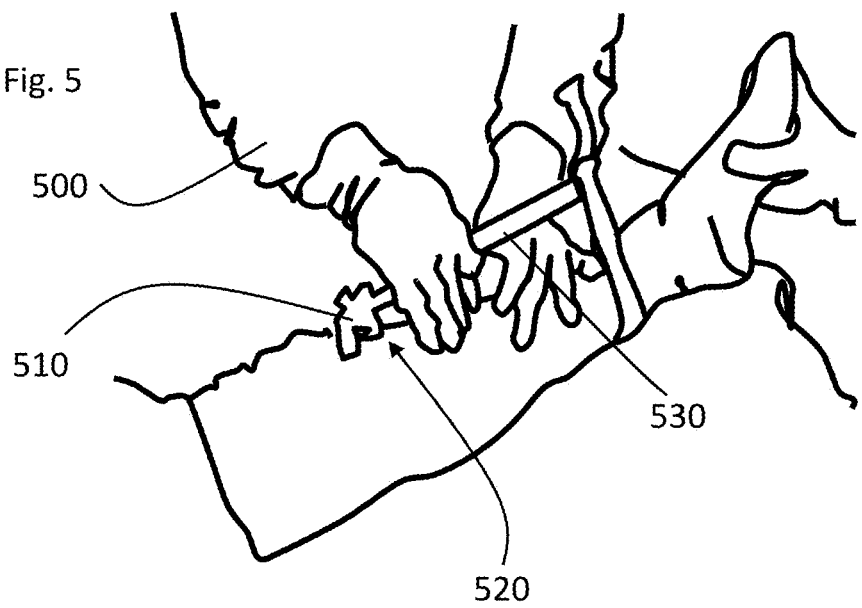
FIG. 5 illustrates a user obtaining an alignment by moving an orthopedic system.

In FIG. 5 a surgeon 500 can place a sensored insert 510 on a proximal portion 520 of tibial bone cutting jig 530. In one embodiment, a shim having a tab is coupled to insert 510. The tab of the shim is coupled to bone cutting jig 530. In the example, the tab is inserted into a cutting slot of bone cutting jig 530. Sensored insert 510 can be used to define through quantitative measurements the medial-lateral (ML) and anterior-posterior (AP) bone cuts of tibial bone cutting jig 530. For example, the accelerometer in sensored insert 510 can be used to measure tilt or slope to obtain a measurement of the jig angle in the AP plane prior to the cut. Furthermore, sensored insert 510 can be similarly placed on a distal femoral jig to define if the sagittal plane is parallel to the tibial cut or to produce a cut offset to the tibial cut. The GUI 100 flexion angle 156 will depict the angle of the proposed tibial cut in the AP plane. The process of using sensored insert with bone cutting jigs will be disclosed in more detail hereinbelow.

Figure 6:
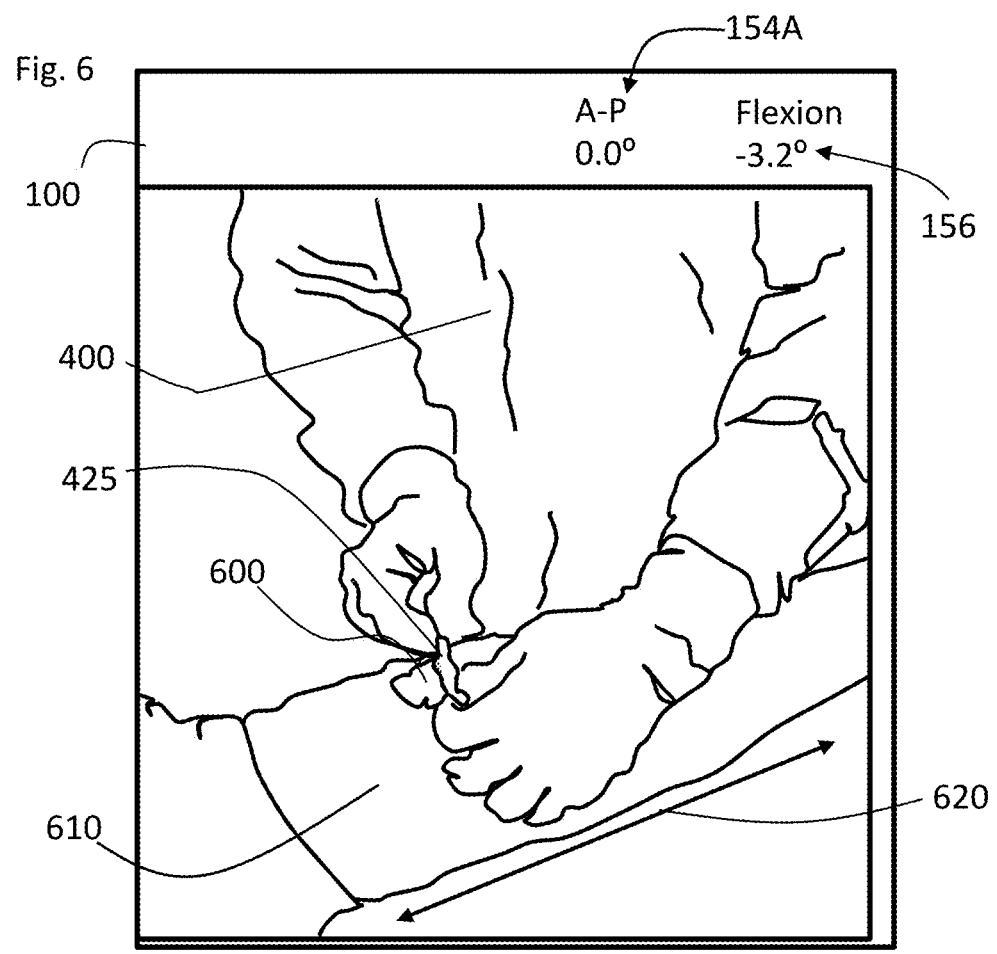
FIG. 6 illustrates a user obtaining alignment data using a sensor.

In FIG. 6 the surgeon 400 takes a sensored insert 425 and places it into a knee tibial prosthetic component 600. Tibial prosthetic component 600 can be a trial or permanent component. Tibial prosthetic component 600 can be fixed to the tibia that supports movement. For example, tibial prosthetic component 600 can be held to the tibia via a single pin that allows rotation. Typically, how tibial prosthetic component 600 is aligned to the tibia is a choice of the surgeon. In one embodiment, tibial prosthetic component 600 is positioned or aligned to a bone reference whereby tibial prosthetic component 600 can be placed consistently from patient to patient. The initial placement or alignment of tibial prosthetic component 600 is a reference position. In general, leg 610 is in flexion when inserting sensored insert 425 into the knee joint. In one embodiment, insert 425 is inserted into a tibial tray of tibial prosthetic component 600. Insert 425 can include a shim to increase or decrease insert height or thickness. A change in insert 425 thickness is required if the joint is too loose or too tight when moving through the range of motion. The tibial tray retains insert 425 in a fixed position relative to tibial prosthetic component 600. Insert 425 couples to a femoral prosthetic component and tibial prosthetic component 600. Insert 425 has at least one articular surface. In the example, has two articular surfaces that allow the leg to move through a range of motion. The leg can then be placed in extension 620 as measured by the accelerometer and indicated on GUI 100. The AP box 154A on the GUI is clicked to measure the AP slope or tilt of the proximal tibial cut as referenced to the tibial crest or any chosen referenced plane (e.g., cutting rod etc. . . . ). In general, the accelerometer in insert 425 is coupled to the tibia and measures the anterior-posterior slope of the bone cut on the proximal end of the tibia relative to the referenced tibial crest. Thus, the A-P slope measurement can be made independent of the leg position.

FIGS. 7 and 8 illustrate the surgeon 400 or surgical team interfacing with the GUI to set A-P slope. In particular, box 154A and box 156A of the GUI are shown. Box 154A and Box 156A respectfully correspond to A-P (anterior-posterior) slope and flexion position of the leg. In FIG. 7 the leg is moved into a position 701 of extension. As shown, the measurement can indicate that the leg is hyper-extended with a negative reading (e.g. −3.5 degrees) relative to the floor. In the example, the proximal end of the tibia has been cut with an anterior-posterior slope or tilt. The tibial tray of the tibial prosthetic component takes on this slope when mounted to the tibia. Thus, the insert in a knee 610 couples to the tibial tray of the tibial prosthetic component and measures the anterior-posterior slope thereof, which appears to show a hyper-extended knee. Note that in at least one embodiment the AP box shows the slope, and the flexion angle is relative to the floor or gravity.

FIG. 8 illustrates measuring and setting the A-P slope on the GUI. The leg remains in extension or the same position when the Tibial reference was taken, until Box 154A is selected or clicked on. The measurement of the A-P slope is then taken. The flexion measurement of Box 156A is transferred to Box 154A. In the example, a positive slope for A-P corresponds to the anterior side proximal end of the tibia being higher than the posterior side. Thus, the A-P slope as shown is measured at 3.5 degrees in the example. The A-P slope measurement can be used to verify that the cut was correct. If the A-P slope is incorrect as shown by Box 154A correction or modification can be undertaken to change the slope. The A-P slope is stored in memory and can be used in further computations and measurements. Changes to the slope can be re-referenced after adjustments are made. The resultant position is the optimized position of the accelerometer in the sensored insert to define the proximal tibial A-P angles that were cut. As will be disclosed herein below the sensored insert can be coupled to a tibial bone cutting jig pre-cut to define a tibial cut of 3.5 degrees A-P slope. In general, an A-P slope is useful to define flexion gap balance and equalize loading when the leg is moved from extension into flexion.

FIGS. 9 and 10 illustrate the surgeon measuring the offset of the tibia to the mechanical axis of the leg. Prior to measuring the offset the CP (contact point) rotation is set. The CP rotation corresponds to a reference position of the tibial femoral prosthetic component to the prosthetic component. The Tibial Try Rotation box corresponds to a reference position of the tibial tray. For example, many surgeons align the center of the tibial tray of the tibial prosthetic component to the medial third of the tibial tubercle or other landmark. As mentioned previously, the tibial tray can be pinned to the tibia in a manner that allows rotation of the tibial prosthetic component from the reference position. A Tibial Rotation box on the GUI is selected or clicked once the reference position of the tibial tray is established. Any change in the position of the tibial tray is indicated in the Tibial Rotation box of the GUI. In one embodiment, the reference position is listed as zero degrees in the Tibial Tray Rotation box. Alternatively, CP Rotation can indicate an amount of tray or insert rotation relative to the femoral condylar contact on the tibial tray. Rotating the tibial prosthetic component will yield a positive or negative number in the Tibial tray Rotation box depending on the direction of rotation. In one example, rotating the tibial prosthetic component can be used to affect the position of load and the load magnitude over the range of motion. In one embodiment, the GUI can indicate if the load magnitude is within a predetermined load range. Similarly, the GUI can indicate if the position of load is within a predetermined position range. The value of CP Rotation can be used in measurement and calculations of other parameters such as the congruency of the tibial and femoral implants through a full range of motion.

In FIG. 9, the knee joint is placed in flexion. In the example, the sensored insert is positioned to be at approximately a 45 degree angle to the plane of the surface of the operating table. The heel is positioned in a fixed position to achieve the sensored insert angle optimized position for reading outputs. The GUI directs the surgeon to this flexion angle. In one embodiment, the heel is placed on the surface of the operating table. The position of the heel on the operating table should fixed in place as it will be a first pivot point for moving the knee joint. Surgeon 400 can hold and stabilize the ankle and heel to minimize movement during the measurement. In one embodiment an align button on the GUI is pressed to initiate alignment measurements. Surgeon 400 now follows a needle point graphic or tracking grid 930 on the GUI to begin rocking the knee back and forth with the heel 910 placed firmly on the operating table in a stable position, to allow pivoting 920 on the heel to define a plane to reference to. As shown, the knee joint is pivoted in the lateral direction and tracking grid 930 tracks the movement. In FIG. 1C, the knee joint is pivoted in the medial direction and tracking grid 930 tracks the movement. The surgeon limits the movement within the range of tracking grid 930. In general, a maximum of the arc made by the knee joint is being identified by the system. The range of the arc is less or equal to plus or minus 45 degrees from vertical. In one embodiment, the arc is less than or equal to plus or minus 10 degrees from vertical. The maximum has to be within the range of tracking grid 930. Reducing the range of the arc improves measurement accuracy since the same amount of measurements are taken for any given range. The knee joint is rocked to the medial side and the lateral side more than one time. In one embodiment, the knee joint can be rocked back and forth ten times or less to identify arc maximum. Increasing the analog to digital converter accuracy can be used to reduce the number of rocking motions. In one embodiment, the analog to digital converter accuracy used in the measure of the arc maximum utilizes DAC's (digital to analog converters) having 15-bit or greater accuracy. The number of rocking motions can be reduced to four or less rocking motions using a DAC's of 15-bit or greater accuracy which reduces the time and effort required by surgeon to measure points in the arc. In general, the accelerometer is referenced to three axis. A first axis corresponds to the A-P (anterior-posterior) line of the knee joint. A second axis correspond to the M-L (medial-lateral) line of the knee joint. The third axis is perpendicular to the plane of the first and second axis. In one embodiment, the sensored insert is measuring and finding the maximum gravity in the X-direction or along the A-P line. At maximum gravity in the X-direction raw tibial tray rotation of the tibial prosthetic component should be zero in the Y-direction or along the M-L line. In the system, Y-direction/X-direction is rotation and tilt is Y-direction/Z-direction. If the measurement is not zero then the tibia has tilt which is measured. The amount of tilt can be related to a varus or valgus angle relative to the mechanical axis. Thus, as the surgeon 400 is pivoting 920 on the heel, the system searches for the Max G for the sensored insert. The location of the maximum is used to determine an offset from the mechanical axis of the leg. The offset corresponds to a varus-valgus angle for the tibia.

As mentioned previously, the knee joint can be positioned where the sensored insert is at a 45 degree angle relative to the surface of the operating table to improve measurement accuracy. The aforementioned position of the insert is a point where the axis of the A-P line and the axis normal to the plane are approximately equal in terms of the effect of gravity. In one embodiment, the flexion box in the GUI can indicate when the sensored insert is in an optimal position prior to measuring the leg alignment. For example, the number in the flexion box can change color to indicate that the leg is positioned for measurement.

Figure 11:
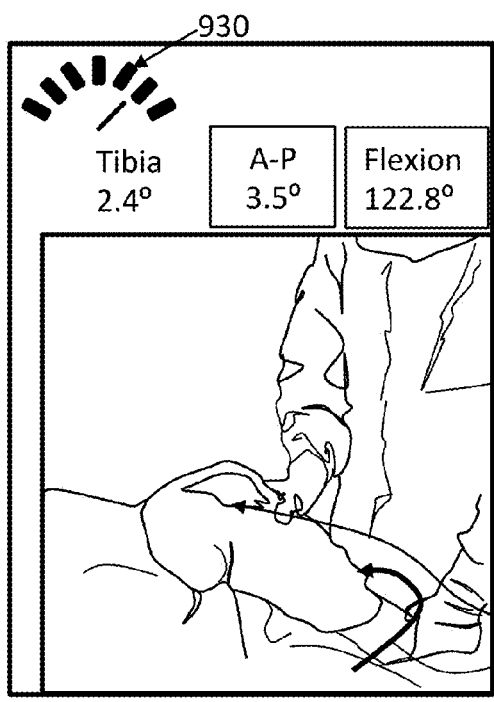
FIGS. 11 and 12 illustrates a user moving an orthopedic system in flexion to obtain alignment data

FIG. 11 illustrates a measurement of a tibia angle relative to the mechanical axis appearing on the GUI. In the example, the knee joint is pivoting 920 off of the heel of leg 610. The heel and ankle are held together to prevent movement of the ankle. The knee joint is moved back and forth in a medial direction and a lateral direction a predetermined distance as indicated in tracking grid 930 (e.g. needle point graphic on the GUI). The back and forth movement of the joint is performed a predetermined number of times. A calculation of the varus-valgus angle appears on the display and is listed under tracking grid 930 as "Tibia" in the GUI. The varus-valgus angle corresponds to the medial-lateral tilt of the proximal end of the tibia. For example, the tibia is in alignment to the mechanical axis if the max G position corresponds to the A-P line. If the max G position is offset from the A-P line then an offset exists relative to the M-L line that can be converted to a varus-valgus angle. The A-P slope and angle of flexion is also indicated in the GUI.

The pace of the rocking motion can be dictated by tracking grid 930. The surgeon will try to pace the movement of the knee joint back and forth to lead the needle shown in the GUI. For example, moving the knee joint too quickly will result in the needle not being able to follow the leg movement. The correct pace allows the needle to track movement of the knee joint. The knee joint movement should not move the needle outside either extreme. The sensed insert is taking quantitative measurements over the arc to determine the position of Max G.

Figure 12:
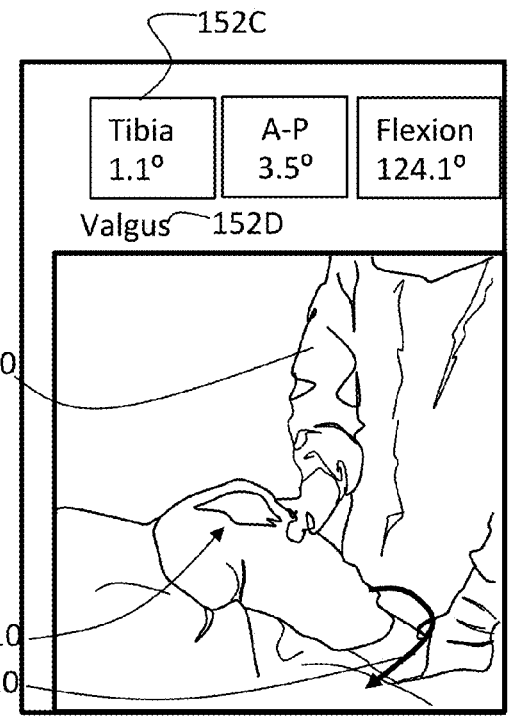

FIG. 12 illustrates a completed measurement of the tibia relative to the mechanical axis of the leg. The knee joint has been rotated back and forth the predetermined number of times. Data points have been taken to determine the maximum along the A-P line of the joint. The amount of tilt or slope on the tibial plateau can be calculated from the position of the maximum. Tibia angle 152C is indicated on the GUI. A final calculation of tibia angle 152C can be indicated by changing the display color and placing a box around the number. The GUI further indicates whether the tibia angle is varus or valgus 152D relative to the mechanical axis.

Figure 13:
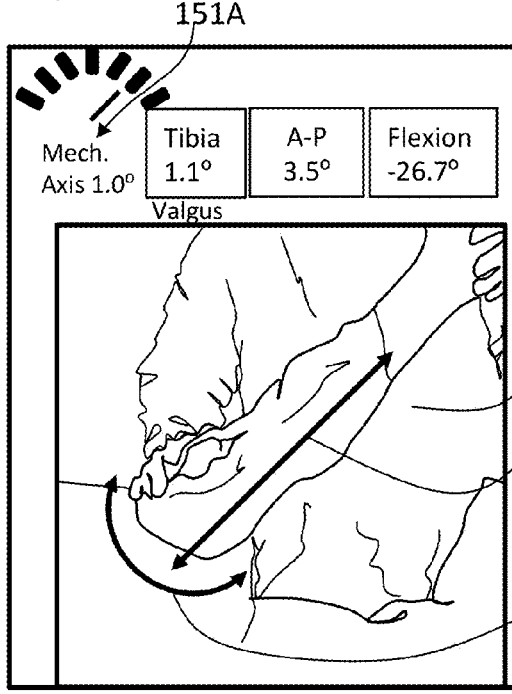
FIGS. 13 and 14 illustrates a user moving an orthopedic system in elevated extension to obtain alignment data.

FIG. 13 illustrates a measurement of the femur of the leg relative to the mechanical axis of the leg. The workflow of the system having now captured the tibia offset to the mechanical axis now captures the bone tilt or slope of the distal end of the femur. In general, the difference in the leg alignment when compared to the mechanical axis is calculated by subtracting the medial-lateral bone tilt of the distal end of the femur from the medial-lateral bone tilt of the proximal end of the tibia. This difference is listed on the GUI underlying Mech. Axis (e.g. mechanical axis) based on the tibia and femur quantitative measurements.

In one embodiment, the leg is placed back in extension 620. The leg is lifted in extension 620 such that the distal end of the femur is loaded by the knee joint. The leg in extension 620 is lifted until the sensed insert in the knee joint is at a 45 degree angle or an optimized angle as depicted on the GUI to the surface of the operating table.

The leg is lifted so the leg is pivoting 620 off of the femoral head of the femur. The leg is lifted such that the sensed insert in the knee joint is at a chosen angle, for example approximately 45 degrees. In the example, the numbers in the GUI under Mech. Axis will change color and a box is placed around the numbers when the sensed insert is about the chosen angle, for example in the 45 degree position. The surgeon 400 now takes the leg in the extended position 620 and moves the knee joint back and forth in the medial and lateral direction. This will allow the system to subtend the plane of the distal femoral implant or distal femoral angle. As mentioned previously, the leg is pivoting off of the femoral head of the femur when rocking back and forth.

Figure 14:
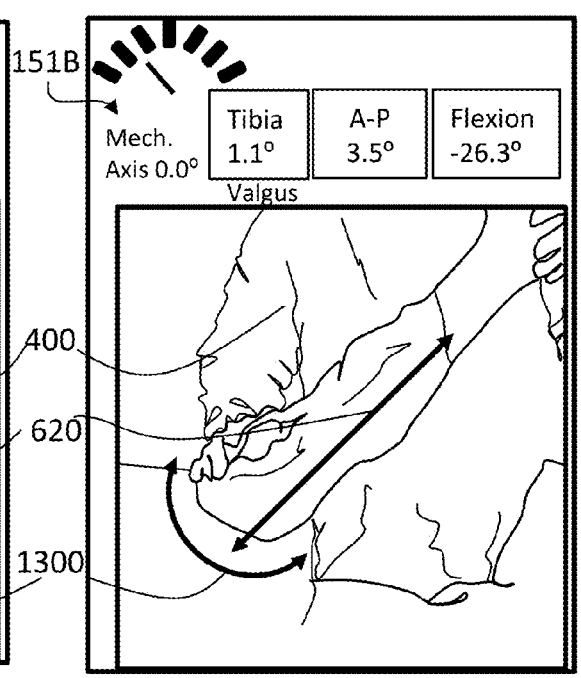

In FIGS. 13 and 14, the leg is pivoted 1300 on the femoral head of the femur. The knee joint is rocked back and forth and is tracked by the tracking grid on the GUI. The surgeon moves the leg at a pace that the tracking grid keeps up with the movement. Thus, the tracking grid limits or controls how fast the surgeon moves the knee joint. The range of the movement is also limited by the tracking grid shown in the GUI. The surgeon limits the movement within the range of the tracking grid. In one embodiment, the surgeon moves the knee joint back and forth to either extreme of the tracking grid. The knee joint moves in an arc. The system will measure and identify the Max G position of the sensed insert pivoted 1300 off of the femoral head of the femur and calculate the tilt or slope of the medial-lateral distal end of the femur. The tilt of the distal end of the femur is incorporated with the previously measured tilt of the measured proximal end of the tibia to output an offset relative to the mechanical axis as depicted in the GUI in 151A and 151B. In one embodiment, the number can be changing as the leg is rotated back and forth. The varus-valgus angle is a measure of the offset of the femur to the mechanical axis and corresponds to the measured medial-lateral tilt of the distal end of the femur. For example, the femur is in alignment to the mechanical axis if the max G position corresponds to the A-P line. If the max G position is offset from the A-P line then an offset exists relative to the M-L line of the distal end of the femur that can be converted to a varus-valgus angle for the femur. Thus, the varus-valgus offsets of the tibia and femur relative to the mechanical axis is measured.

Figure 15:
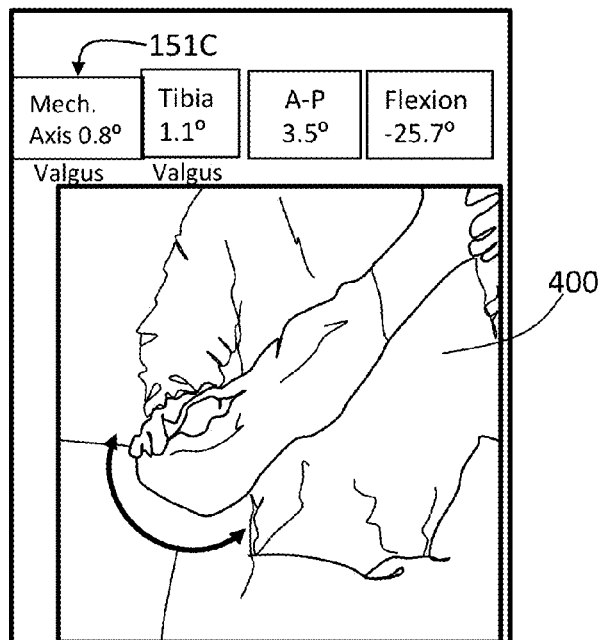
FIG. 15 illustrates a user moving an orthopedic system in elevated extension to obtain alignment data.

FIG. 15 illustrates a surgeon 400 rocking the leg in extended position, pivoting on the femoral head, and the Max-G is identified by accelerometer measurements of the sensed insert such that the mechanical axis offset 151C is boxed. The boxing of the Mech. Axis value is an indication that the predetermined number of rotations has been completed and the offset value of relative to the mechanical axis has been calculated. In the example, the mechanical axis offset is measured as 0.8 degrees. This indicates that the distal end of the femur was measured having a varus angle of 0.3 degrees. The combination of the tibia and femur offsets yields a value of 0.8 degrees from the mechanical axis. In general, the measurement can be used to verify that the leg measures within a predetermined range of the mechanical axis. For example, there have been clinical studies that indicate that an offset greater than 3 degrees can have significant issues with joint reliability. The surgeon can verify to a high degree of accuracy that the leg alignment is well within this limit. Moreover, as data is taken with different bone geometries it may become standard to cut at specific offsets for optimal fit and where which can be accomplished by using the system with a bone cutting jig as will be disclosed herein below. The surgeon can now evaluate the Total Knee Replacement (TKR) result as it relates to alignment of the legs, alignment of the bony cuts, the soft tissue tension and femoral-tibial implant congruity.

Figure 16:
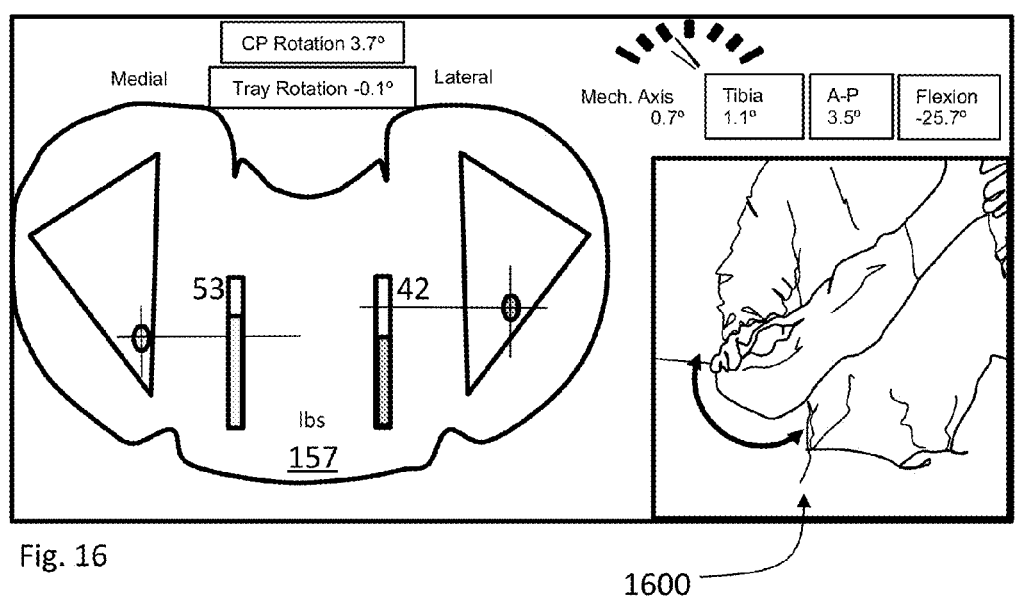
FIG. 16 illustrates an electronic display showing a schematic of a sensor, with orthopedic parametric values and a display of the orthopedic system.

FIG. 16 illustrates a non-limiting example of a GUI that the surgeon can view which provides quantitative data, visualization, and feedback. In one embodiment, the system can include a video recording of the procedure. It illustrates a video 1600 of the surgeon manipulating the leg, a representation of a sensed insert 157, with associated angular readings (e.g., CP Rotation, Mechanical Axis angle, Tibia angle, AP angle, Flexion angle, and Tray rotation), and loadings.

Figure 17:
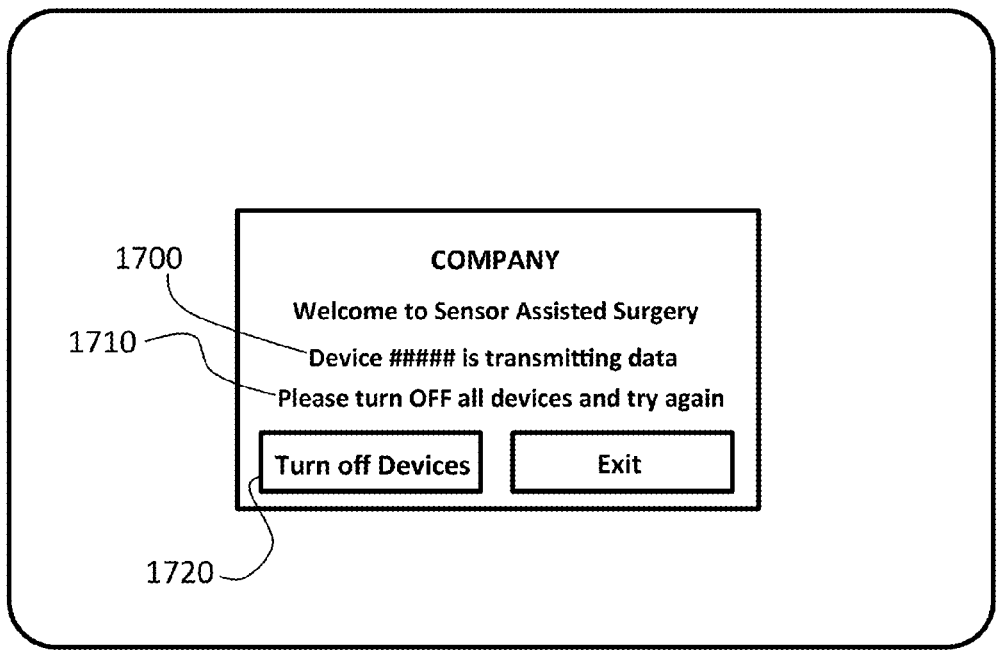
FIGS. 17-36 illustrates portions of a software display of a user assist computer program.
Figure 18:
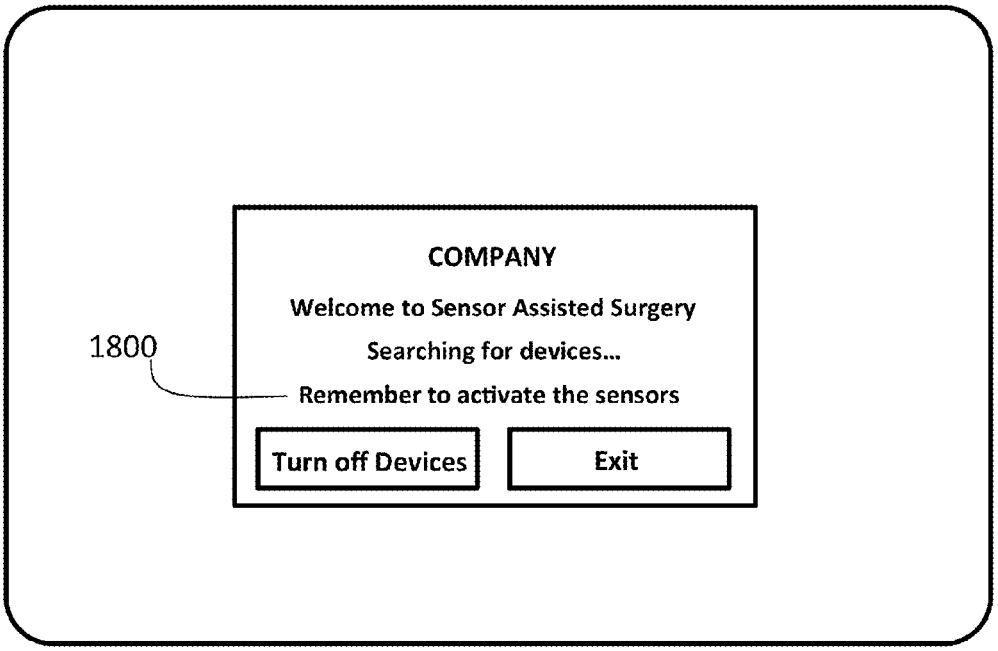

FIGS. 17-34 illustrate a GUI software system in accordance to at least one embodiment of the invention, which displays information that a surgeon can use during surgery. FIG. 17 illustrates a start screen when the software system is begun. The software system checks to make sure all devices (e.g., sensors) linked to the system are turned off. If there are devices on, a message is displayed 1710 to notify the user to turn off the devices and will also indicate 1700 which device(s) are transmitting data. The user is provided a button 1720 that can be selected for the software system to shut off devices for the user. When the devices are off and not transmitting data, the system can initialize any new device that transmits data, search for devices, and remind 1800 the user to activate the sensors if not detected (FIG. 18).

Figure 19:
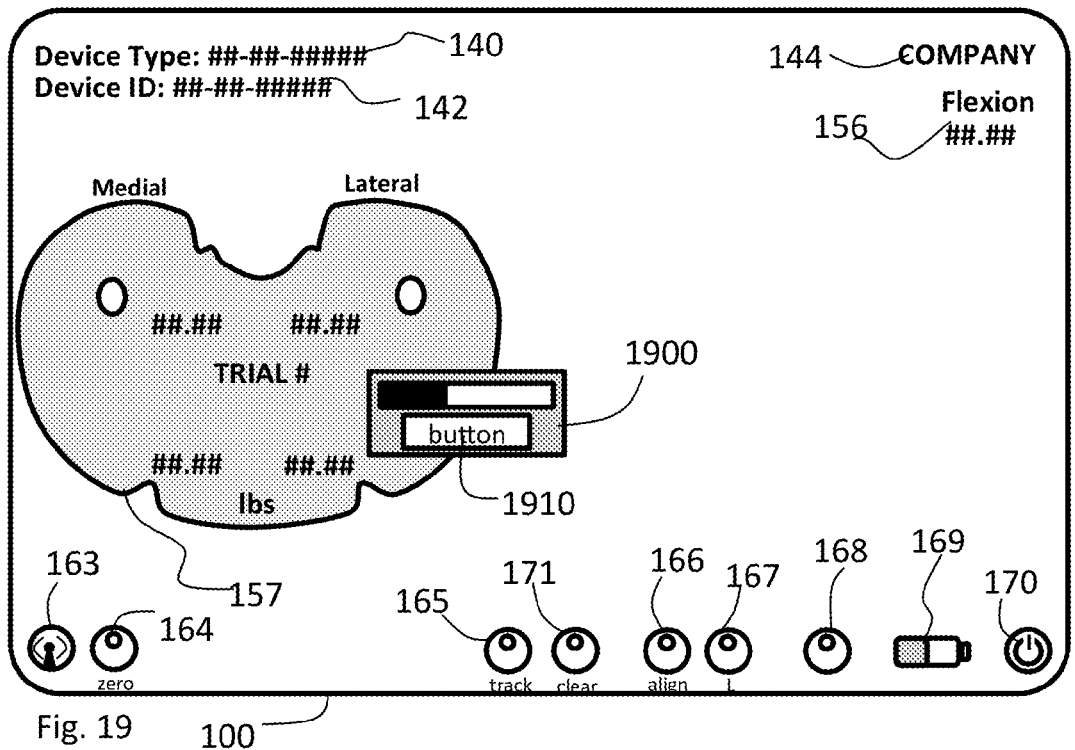

FIG. 19 illustrates the GUI system 100 after software activation and sensor detection. The GUI system 100 indicates a progress bar 1900 showing the initializing of sensors (e.g., load sensors) a cancel button is provided 1910 to allow the user to stop the process. The GUI 100 can contain multiple information, for example device type 140, device ID 142, company 144, flexion 156, device, module, or prosthetic component 157 (e.g., tibial insert), a signal indicator button 163, a zeroing initiation button 164, a track button 165, a clear button 171, an align button 166, a power indicator 169, a power on button 170, and several other buttons that can be used for other features 167 and 168.

Figure 20:
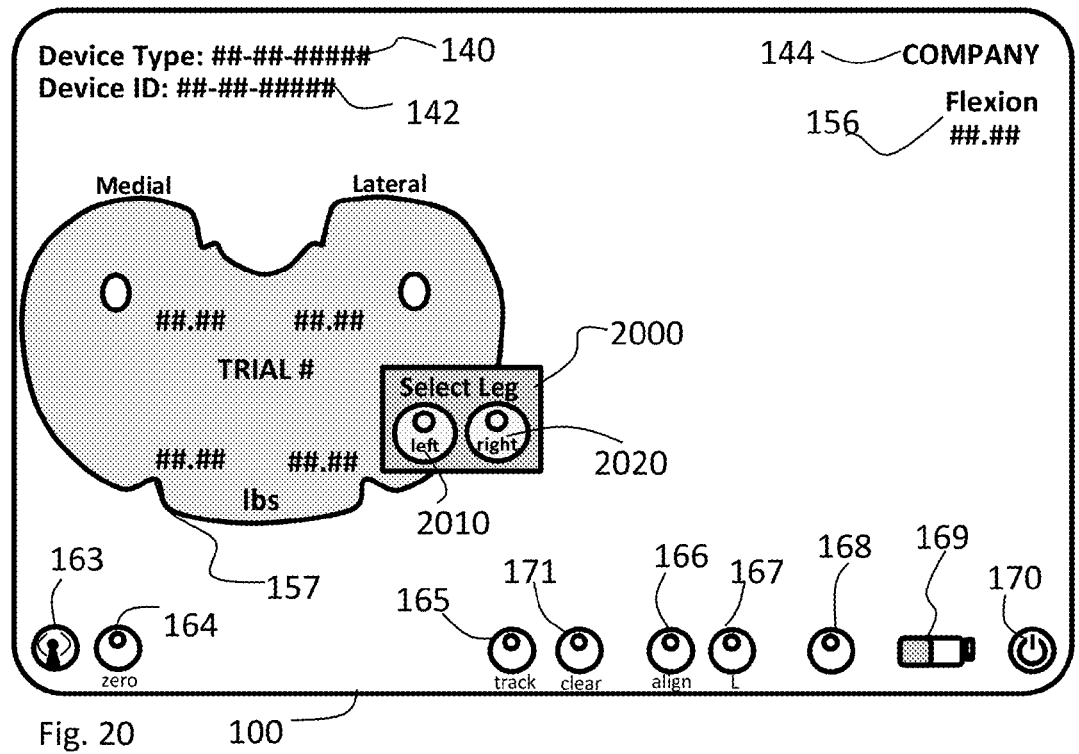

After initialization, the user is prompted 2000 to select a particular anatomical feature (e.g., left 2010 or right 2020 leg) that the sensors are being used for (FIG. 20).

Figure 21:
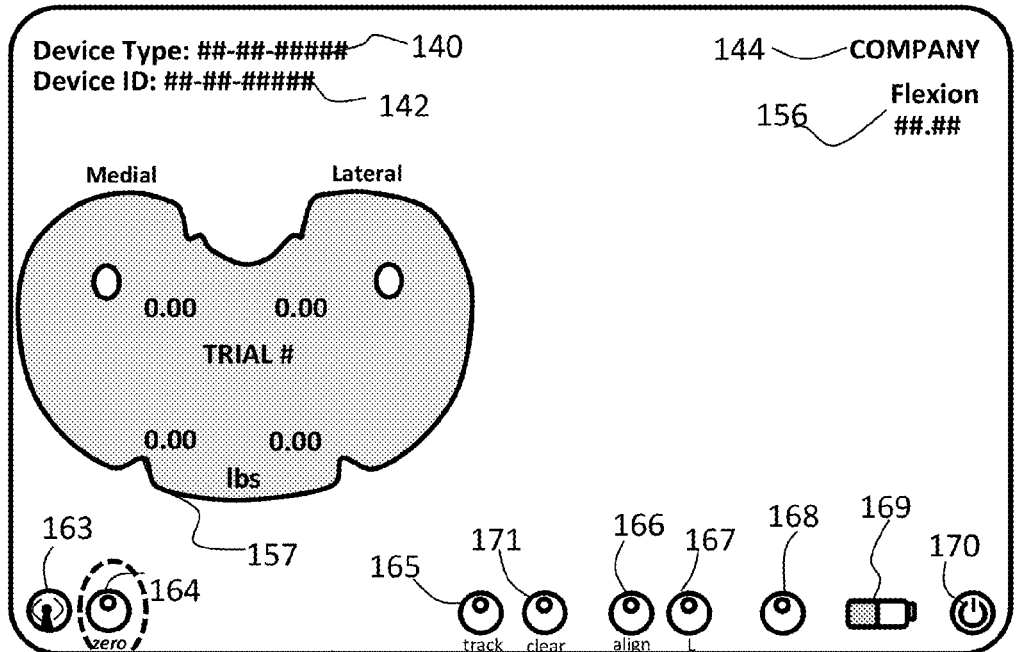
Figure 22:
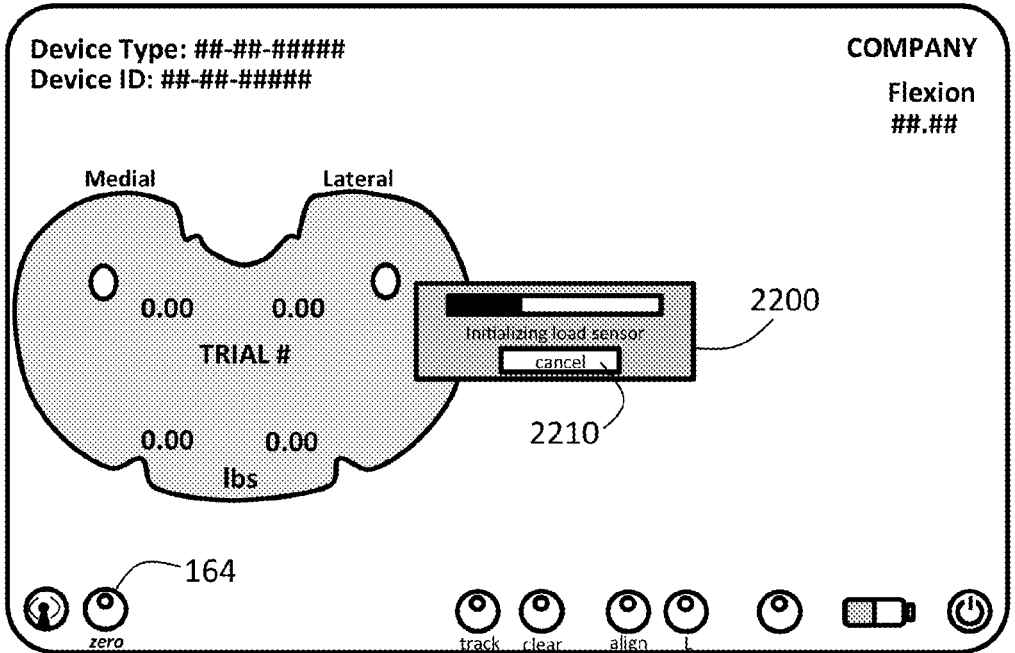

FIG. 21 illustrates the GUI 100 after initialization and feature selection. The user is prompted to zero the sensors (e.g. zero button 164 turns red). In operation, during this stage, the prosthetic device is coupled to a reference surface. In one embodiment, the sensored insert is placed flat upon an operating room (OR) table and then a user selects the zero button 164 on the GUI to reference to the OR table surface. Once pressed the software zeros the offsets in the sensors. As mentioned previously, the sensored insert utilizes at least a three-axis accelerometer that is referenced to gravity to measure position, tilt, and rotation. When the zero button 164 is selected the GUI 100 notifies 2200 the user that the sensor is being zeroed, and optionally provides a button 2210 to allow cancellation of the zeroing by the user (FIG. 22). The zero button 164 can be deactivated (e.g., the text changes from red to black) when the notification 2200 is provided.

Figure 23:
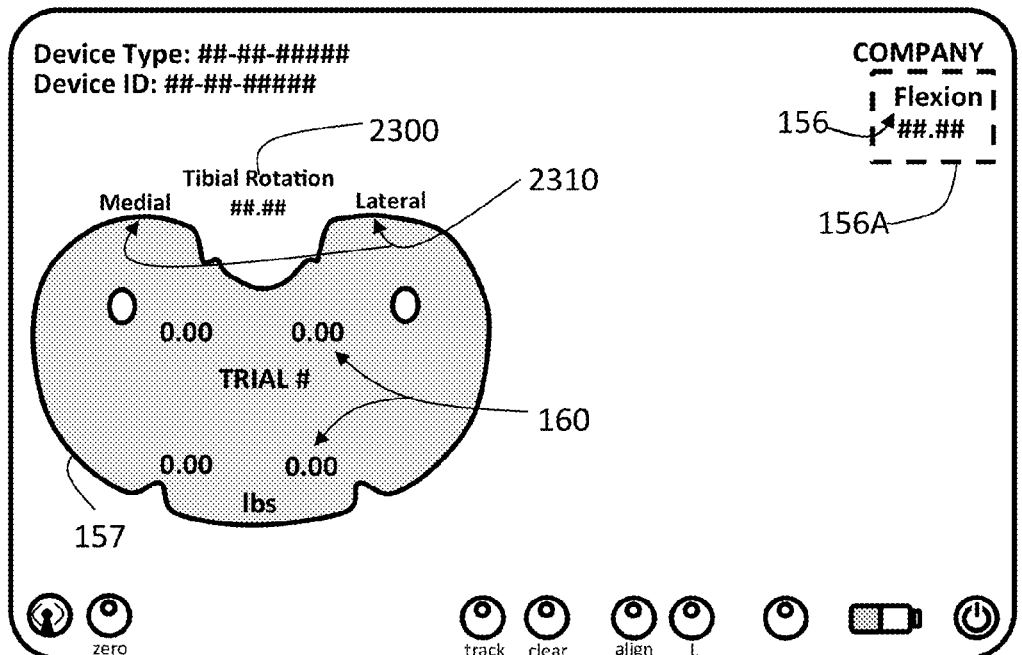

FIG. 23 illustrates the GUI 100 display when the zeroing process is complete. On GUI 100 a Tibial rotation 2300 is also displayed. In one embodiment, tibial rotation 2300 corresponds to an amount of rotation of a tibial tray of a tibial prosthetic component from a reference position. The sensored insert zero'd in the plane of the table can have a zero value for the x and y values. At this point the device (e.g., implant 157) has not been placed in the anatomical feature (e.g., leg), and the loading 160 in the device shows 0.00 load values. After zeroing the device the first time it can be rotated on the table about 180 degrees and zeroed a second time for the new position. The software system can average the measurement values at the two positions, minimizing affect of the slope of the table. The x-y values have been obtained for the accelerometer in the sensored insert (in the plane of the OR table). The device is then stood vertically and positioned against a plane perpendicular to the surface of the OR table to zero to a reference z-plane. In one embodiment, a reference block having a z-plane surface is held against the surface of the OR table. Alternatively, a z-plane surface is available on the OR table. After obtaining the zero reference values in the x-y plane and the z direction, the device/sensor can be translated into a sterile field (e.g., for operation).

Once moved to a sterile field, the tibia reference is captured, or the reference of the position of the tibia when the leg is in full extension (e.g., heel resting on table or leg holder). In the example, this is a reference position selected by the surgeon that corresponds to the leg in extension. This is done by resting the posterior edges 2310 of the implant 157 along the tibial crest (see FIG. 4) or any other bony prominence to define a plane. Tibial Rotation 2300 is used to measure the angle of the tibial crest relative to the plane of the OR table. Thus, tibial rotation 2300 that is provided from the GUI is the tibia crest reference angle and not the tray rotation in this measurement. The user can then click on the Flexion 156, where a blinking box 156A appears, waiting for the user to now to rotate the implant 157 vertically (in at least one embodiment within a range from −2 to 2 degrees) while one contact remains on the tibial crest till the flexion angle is near zero.

Figure 24:
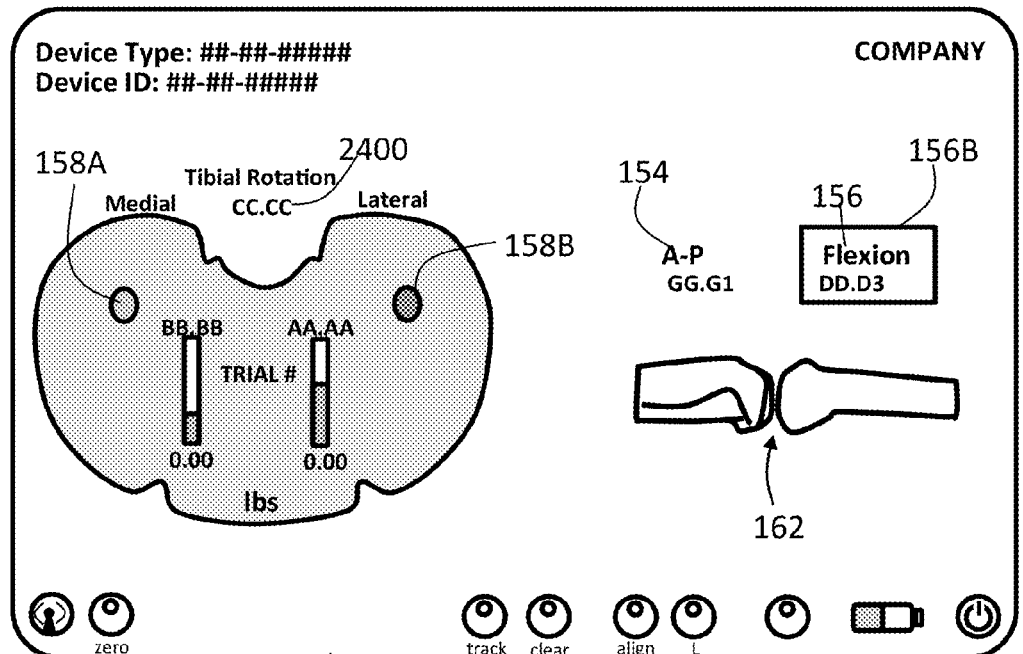

A blinking box 156A becomes a solid line 156B box when the sensored insert is on the tibial crest and is approximately vertical. Tibial rotation 2300 of GUI 100 then displays the tibia crest angle. The anatomical feature 162 of the femur and tibia are displayed in extension when the tibia is at the measured tibia crest angle (FIG. 24). Note that the A-P (Anterior-Posterior) slope of the proximal end of the tibia or the tibia plateau can be measured with the leg in extension. The measurement of the A-P slope is relative to the tibia crest. Note also that the tibia crest angle is roughly 2-3 degrees off of the mechanical axis of the tibia for a majority of patients. A shim can be coupled to the sensored insert to adjust height. The sensored insert can be placed in the knee joint and coupled to the tibial tray of the tibial prosthetic component.

FIG. 24 illustrates the GUI 100 when the sensor module is placed in the anatomical feature. In the example, the sensor module is the sensored insert that is placed in the knee joint. The displayed sensor system displays a value for the Tibia Rotation 2400, the load values (e.g. lbs.), and the center of load indicators are displayed (e.g., 158A and 158B) also referred to as the contact points (CP). To zero the Tibia Rotation a user can then click on the display of the Tibial Rotation 2400. The zero location can correspond to a position designated by the user that establishes a reference or starting position of the tibial prosthetic component. In one embodiment, the tibial tray of the tibial prosthetic component is aligned to a bone landmark or feature as a starting point. Alternatively, the insert can be rotated to a predetermined measured position and zeroed. When the sensored insert is placed in the tibial prosthetic component the flexion value DD.D3 represents the position in extension and the A-P slope of the tray in which the device has been inserted. In one embodiment, the A-P slope of proximal end of the tibia bone cut at an angle from front to back. This A-P slope is measured by the accelerometer which changes the flexion value 156D from extension where the sensored insert may think the device is hyperextended. In general, a leg in extension should measure zero degrees. The reading in box 156D is the amount of A-P slope measured from the vertical. The user now selects or clicks on the lettering in GUI 100 for A-P 154D. The value in box 156C that corresponds to A-P slope is transferred to box 154C or A-P slope 154D. The flexion measurement 156D transitions to a number near zero (FIG. 25), where the A-P value 154D is now the negative of the flexion value or −DD.D3, or positive (since DD.D3 was negative). At this point the A-P value 154D is measured with respect to the tibia crest. The A-P value 154D can be used to determine the slope of the tibial plateau bone cut. The measurement can be used to verify that the cut is correct and corresponds to the cutting jig cutting angle for the tibia. Before the next stage of alignment rotation values can be captured. The user can click on the lettering CP Rotation on the GUI 100.

Figure 25:
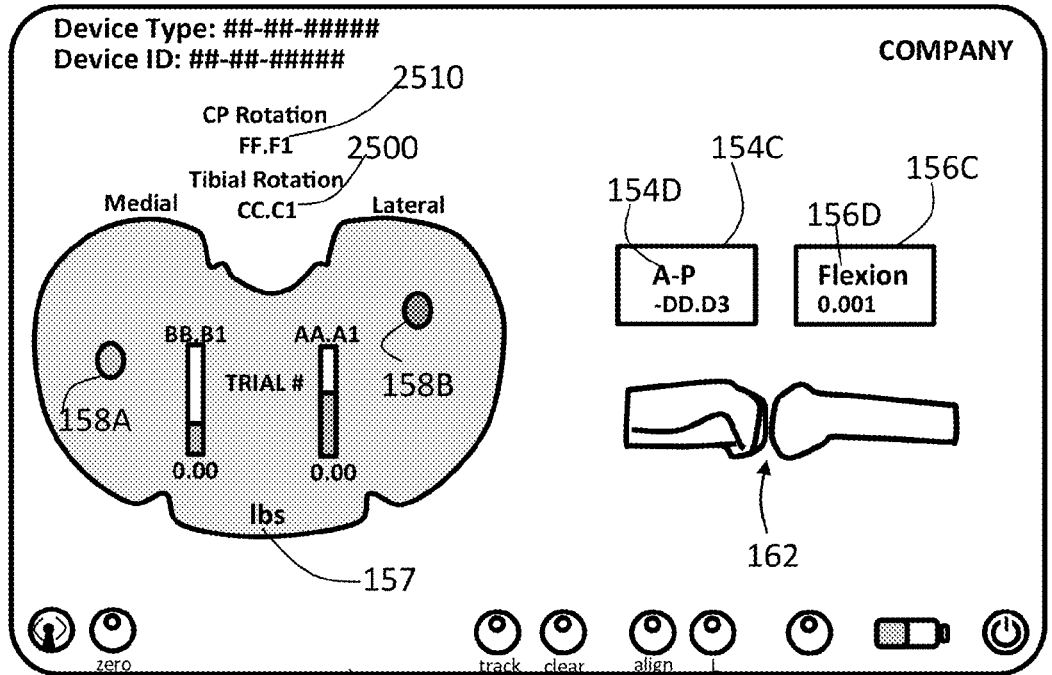

FIG. 25 also illustrates the GUI 100 when the tibia rotation angle 2500 is zero'd. When the Tibia rotation angle is zero'd, Contact Point (CP) Rotation angle 2510 is displayed. Note that the Tibia Rotation 2500 will start to indicate values from zero. A positive CP rotation value is an external rotation (e.g., counter clockwise rotation on the page). An external rotation is a rotation of the device toward the lateral side. The CP rotation angle 2510 is the angle a line through the lateral contact point and the medial contact point makes with a horizontal plane, which is perpendicular to the OR Table (or floor). Thus, the implant 157 image (e.g. sensored insert), illustrating a view looking toward the head from the knee, is rotated into the page counterclockwise, which would be a left leg lateral rotation (hence positive CP rotation angle). As mentioned previously, the user can position the tibial prosthetic component and the sensored insert in a predetermined location. The user can choose to zero at this reference position. Rotating the tibial prosthetic component and the sensored insert from this zero or reference position would be measured and displayed as CP rotation 2510.

Figure 26:
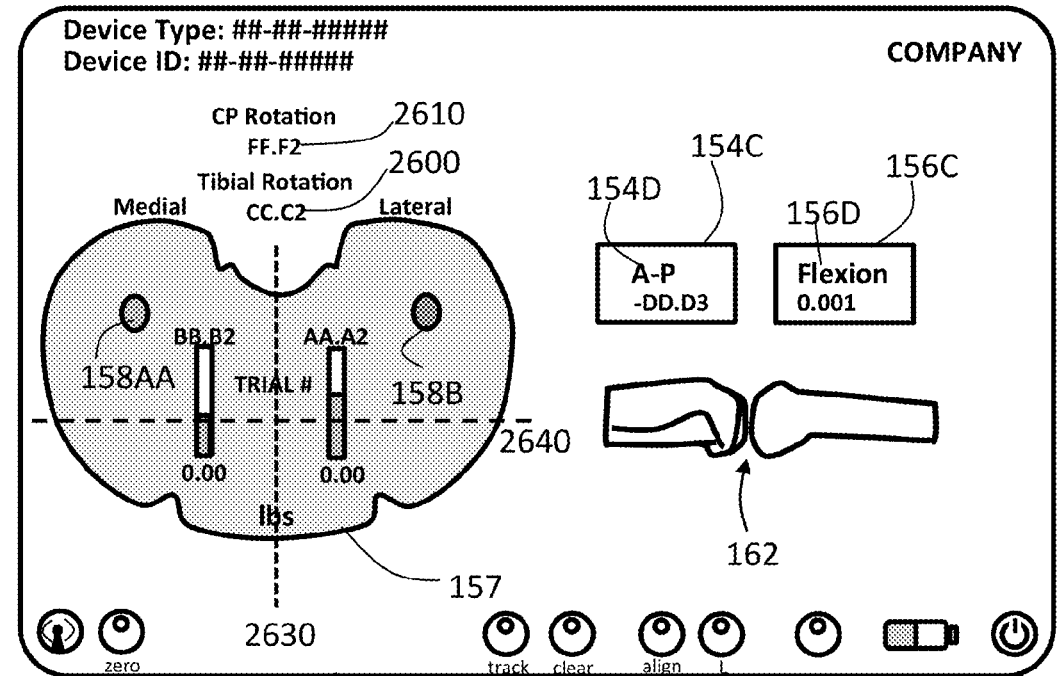

FIG. 26 illustrates the GUI 100 when the surgeon balances out the contact points. The surgeon, at full extension or any knee flexion angle of the limb, can try to balance the contact points on the two articular surfaces of the sensored insert. The sensored insert has a plurality of load sensors underlying the articular surfaces to measure load magnitude and position of load. In one embodiment, the surgeon can pin the tibial prosthetic component to the tibia at a single point. This will allow the tibial prosthetic component to rotate or pivot the tibial tray and sensored insert. Rotating the tibial tray and sensored insert can change the point of contact on the articular surfaces. The surgeon can use this technique to move the contact points closer to an optimum contact position or within a predetermined range on each articular surface. The amount of rotation to move the contact points is indicated in the tibial tray rotation box, the degree of parallelism of the contact points is depicted as a degree representing the CP rotation value 2610. Subsequent measurements of the alignment to the mechanical axis will factor in contact point rotation in the calculations of bone alignment. In the example, CP Rotation 2610 decreases and Tibial Rotation 2600 increases as the device is rotated but note that a line passing through the contact points is now more aligned with respect to the horizontal 2640 of the display (e.g., the values of 158A and 158B are closer to each other). In one embodiment, GUI 100 can indicate a predetermined area range and compare the actual contact points to the predetermined area range. The user would rotate the tibial tray and sensored insert until the contact points are within the predetermined region. Similarly, GUI 100 can indicate a predetermined load magnitude range and compare to the measurement of load magnitude on each articular surface. In one example contact points 158A and 158B are also not centered with respect to a vertical line 2630 on the GUI 100, the surgeon can rotate to a non-zero CP rotation value FF.F2 to get the contact points 158AA and 158B more symmetric with respect to a vertical 2630 through the center of implant 157.

Figure 27:
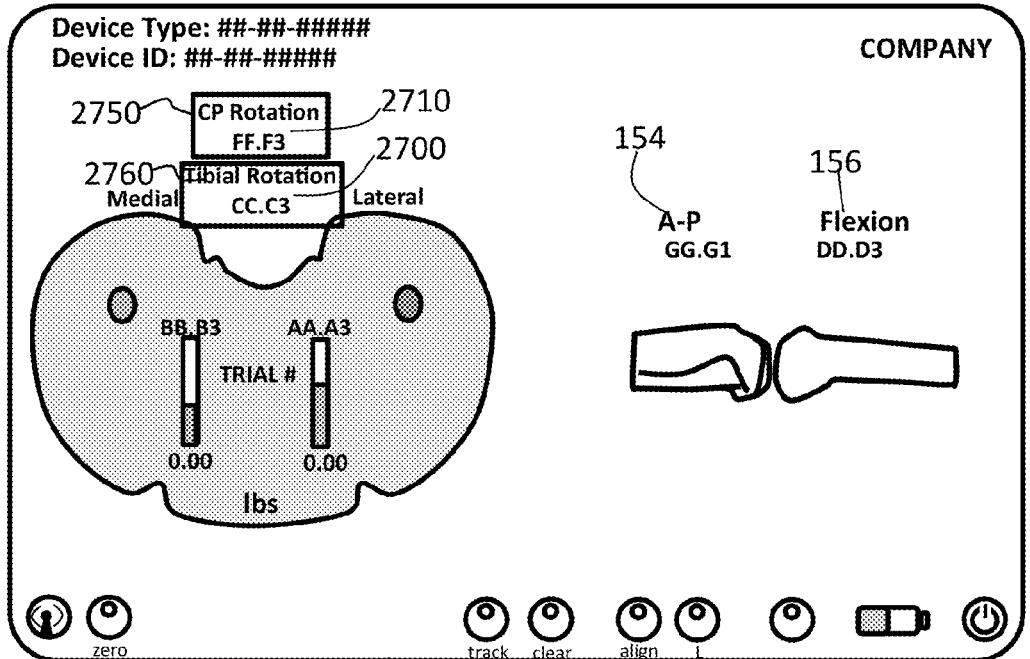

FIG. 27 illustrates the GUI 100 when the surgeon clicks on the CP rotation display to freeze the CP rotation value and the Tibia Rotation value in the software display. When the surgeon is satisfied with the location of the contact points he can click on the lettering "CP Rotation" on the GUI 100, and boxes 2750 and 2760 (indicating the values are fixed) will appear near the Tibial (tray) Rotation Value 2700 and the Cp Rotation Value 2710. The tibial (tray) rotation angle 2700 can be used for alignment. After this stage the alignment can begin, and the user can click on the align button.

Figure 28:
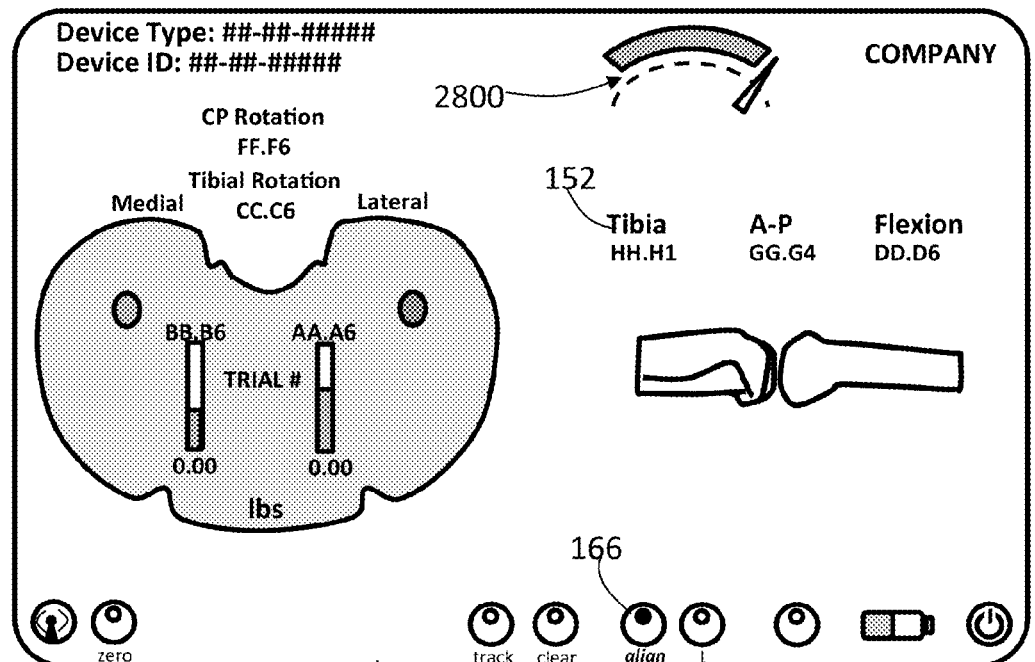

FIG. 28 illustrates the GUI 100 when the user (e.g. surgeon) clicks on the alignment button 166 to initiate a measurement of muscular-skeletal alignment. In the example, the leg is measured and compared to a mechanical axis with the prosthetic knee joint in place. The alignment workflow is started by indication on alignment button 166 when the "Align" lettering on button 166 turns red and a blue light on button 166 turns on. A Tibia Plateau Slope value 152 is displayed and an indicator dial 2800 is displayed. In the example, the proximal end of the tibia has been cut and the tibial prosthetic component is inserted and coupled to the tibia. The tibial plateau corresponds to the bone cut at the proximal end of the tibia. The tibial tray of the tibial prosthetic component couples to and takes on an angle of the bone cut on the proximal end of the tibia. Tibial Plateau Slope value 152 corresponds to the medial-lateral slope of the bone cut on the proximal end of the tibia.

A needle indicator dial 2800 moves as the anatomical feature (with device 157) inserted therein (e.g. knee joint) is rocked back and forth. Note that rotation is related to the values of y/x, while tilt is related to the values of y/z. The device is rocked back and forth until the Max-Gx value is obtained, which should correspond to the y about 0 if the internal (not displayed) tibia (tray) rotation is approximately zero. If the value is not zero at max A-P axis position, then there is tilt. As mentioned previously, any CP Rotation value can be taken into account for the calculation of Tibial Plateau Slope value 152. During alignment (referring to FIG. 26) the axis corresponding to the A-P of the device 157 is the vertical line 2630, while what is referred to as the Medial-Lateral (ML) line is related to the horizontal line 2640, and there is an axis perpendicular to both. Thus the rocking of the anatomical feature with the device 157 inserted, is essentially looking for the zenith of the arc of rotation, which should correspond to an ML line orientation that should be horizontal (about 0 degrees with respect to the horizontal on the GUI). If the angle is not zero, there is medial-lateral slope cut into the proximal end of the tibia that is measured and compared to the cut angle set that was previously set in tibial bone cutting jig. Thus, verification of the bone cut angle is achieved through quantitative measurement.

Figure 29:
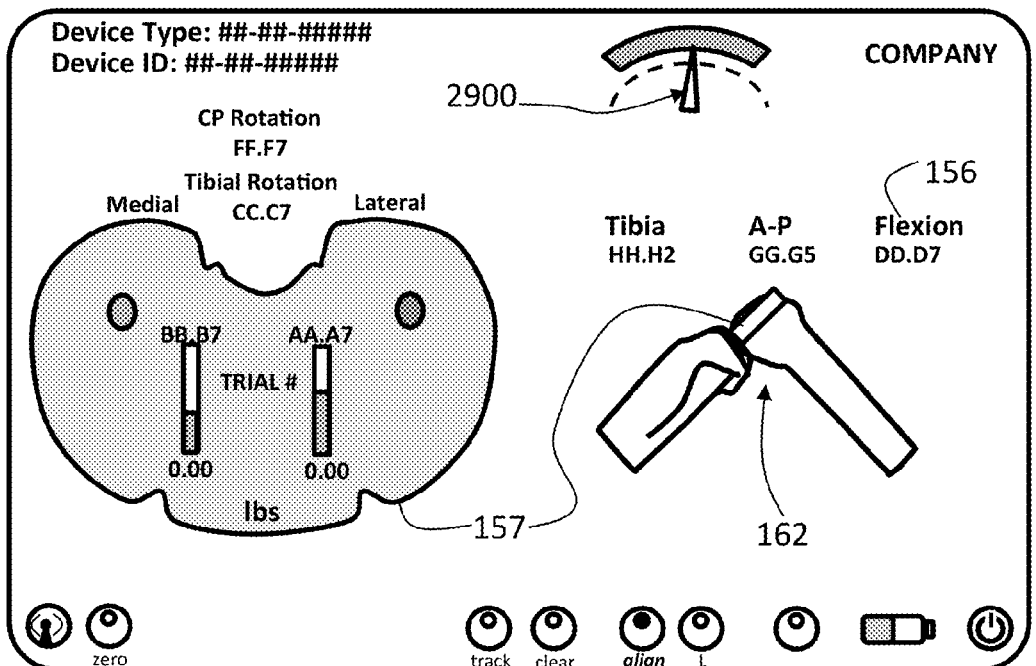

FIG. 29 illustrates GUI 100 feedback that is provided to the user when the leg is placed in flexion, for example 90 degrees (e.g., color of flexion angle text changes to yellow, indicator dial movement 2900, when the value is approached). Note that the value may be more than 90 degrees due to the A-P slope of the proximal end of tibia bone cut. In general, the leg is placed in flexion whereby the device 157 is oriented at a predetermined (chosen) angle for example a 45 degree angle from the surface of the OR table. Note that if the device 157 can be oriented at 45 degrees with respect to the plane of the OR table, the orientation of the A-P line and the normal to the A-P and M-L lines are both about 45 degrees or roughly equal in value with respect to gravity.

Figure 30:
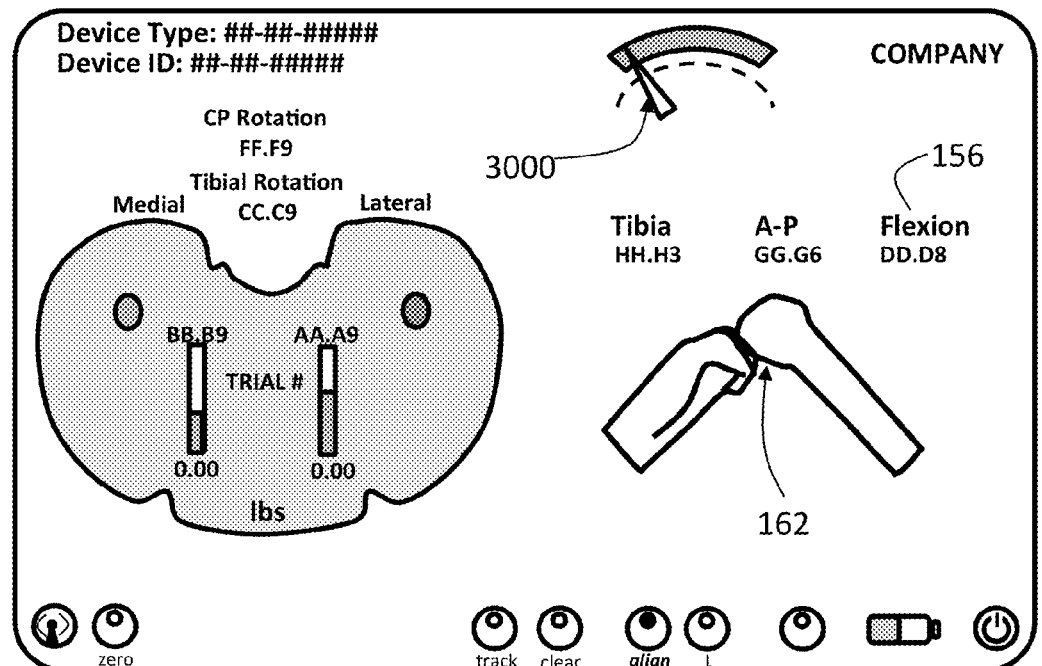

The knee in flexion is displayed 162 in the GUI 100. The amount the leg is in flexion is listed under Flexion 156 of GUI 100. Display allows the surgeon to rapidly assimilate the leg position at a glance. In one embodiment, the tibia is pivoted on a point of the mechanical axis. For example, the surgeon holds the heel down at the table with one hand allowing the heel to be a pivot point (see discussion above for FIGS. 9 and 10). With the other hand under the knee joint the surgeon moves the knee joint inward and outward (while pivoting about the heel contact. The patient remains in a fixed position during the movement. As the surgeon moves the knee joint in and out on the pivot point the indicator dial 2900 moves and follows the motion. A delayed response of the dial 2900 with the motion indicates that the motion is too fast, and also provides feedback as to the rotation angle. Data is being taken to determine the zenith values, which will determine the tilt values. Multiple rocking past and forth about zenith is done to take data points along each complete arc and then the points from each arc are used to determine the location of the zenith. As the surgeon rotates the knee joint and pivots on the heel the indicator dial 3000 (FIG. 30) also moves to the side of rotation. For example, FIG. 30 illustrates the case where the surgeon has pivoted the knee joint counterclockwise (as measured on the display). If during the rotation an error occurs, the sensor module can force the surgeon to start the flexion motion again. Similarly, if the heel inadvertently moves during motion, and the flexion values 156 moves away from the target, the indication of being close to the target position (e.g., yellow text angle) can disappear (e.g., change back to a non close indicator color such as white).

Figure 31:
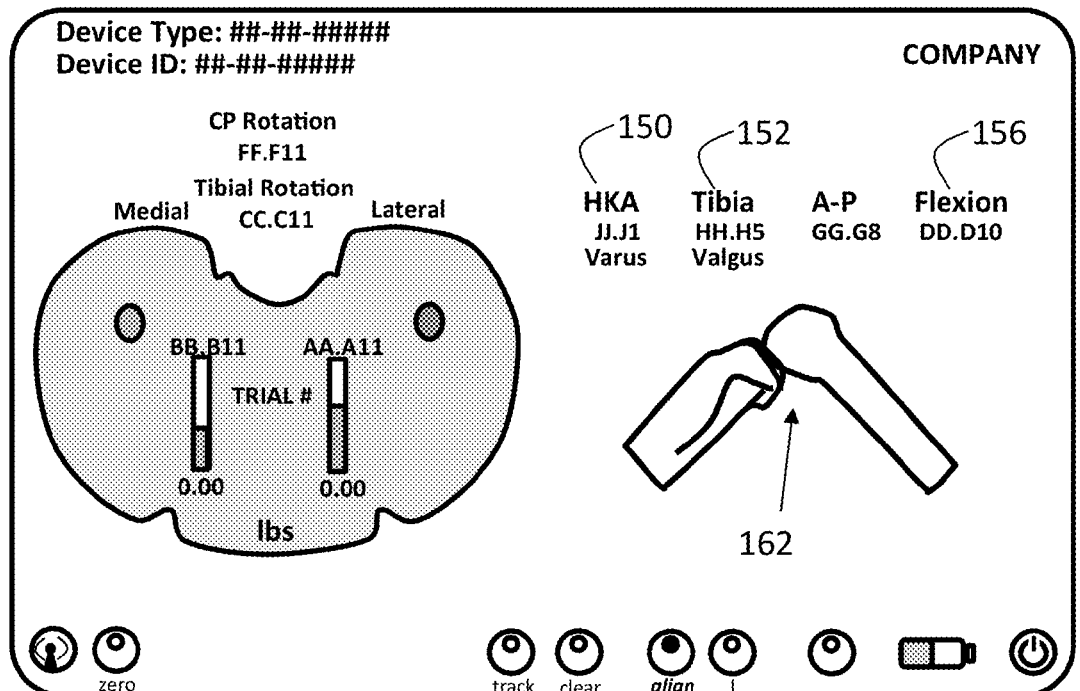

FIG. 31 illustrates the GUI 100 when the surgeon has gone back and forth a predetermined number of times while pivoting on the heel of the leg such that the conditions for measurement have been met. The Mechanical Axis (HKA 150) (also referred to as the load bearing axis) alignment number is now displayed and frozen, as is the Tibia Plateau Slope 152. The HKA or mechanical axis 150 of the display is a measure of the total offset of the femur and tibia to the mechanical axis. There is clinical evidence that indicates that misalignment of a prosthetic joint to the mechanical axis above a predetermined amount will result in joint performance loss and long-term reliability issues. Moreover, as prosthetic component design becomes more sophisticated surgeons can add predetermined slopes to the bone cuts to enhance performance. The system can be used to verify the angle of the bone cuts and the trial prosthesis. Thus, a measurement of the tibia alignment to the mechanical axis has been measured. GUI 100 will display an offset in degrees that is either varus or valgus to the mechanical axis.

Figure 32:
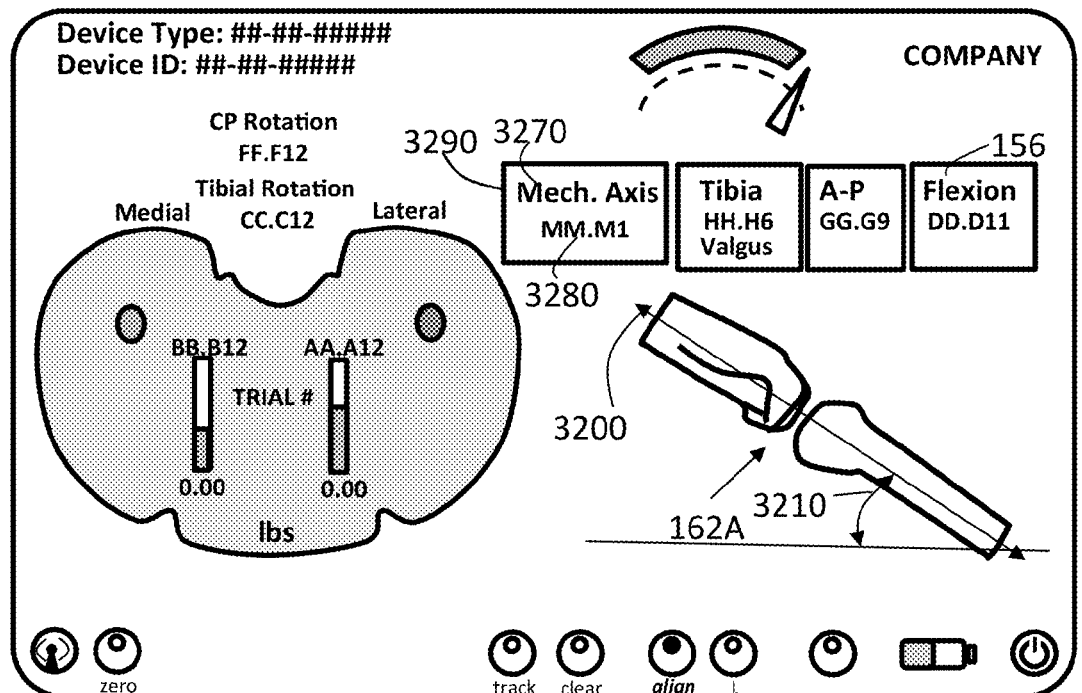

FIG. 32 illustrates the GUI 100 when the surgeon begins to measure an offset of the femur to the mechanical axis. In one embodiment, the leg is placed in full extension and lifted to pivot on the femoral head of the femur in the hip joint. The surgeon lifts the leg in full extension 3200 at an angle 3210 that places the sensored insert in the knee joint at approximately 45 degrees to the surface of the OR table. In one embodiment, mechanical axis value 150 disappears from GUI 100 as the femur offset is being measured.

Figure 33:
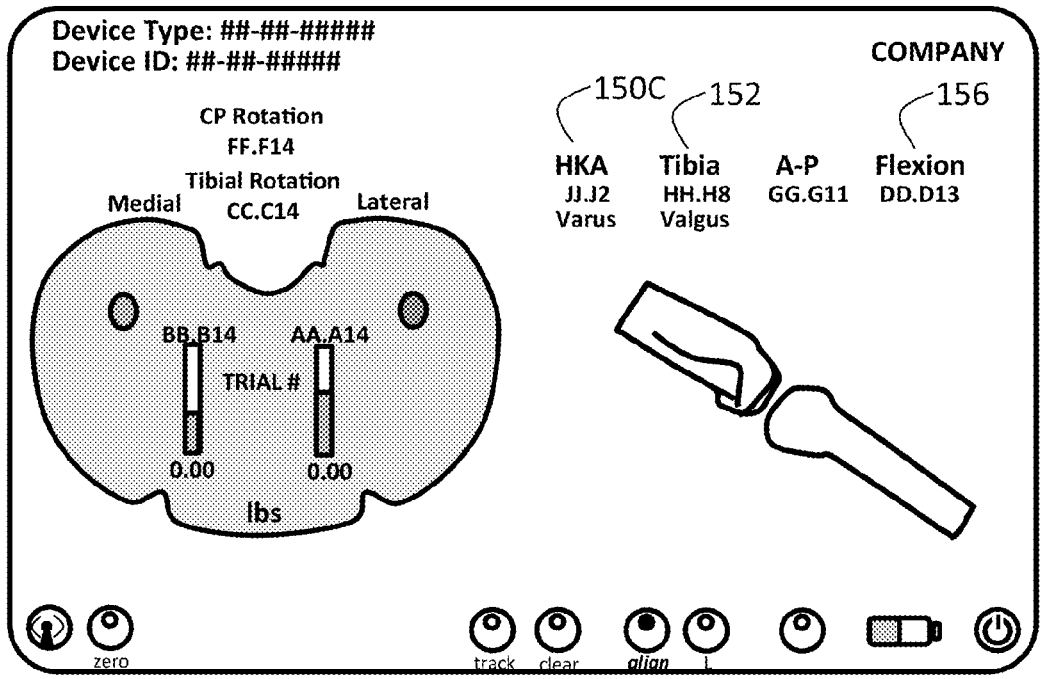

FIG. 33 illustrates that as the surgeon gets close to the target position, feedback is provided (e.g., the text of the flexion angle 156 changes, referred to as device color). For example if the target is −45 degrees the color of the text will change when the sensored insert angle approaches −45 degrees within +/− a few degrees in the knee joint. Thus, the femoral offset to the mechanical axis can be measured upon reaching the appropriate angle for the sensored insert (e.g., −45 degrees) with the leg in extension.

With the leg in extension (see FIG. 28) the knee joint is then rotated back and forth pivoting on the hip joint a predetermined number of times. Similar to the measure of the tibia offset, data points are measured over each arc created by the knee joint and the data points are used to determine a zenith or Max G of the arc. The position of the Max G of the arc of the knee joint is used to calculate the medial-lateral slope of the distal end of the femur surface. The femoral offset is measured in degrees and can be varus or valgus to the mechanical axis of the leg. GUI 100 displays the combined offsets of the tibia and femur to the mechanical axis. In one embodiment, the measured femur medial-lateral slope is subtracted from the tibia medial-lateral slope values to obtain an offset value 3280 that is displayed in mechanical axis 3270. Once a measured value average is obtained the color of the text in mechanical axis 3270 changes to match the text of the other indicators (e.g., A-P) and a box 3290 appears around the offset value 3280 in mechanical axis mechanical axis 3270. The angular accuracy obtained by at least one embodiment is on the order of 0.5 degrees for navigation and at least one embodiment can obtain greater than 0.1 degree accuracy.

Figure 34:
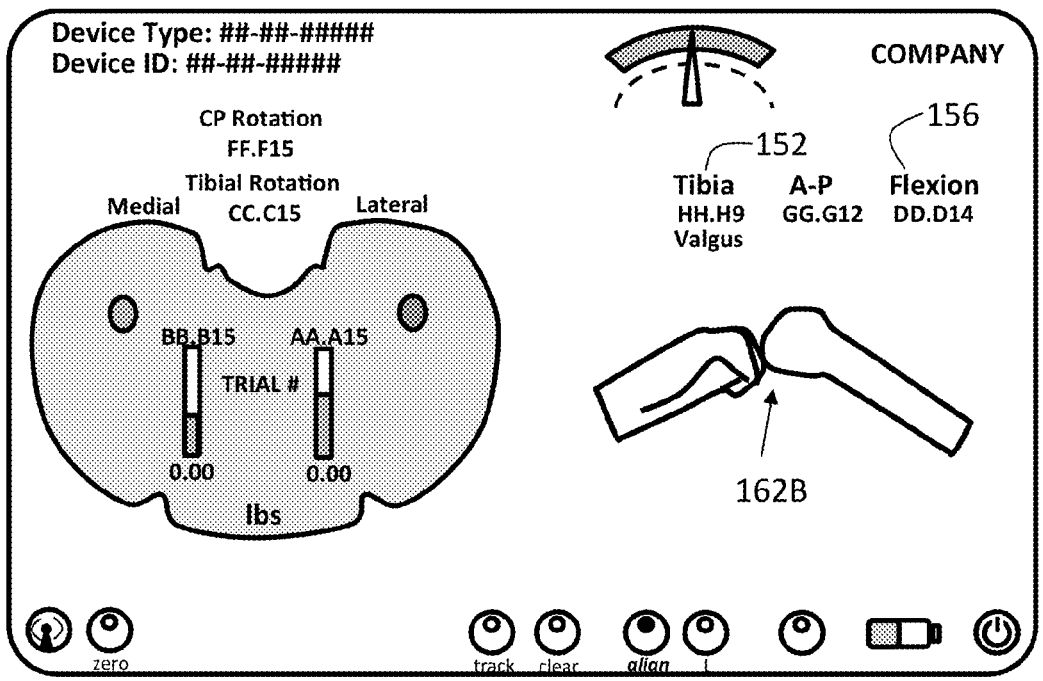

In FIG. 34, the GUI 100 displays when the surgeon repositions the leg to obtain a new target flexion angle value. In one embodiment, a HKA or mechanical axis value 150C disappears, while maintaining again the measured Tibia value 152. In this example the knee position 162B alignment target is a flexion angle 156 of 45 degrees. As the surgeon is approaching the target flexion (e.g., 45 degrees also referred to as a mid flexion target) feedback is provided, for example the flexion angle text 156 changes to a device color. If the surgeon has moved outside the target flexion value the indicator text color changes. When the surgeon is back within the target window about the third flexion target angle (e.g., 45 degrees), the text displays the angle in the device color.

The discussion above is for a non-limiting embodiment that discusses the alignment of a device (sensor) 157 placed into an implant. Note that the sensor 157 can also be placed into a cutting jig 3530. The cutting jig 3530 (FIG. 35) is coupled to the bone, as described below to define one or more bone cut angles. The device 157 can be used to align cutting jig 3530 to precisely cut bone angles relative to the mechanical axis. It is used similarly as described hereinabove to measure femur and tibia offset to the mechanical axis. The measurements can then be taken into account in aligning cutting jig 3530 to specific bone cuts. Thus, bone cuts can be made using quantitative measurements using a conventional bone cutting jig in conjunction with the system disclosed herein.

Figure 35:
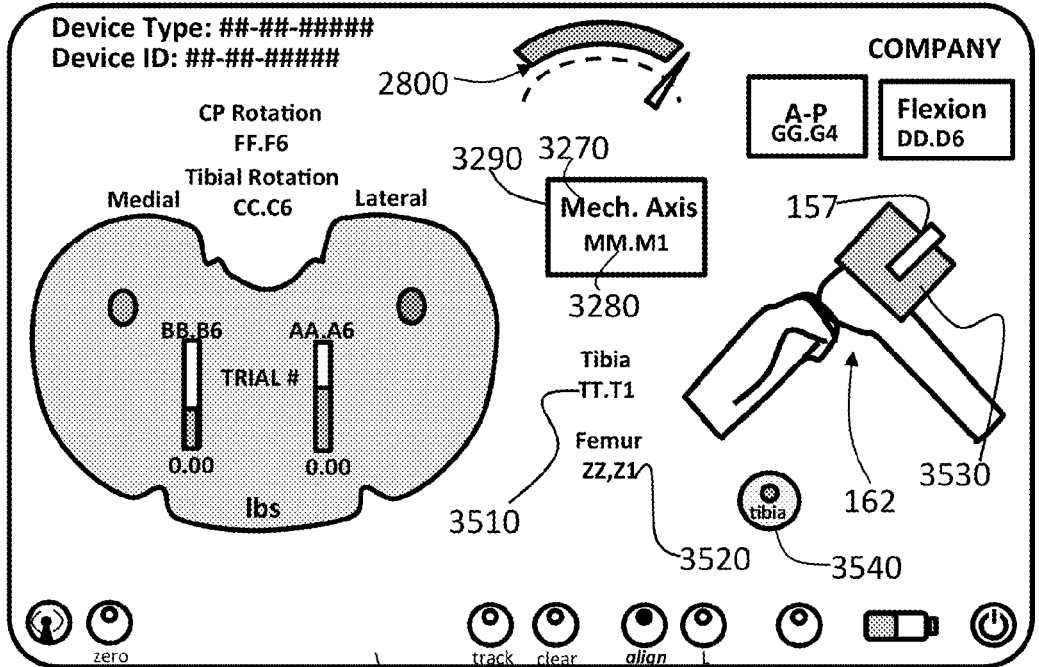

In one embodiment, device 157 is a sensored insert. A shim can be coupled to the sensored insert. The shim can have a tab extending from the shim body that couples into a cutting slot of cutting jig 3530. Alternate variations can also be used to affix the sensored insert and shim to the cutting jig 3530. Cutting jig 3530 is attached to a bone. FIG. 35 illustrates bone cutting jig 3530 coupled to the tibia of the leg. The sensored insert is referenced as disclosed above prior to coupling the sensored insert to bone jig 3530. For example, the device 157 can be zeroed to a plane of the operating table. Similarly, device 157 is zeroed to a plane perpendicular to the operating table. The leg is then placed in an approximate position of extension. The insert is coupled to a bone landmark or tool coupled to the leg. For example, the distal end of device 157 is held against and referenced to the tibial crest as disclosed above. In another fashion, the jig can be inserted in the knee with the attached sensor, and the pre-cut slope of the proximal tibia plateau can be referenced.

Once referenced, device 157 can be coupled to a cutting jig to measure alignment. Cutting jigs are typically coupled and aligned to a bone in a predetermined manner identified by the manufacturer of the jig. The jig can have a cutting slot for fitting a saw to cut the bone at a precise angle. The cutting slot of the cutting jig can be precisely moved to change the angle of the cut from a reference position of the jig. In one embodiment, cutting jig 3530 coupled to the tibia is referenced to make a cut with zero medial-lateral slope and zero anterior-posterior slope to the proximal end of the tibia. The cut can be a simple cut along a single plane or a compound bone cut across multiple planes. The shim that couples to the bone jig can be customized for fitting a specific jig. The manufacture of the shim has a substantially lower cost than device 157. This allows device 157 to be used for a wide variety of different jigs and prosthetic components without costly modification.

In one embodiment, the shim couples device 157 to bone cutting jig 3530 such that device 157 is in alignment to the cut to be made in the tibia. As mentioned previously, the device has been zeroed and referenced similar to the example when the sensored insert is installed in the knee joint to verify alignment and bone cuts. The process of measuring the alignment of the tibia relative to the mechanical axis and the femur relative to the mechanical axis is also similar to that disclosed above for the sensored insert in the knee joint. The leg is placed in flexion such that device 157 is at a 45 degree angle to the surface of the operating table. The heel of the leg is held against the operating table while device 157 is positioned. The heel is held at the position where device 157 is at a chosen angle, for example a 45 degree angle as a pivot point for the knee joint. The knee joint is rocked back and forth pivoting off of the heel. The ankle can be held to prevent movement in relation to the heel. The system measures points of the arc as the knee joint is rocked back and forth (see discussion with respect to FIG. 28). The knee joint is rocked back and forth a predetermined number of times. The system calculates the location of the Max-G point of the arc. The system then calculates the medial-lateral slope of the proximal end of the tibia from the location of the measured Max-G position relative to the Max-G position for the tibia aligned to the mechanical axis. The calculated medial-lateral slope corresponds to a varus or valgus offset or angle of the tibia relative to the mechanical axis. The surgeon utilizes the quantitative measurements to adjust bone cutting jig 3530 to set appropriate bone cut angles for A-P slope and M-L slope taking into account the patient anatomy and the specific prosthetic components being used. The tibial prosthetic component can be installed after the bone cut has been made and angles re-checked.

Figure 36:
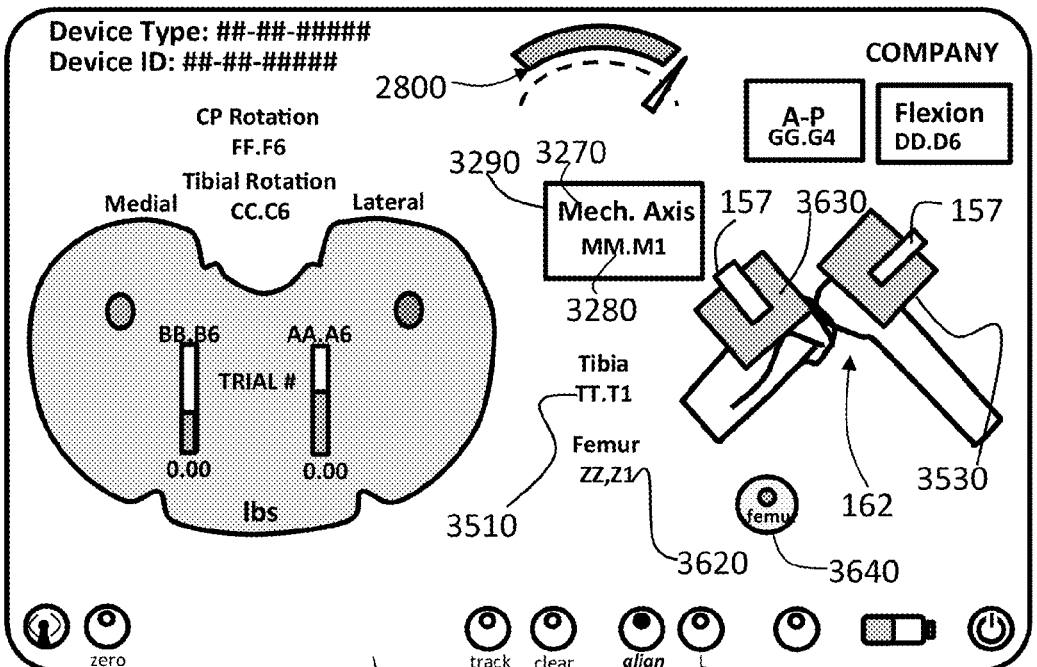

FIG. 36 illustrates two bone cutting jigs that are used on opposing bones (e.g. femur and tibia) of a muscular-skeletal joint. In the example, jig 3530 is coupled to a proximal end of the tibia and a jig 3630 is coupled to a distal end of a femur. Device 157 can be coupled to either cutting jig as disclosed above. Although disclosed hereinabove, the system provides the option of cutting the femur or the tibia first. The A-P slope can be captured. Note the process is similar to that described above, for example the 90 degree bent knee can now be rocked multiple times except the movement is to obtain a near zero value of the tibia angle 3510. When the user has a tibia angle close to zero the tibia select button 3540 is pressed to switch to the femur, and the jig on the tibia is locked in place. The process is then repeated for the femur jig 3630, see FIG. 36, where the femur select button is showing 3640, and the object is to zero the femur value 3610. Now the distal femur and proximal tibia can be cut.

Additionally the device can be placed on the tibia plateau of a cut distal face. The sensor can be pinched in place until the loading is even, and used to mark aligned drill holes to place a cutting jig.

As described above at least one embodiment can be used to make bone cuts. Herein we described a non-limiting example of an embodiment used to cut bones for installation of a prosthetic knee joint, although the embodiment is not limited to any particular joint or bone. The system can be used to make any bone cuts of the muscular-skeletal system. In this description the assumption is that a user has launched or re-launched the GUI as disclosed hereinabove. The GUI can provide feedback for zeroing the device. In at least one embodiment zeroing the device will include a flat (horizontal) orientation with respect to a surface (e.g., table), and a vertical orientation with respect to the surface of the table. Feedback may include a tone, and/or text on the GUI, for example the GUI may display the text "Please rotate the device 180 degrees and re-position it flat on the table—press the "Zero" button again."

Figure 37:
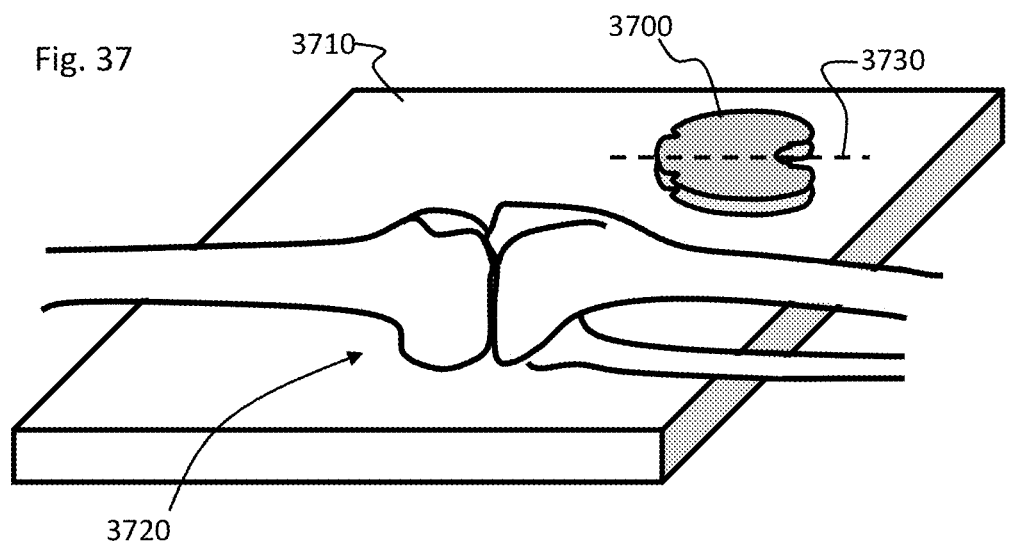
FIGS. 37-38 illustrates various device zeroing configurations.

FIG. 37 illustrates the bones of a knee 3720 and a device 3700 (e.g., insert sensor), where the device 3700 is placed flat 3730 (e.g., about parallel with the surface of the table) upon the table 3710 for zeroing. The feedback will then instruct the user to move the device 3700 into a vertical orientation for zeroing. For example the GUI may display the text "Please position the device vertically—press the "Zero" button again". Device 3700 includes a plurality of sensors for measuring a parameter of the muscular-skeletal system. Device 3700 can be in the form of a prosthetic component for trial or permanent measurements. In the example, device 3700 is a sensored insert having a plurality of load sensors underlying each articular surface and at least one 3 axis accelerometer for measuring position, rotation, and slope (or tilt).

Figure 38:
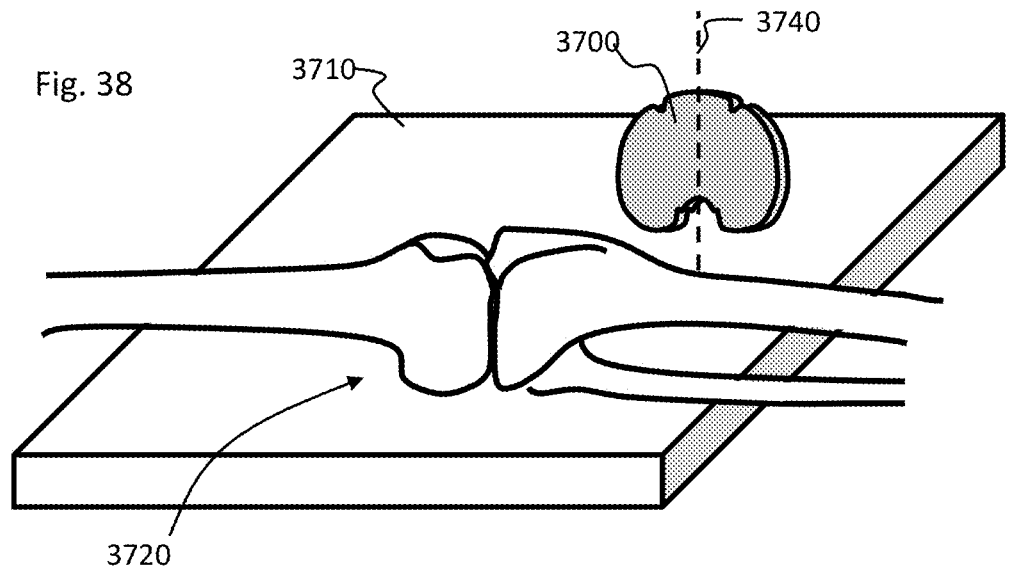

FIG. 38 illustrates the bones of a knee 3720 and a device 3700 (e.g., insert sensor), where the device 3700 is placed vertical 3740 (e.g., about perpendicular with the surface of the table) upon the table 3710 for zeroing. Once the device is zero'd the GUI can indicate that to the user (e.g., via text) and the device can be moved into the sterile field. Note that the zeroing can be done on a back table and transferred into the sterile field.

Once zero'd the device can capture the tibia in a reference position as described above. For example, the leg is positioned in extension or approximately in extension. The same technique as described above can be used to capture a bone landmark such as the tibia crest (FIG. 39). The device 3700 is placed on the tibia crest (note here the bone is showing, whereas in actual practice the device can be place upon the skin above the tibia) resulting in an axis 3910 running through the bisector axis (same axis as the vertical axis in FIG. 38 when zero'd vertically), where the axis 3910 is approximately perpendicular with respect to the plane of the surface of the table. Once the reference position is captured the GUI may provide feedback, for example the GUI may display the text "The Reference captured". Place the device in tibial prosthetic component tray". In extension, click A-P indicator to capture A-P slope".

Once the tibia crest is captured and the leg is in full extension, a cutting jig, either individually or in relation to each other can be coupled to the bones for cutting bone surfaces at precise angles for receiving prosthetic components. The process for finding alignment relative to the mechanical axis can similarly be identified as disclosed herein above only with device 3700 coupled to a bone cutting jig. The supports precut alignment of the cutting jigs to the mechanical axis. In the non-limiting knee example the proximal tibia and the distal femur can be cut. The cutting jig can be a commercial jig and need not be a specialized cutting jig when using the techniques described herein and an adapter to couple device 3700 to the commercial jig.

FIG. 40 illustrates at least one example of a method of connecting the device 3700 to the cutting jig 4200 via an adapter 4000. Adapter 4000 can be a low cost shim that couples to device 3700. In one embodiment, adapter 4000 has a tab or tongue that extends from the shim body. The tab of shim 4000 fits into a cutting slot of a cutting block. In the example, different adapters can be made for different cutting blocks allowing easy adaptability to various prosthetic component systems.

FIG. 41 illustrates the combined device 4100 including the adapter 4000 and the device 3700. In one embodiment, adapter 4000 and device 3700 have corresponding features that couples adapter 4000 to device 3700. In the example, the features allow adapter 4000 to be removed from device 3700. For example, adapter 4000 can have corresponding lips or flanges that couple together by interference or by connector.

Figure 42:
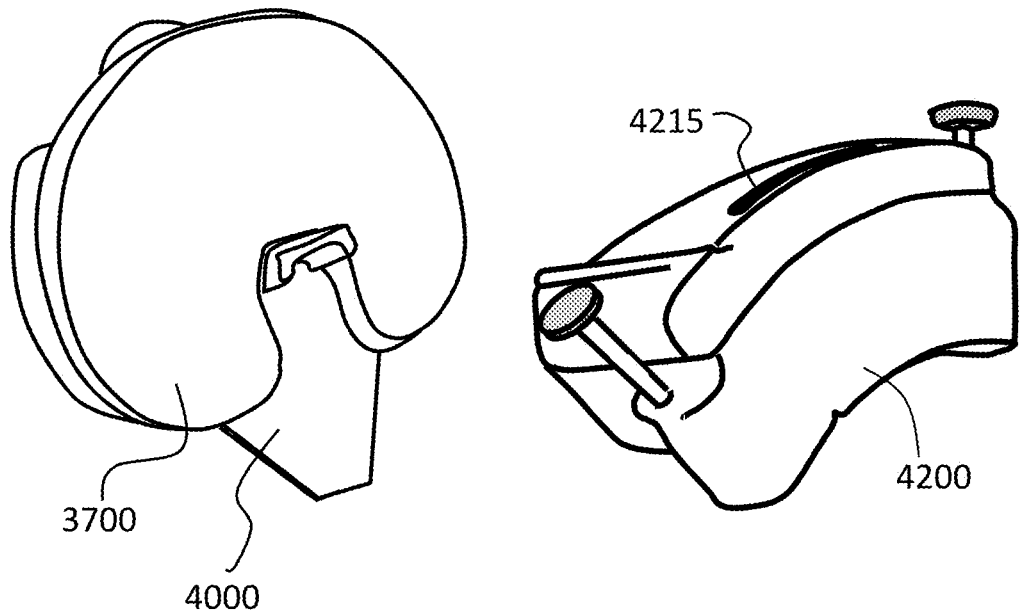
FIG. 42 illustrates a cutting jig and the associated adapter and sensor device.

FIG. 42 illustrates the insertion of the combined device 4100 into a cutting jig 4200 that is capable of accepting the combined device 4100, forming a cutting system 4300. The tab extending from the adapter 4000 fits into a receiving portion 4215 of cutting jig 4200. In the example, receiving portion 4215 of cutting jig 4200 is a cutting slot. The tab fits into the slot and is retained by cutting jig 4200. The tab also maintains an alignment of device 3700 to cutting jig 4200.

Figure 43:
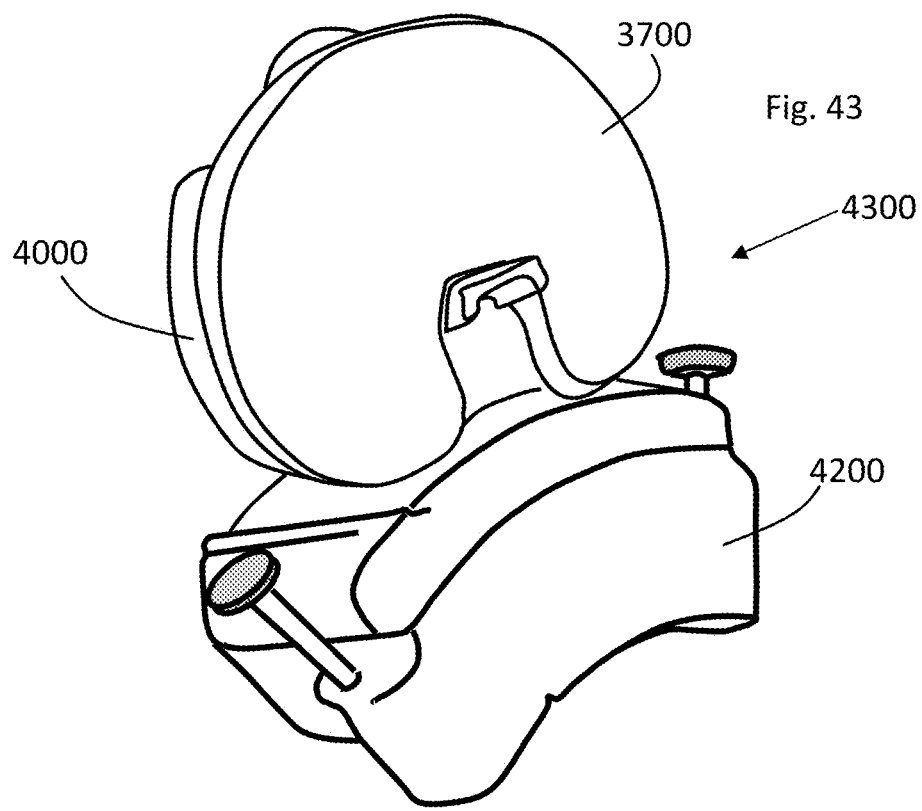
FIG. 43 illustrates an incorporated cutting jig system including the adapter and sensor device.

FIG. 43 illustrates the device 3700, adapter 4000 and cutting jig 4200 coupled together. The cutting system 4300 can now use the alignment information of the device 3700 to reference bone cuts. The tab of adapter 4000 is inserted into receiving portion 4215 of cutting jig 4200 to retain and align device 3700 to cutting jig 4200. In one embodiment, the posterior portion of device 3700 couples to a surface of bone cutting jig 4200.

Figure 44:
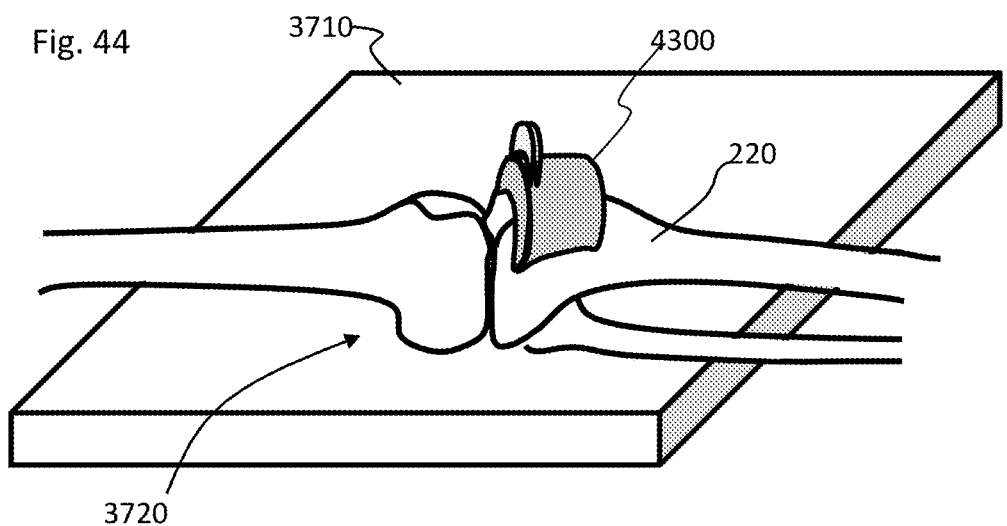
FIG. 44 illustrates the incorporated cutting jig system in a cutting position in an extended orthopedic system.

FIG. 44 illustrates the cutting system 4300 coupled to the extended leg. In the example, system 4300 is coupled to the tibia in preparation of cutting the proximal end of the tibia to receive a tibial prosthetic component. As mentioned previously, system 4300 was referenced to a tibia reference (e.g. tibial crest). System 4300 will measure the A-P slope of the bone cut with the leg in extension. The bone cutting jig can be adjusted to change or modify the A-P slope of the bone cut.

Figure 45:
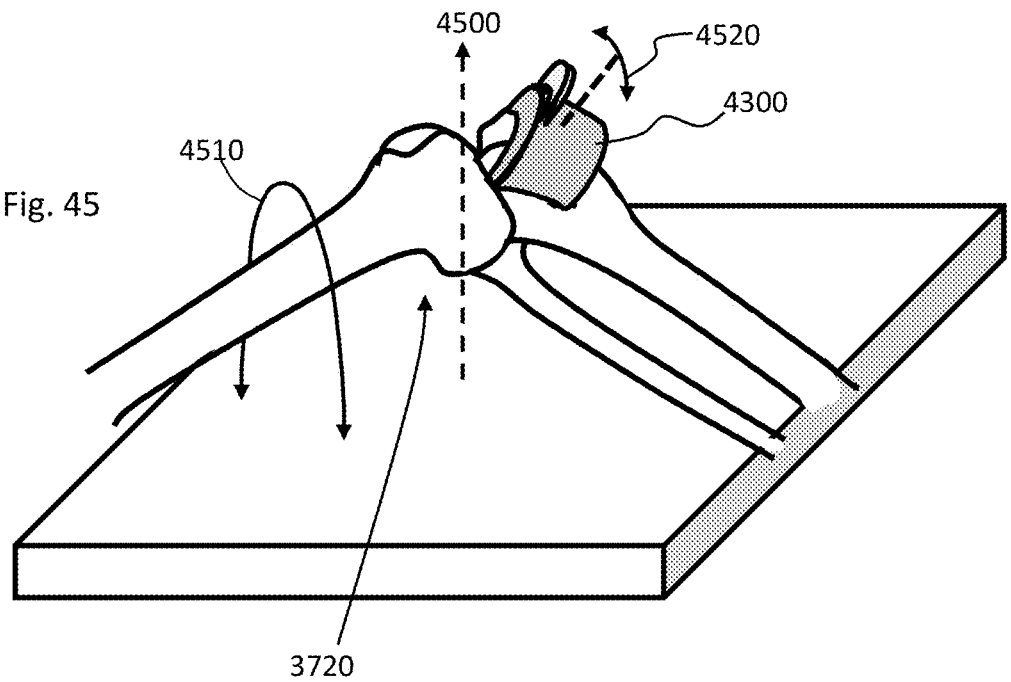
FIG. 45 illustrates the incorporated cutting jig system in a cutting position in a flexion orientation, changing vargus and valgus of the cutting jig.

The leg is then placed in flexion (FIG. 45) where a plane defined by the joint passes through about a vertical 4500. The position of flexion is selected where the accelerometer in system 4300 is at a 45 degree angle to the referenced surface (e.g. the operating table). The heel of the leg is held at the position achieving the 45 degree angle. As previously described above the joint 3720 can be rocked back and forth 4510 with the cutting system 4300 on the joint as it is rocked. The knee joint is pivoting on the heel of the leg. System 4300 measures the Max-G of the arc created by the rocking motion. The position of the Max-G in conjunction with the leg anatomy is converted to a measurement of the tibia offset.

Using the measurement information the cutting system 4300 can adjusted 4520 to change or modify the vargus and valgus tilt of the proximal end of the tibia. In one embodiment, system 4300 is fastened to bone with bone screws prior to measurements being taken. System 4300 can have an adjustable cutting slot thereon that can change or modify the A-P slope and M-L slope of the jig. In a second embodiment, system 4300 can be partially fastened to bone allowing the jig and thereby the cutting slot to be moved and pinned for the bone cut after the measurements have been taken and adjustments made. In a third embodiment, system 4300 can be temporarily fastened to the bone allowing the measurements to be made. The cutting jig can be adjusted after measurements have been made to cut the appropriate bone slopes. The cutting jig can then be fastened to bone prior to making bone cuts with a bone saw.

Figure 46:
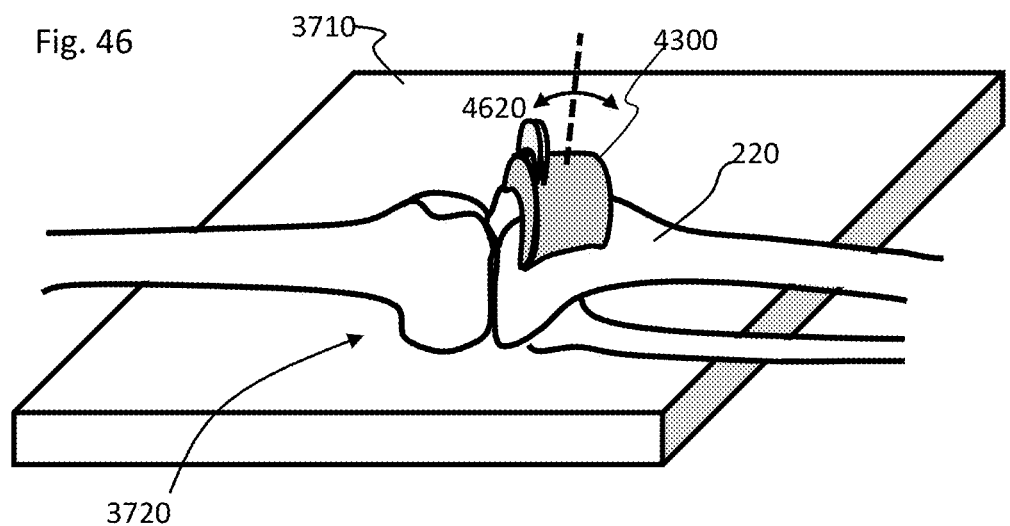
FIG. 46 illustrates the incorporated cutting jig system in a cutting position in an extension system, changing the A-P angle of the cutting jig.

As mentioned previously, since cutting system 4300 is referenced to the tibia reference an A-P slope can be obtained. For example FIG. 46 illustrates an extended joint where the cutting system 4300 cutting slot is moved 4620 to obtain a desired A-P slope. Note that the illustration in FIG. 46 shows cutting system 4300 on the tibia, however the same process as described above can be used on the femur. For example instead of the A-P slope one would obtain the distal-femur flexion angle.

Figure 47:
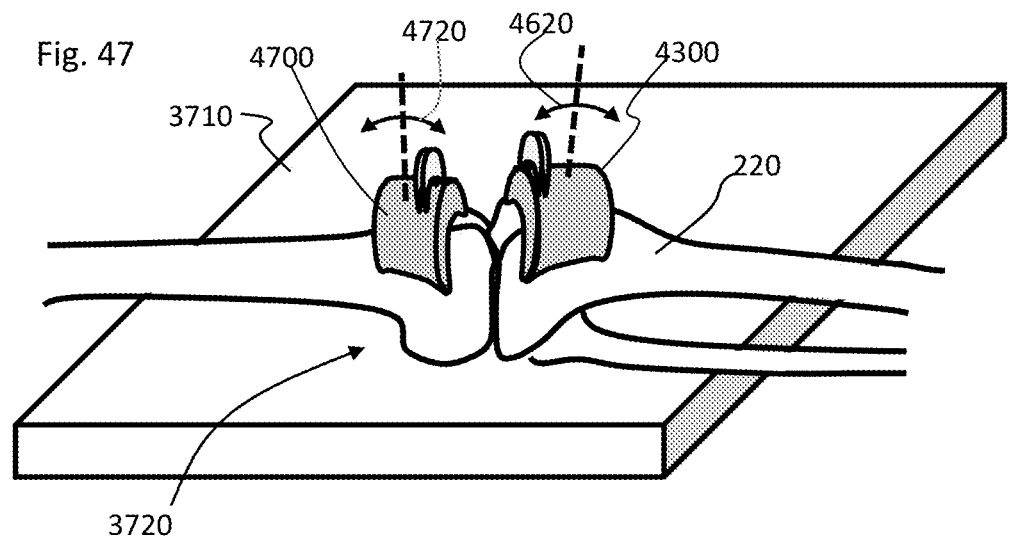
FIG. 47 illustrates two cutting jig systems being aligned.

FIG. 47 illustrates a bone cutting system 4700 on a distal end of a femur and a bone cutting system 4300 on a proximal end of the tibia. Moreover, measurements can be taken on the femur and the tibia to adjust cutting systems 4300 and 4700 to achieve parallel bone cuts. In one embodiment, the measurement device is moved from the system 4300 to system 4700 or vice versa to take measurements. The leg is placed in extension and verified by systems 4300 or 4700 depending upon which has the measuring device. For example, system 4300 is coupled to the proximal end of the tibia, the tibia measurement is selected on the GUI, the A-P slope of the proximal end of the tibia is measured, and the A-P slope of system 4300 is adjusted for cutting a predetermined A-P slope. Similarly, the measuring device can be transferred to system 4700. System 4700 is coupled to the distal end of the femur, the distal femur flexion (e.g. A-P slope) is measured at the distal end of the femur with the leg in extension, and the distal femur flexion is adjusted for cutting a predetermined A-P slope. In one embodiment, the bone cuts on the distal end of the femur and the proximal end of the tibia are set on the cutting blocks to be parallel to one another. This can be done very accurately because the bone cut settings use quantitative measurements from the measurement device referenced to the same plane.

The offset of the femur and tibia relative to the mechanical axis is also measured with systems 4300 and 4700. The femur and the tibia are respectively pivoted on the femoral head and the heel of the leg as disclosed herein. Data points are taken over several arcs as the knee joint is rocked back and forth a predetermined number of times. The Max-G point is located for the tibia pivoting on the heel and a varus-valgus offset is calculated. Similarly, the Max-G point is located for the femur pivoting on the femoral head of the femur and a varus-valgus offset is calculated. The information can be used to adjust the medial-lateral slope of the bone cut for the distal end of the femur and the proximal end of the tibia.

Thus, two cutting systems 4300 and 4700 can be used to get the desired distal femur flexion angle 4720 for the femur cutting system 4700 and the desired A-P angle 4620 for the tibia cutting system 4300, while orienting the cutting systems 4300 and 4700 so that they are parallel. Furthermore, systems 4300 and 4700 can measure the vargus/valgus tilt relative to the mechanical axis for the femur and tibia. The surgeon can use the measurement data from systems 4300 and 4700 to set the medial-lateral bone cuts on respectively the proximal tibia and distal femur. Note that as described above the vargus/valgus are measured with respect to the mechanical axis, where the mechanical axis is not the anatomical. The cutting systems 4300 and 4700 are coupled to the distal femur and the proximal tibia with the adjusted cutting slots based on quantitative measurements. A bone cutting saw is then used to but the femur and tibia. Note that both cutting systems 4300 and 4700 can be aligned with regards to any axis. In the embodiment described both cutting systems 4300 and 4700 were aligned to the tibia crest, thus ultimately to an axis of the tibia, however one could choose a femur axis to reference as well.

In addition to making initial cuts one can use the system to make additional cuts. For example the lateral femoral condyle can roll back on the tibia plateau causing unwanted lifting on the lateral side thereby placing all or most of the loading on the medial condyle as the knee is placed in flexion. The cutting jig is typically placed back on the distal femur, which already has a first cut. Occasionally, a second cut is made to adjust the angle of the femoral insert/component by cutting the posterior condials of the distal femur. The second cut is made by a special cutting jig that has some cut rotation built into the cut to compensate for the lift off in flexion. At least one embodiment can be used to increase the accuracy of the second cut. For example a femoral rotation guide can be placed upon the first cut with a device inserted to orient a cutting jig optimally for the second cut.

Figure 48:
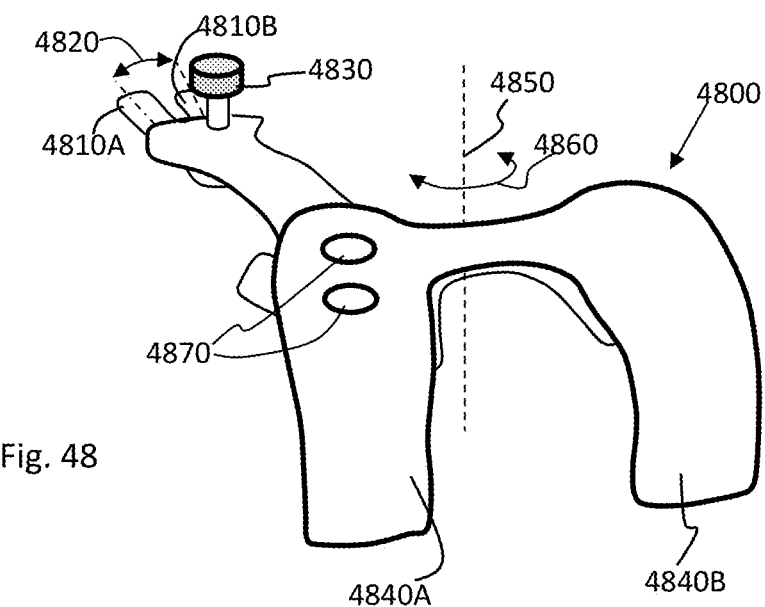
FIG. 48 illustrates a femur rotation guide.

FIG. 48 illustrates a femoral rotation guide 4800 where two condial surfaces 4840A and 4840B can pivot 4860 about an axis 4850 when pinchers 4810A and 4810B are squeezed or extended away from each other 4820. The condyle surfaces 4840A and 4840B are placed upon the cut condyles of the distal femur, and attached to the posterior uncut condyles of the femur. Note that the femoral rotation guide 4800 can be inserted with the patella reduced to provide realistic loading, and information regarding patellar tracking while rotational adjustments are made. At least one reference hole 4870 is available so that once the correct orientation is obtained. Reference holes for the cutting jig can be drilled into the bone. The femoral rotation guide 4800 can be removed and a cutting jig placed on the bone to be cut at an optimal rotation that supports both condyles contacting each articular surface over a range of motion of the knee joint. The cutting jig is lined up with the reference holes and screws inserted therein to fasten the device down.

Figure 49:
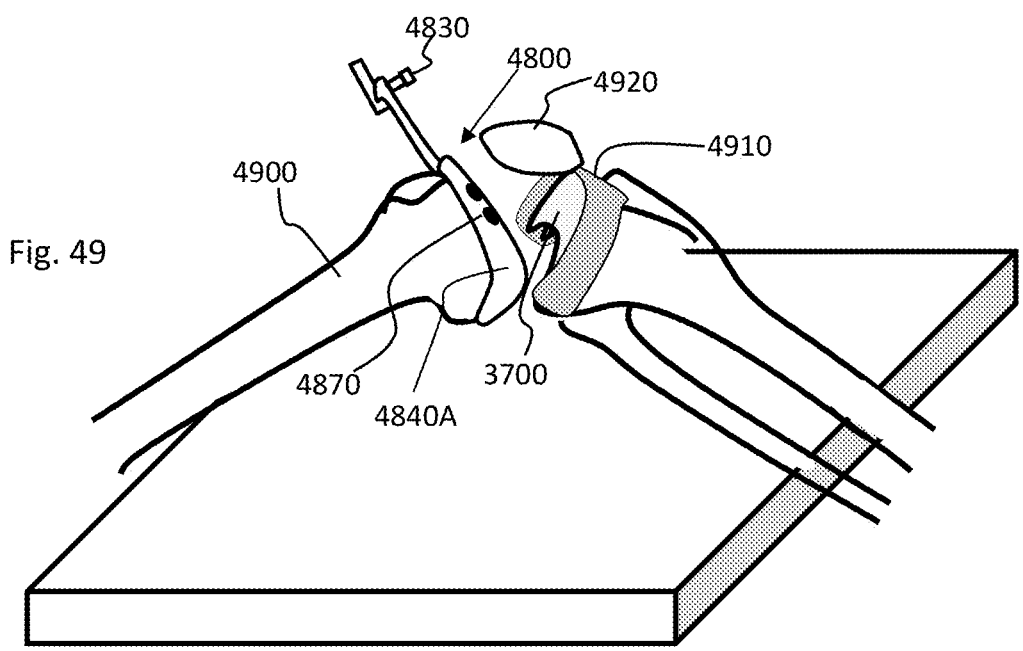
FIG. 49 illustrates using the femur rotation guide to adjust condial orientation.

FIG. 49 illustrates the femoral rotation guide 4800 attached to the distal end of the femur 4900, with the device 3700 inserted into a tibial tray 4910 or placed on the tibia plateau cut. The assembled components allow the leg to be moved through the range of motion. It is important to note, that the patella 4920 is moved in-place and the loading observed, rotating the knee joint to determine if condyle surfaces 4840A and 4840B are loading device 3700 over the range of motion (e.g., load sensor tibial insert). Note that FIG. 49 shows the system in separated view however when measuring the loads the condyle surfaces 4840A and 4840B will be in contact with device 3700. In one embodiment, after the proximal tibia and distal femur are cut, the leg is taken into extension. By knowing that the condylar geometry of the jig is the same as the distal femur, and the tibial sensor has the same geometry as the tibial component, the knee is extended and rotation of the femoral and tibial jigs can optimize implant congruency in extension, then soft tissue balancing can be performed to balance the "extension gap". The leg is now placed in flexion and pinchers 4810A and 4810B are squeezed together such that posterior femoral condyles 4840A and 4840B shift, translate or rotate to engage the condyles of the corresponding Tibial articular surface. The loading can be viewed on the GUI. When the loading on both articular surfaces of device 3700 are at an appropriate level or within a predetermined load range then dial 4830 is used to lock the pinchers so that the rotation 4860 is locked, and AP translation defined. Reference holes 4870 can then be drilled for subsequently mounting the cutting jig. Thus in summary, the pinchers 4810A and 4810B are pinched 4820 resulting in rotation 4860 of the condyle surfaces 4840A and 4840B thereby changing the loading measured by the device 3700. The angular orientation of the femoral rotation guide 4800 is locked and the reference hole drilled when a correct loading over the range of motion has been found. This process can be performed having all the muscular-skeletal joint anatomy in-place for correct kinetic loading. The cutting jig can then be aligned with the drilled reference holes and used to make the chamfer cuts and A-P cuts. Note that in this embodiment the femoral rotation guide can be a disposable system, and used to measure loading with the patella in place moving the leg in flexion and/or extension.

At least one embodiment is directed to a novel sensor system that incorporates positional sensing, load sensing, RF communications, powering and telemetry in a footprint of a tibial trial. This footprint is miniaturized to allow incorporation of the trial insert into other instruments that are utilized during a knee procedure such as gap balancers, distractors, and cutting jigs or can be molded to fit into any orthopedic system (e.g., knee system). The sensor system can also be placed in the tibial prosthetic component or the femoral prosthetic component. Furthermore, the design is not limited to measurement and alignment of the knee but can be used for hip, spine, ankle, shoulder, elbow, hand, wrist, foot, bone, and the muscular-skeletal system. Note that the sensors used in the sensor system are not limited to any particular type of sensor for example the sensor(s) can be capacitive, ultrasonic, film sensing, accelerometers, inclinometers, gyroscopes, acoustic, and electromagnetic.

At least one embodiment is also directed to a sensor system that communicates intra-operatively with real time data to a GUI that can be interpreted by the surgeon. This GUI can represent data from the sensors, can be voice activated and controlled, can integrate other data for display such as IR/US navigation systems for incorporated data points. Can record surgical footage with time stamped sensor data, can incorporate data related to the patients pre-op/intra-op/and post-op data. Implant data can be captured, which can be sent to a cloud computing system for access. At least one embodiment is directed to a sensored system composed of a trial insert that: can be used as a standard trial with no utilization of the electronics; can be utilized prior to cutting the bone to give angular/positional information of proposed cut angles; can be utilized after the cuttings jigs are attached to the femur and tibia to confirm appropriated angular positioning for the cut; can be utilized after the bony cuts have been made to check the accuracy of the angular cuts; can obtain a plane (such as the tibial crest) which the sensors can now reference to, to provide an angular number for interpretation to reference to before or after a cut is made; can incorporate other data points from other instruments (IR/US/Magnetic) on the GUI to incorporate information for interpretation; can incorporate angular information and load information with the knee implant trials in, which can allow the surgeon to refine the angular cuts and/or soft tissue balance, and for implant position and rotation real time to optimize the leg alignment as defined by the surgeon; can give real time data as to how angular geometry of the bony cuts/angles or the implant geometry affects soft tissue balance/loads and implant kinetic function; can give real time data as to how the soft tissue tension affects the overall mechanical alignment of the leg, and the implant kinetic function; can give real time data as to how adjustments to the bony angles and soft tissue tension affect each other in a dynamic function and affect collectively or independently the kinetic knee function; can be used with a trial implant system or a final implant system prior to closing the joint; can utilize a reference angle/plane that can be changed intra-operatively at the discretion of the surgeon; can give information related to implant congruency, alignment and soft tissue balance with thicker trial inserts, and for angular insert change; and can utilize incorporation of pre-operative scans such as x-rays, CT scans, MRI's into the GUI to reference intra-op planes and angles to. The Tibial and or Femoral cuts can be made first, then the Secondary femoral or Tibial cut can be made by knowing the angular reference of the interposed cutting jig to obtain equal extension gaps and flexion gaps. It allows distance gap measurements to incorporated soft tissue tension in multiple knee angles.

In addition to utilizing the sensor 3700 on the tibia crest 427, at least one embodiment 5000 (e.g., reference position tool), FIG. 50, utilizes a sensor 3700 on a tibial alignment device/tool 5010 to obtain the alignment information discussed herein with reference to FIGS. 4 and 39, where the alignment device 5010 and the sensor 3700 move as one as did the sensor 425 on the tibial crest 427 in FIG. 4. For example the tool 5010 (with sensor 3700 attached) is rotated back and forth in the same manner as the device 3700 on the tibial crest to obtain alignment information as in the discussion with reference to FIGS. 4 and 39. In this particular embodiment the sensor 3700 and alignment device 5010 move together, where the alignment device 5010 is positioned so that one end 5025A is approximately aligned 5010A with the proximal end 5020 of the tibia. The opposite end 5025B of the alignment device 5010 is approximately aligned with the distal end 5010B of the tibia 5030.

FIG. 51 illustrates a different view of the device shown in FIG. 50. The alignment device 5010 is extendable so that the ends 5010A and 5010B are moveable to fit any leg or the tool/alignment device 5010 can comprise more than one tool having several different lengths. At least one embodiment is adjustable to any length needed for example FIG. 51 illustrates an adjustable 5040 alignment device 5010. For example the section 5010 D can be attached to a slightly smaller bar 5010E that slides into a slightly large similarly shaped channel 5010F. The alignment device 5010 can be manufactured out of many different types of medical grade material (e.g., stainless steel, bio-compatible plastic). The alignment device 5010 can include an arm 5025 that contacts with the relative positions 5010B and 5010A where the arm 5025 extends from the body 5012. Note that the sensored device 3700 can be a prosthetic component.

At least one embodiment is directed to a muscular-skeletal alignment system 5000, that includes: a sensored device 3700 including at least one 3-axis accelerometer for measuring position, rotation, and slope; a remote system 5090, coupled to the device (e.g., wired or wirelessly 5095) for receiving position, rotation, or slope data; and a tool (e.g., alignment device 5010) configured to couple to the muscular-skeletal system where the tool is configured to be positioned to generate a reference with the sensored device 3700 coupled thereto. The tool/alignment device 5010 can include a tab 5031 so that the sensored device 3700 can be inserted onto the tool/alignment device 5010 and the sensored device 3700 can include a slot to accept the tab 5031.

Figure 91:
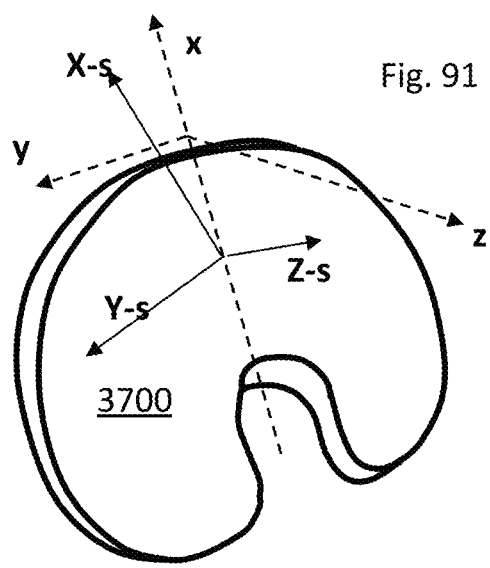
FIG. 91 illustrates axes associated with a sensor and rotations.

FIG. 91 illustrates one possible configuration of axes with sensored device 3700, where the initial orientation of the sensored device 3700 lies in the x-y plane, and the z-axis is normal to the x-y axis in accordance with the right-hand rule. For example where the body axes of the sensored device 3700 (x–s, y–s, z–s) initially are aligned with the reference axes (x, y, z). When the sensored device is then moved out of alignment with the reference axes (x, y, z) the orientation of the sensored device body axes (x–s, y–s, and z–s, can be projected onto the reference axes (x, y, and z) to obtain Dx, Dy, and Dz. These in turn can be used to define tray rotation, varus, valgus, flexion and slope. For example tray rotation can be defined as arctan(Dy/Dx), Varus and Valgus can be defined as arctan(Dy/Dz), and Flexion and Slope can be defined as arctan(Dz/Dx.).

Figure 92:
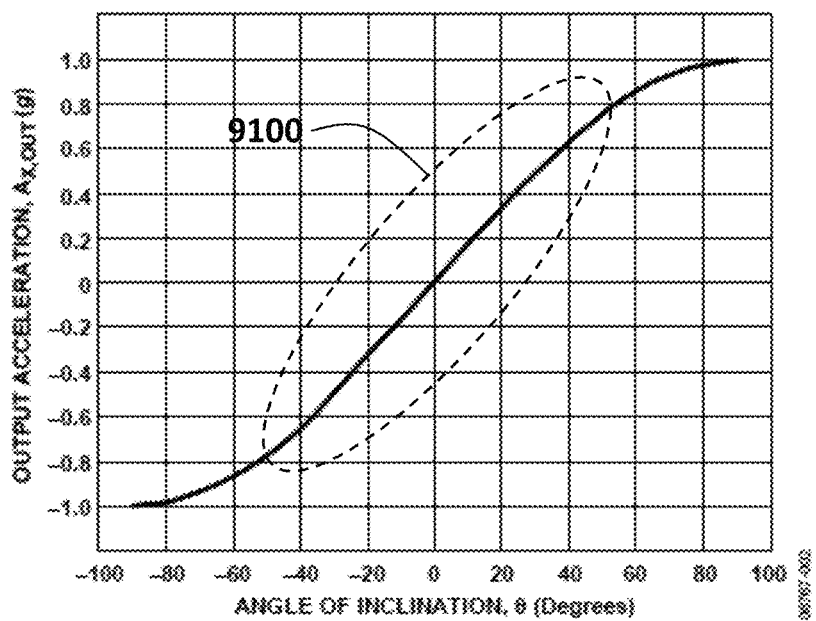
FIG. 92 illustrates a plot of the acceleration in the x direction versus angle of inclination of a sensor.

FIG. 92 illustrates a plot of the x-acceleration value (e.g., obtained by an accelerometer) versus angle of inclination e. As can be seen there is a region of linearity 9100, valid within a range of acceleration (e.g., −0.8 to 0.8 g) and angle of inclination (−45 degrees to +45 degrees). The angle of inclination can be defined as the inverse tangent of the ratio of (axout/ayout) or the ratio of the x acceleration value to the y acceleration value.

FIG. 93 illustrates a bent leg (sometimes referred to as a bent knee), with a sensor 9315 oriented at an angle, for example 45 degrees with respect to axis of rotation 9370A. Note other references can be used to define the angles of sensors. The knee/leg can be defined by the femur axis 9310A and 9310B, and tibia axis 9320A and 9320B. The knee can be rotated about the hip center 9330 and the "virtual" pivot point 9340 to obtain the mechanical axis 9300. Intersection of the two planes 9380 and 9390 defines the axis of rotation, which is along the load bearing, mechanical axis 9300. Plane 9380 is defined by femur axis 9310B and tibia axis 9320B, plane 9390 is defined by femur axis 9310A and tibia axis 9320A. The femur axis (9310A and 9310B) is offset 9360 with respect to the hip center 9330. The rotation moves the knee middle 9371 from 9370A to 9370B equivalent to the plane 9390 rotating to position 9380. One of the pivot points of the leg is the heel 9345, while the femur axis (9320 A and 9320B) passes through the center of the ankle 9350A and 9350B respectively to the "Virtual Pivot" 9340 that falls in line with the Heel 9345 and Hip Center 9330, defining the Axis of Rotation 9300. Note that the virtual pivot 9340 can lie above or below the plane 9342 (e.g. table).

To obtain the mechanical axis (MA) the Tibia-V is obtained by rotation on hip center 9330 and heel 9345 and capturing the a y/z value at the maximum x-value (e.g., maximum of the arc), as measured by the sensor 9315. The distal Femur-V value is obtained by lifting the leg in extension to a position where a sensor in the knee is upside down but still at 45 degrees, and rotating on the hip center 9330 to capture a new y/z value at the maximum x value as measured by the sensor 9315. Then the Mechanical axis can be defined as MA=(Tibia-V)–(Distal Femur-V).

FIGS. 94A and 94B illustrate two positions that can be used to average x and y positions to minimize error in the x-y reference plane. For example, a sensor 3700 can lie on a table 9400 and be rotated (from FIG. 94A to 94B). FIG. 95 illustrates a vertical position (of sensor 3700 x–s axis with table 9400) that can be used to average y again to minimize errors (e.g., internal assembly position of the accelerometer) and to average z.

Thus as discussed, one can calculate alignment to the mechanical axis by rotating back and forth on the pivot points. Note that the sampling rate of the sensor can vary for example a sample rate at 15 times/second when getting data points on the arc can be used. As discussed depending on the position of the max X (maximum of the arc) one can identify the tilt (Y/Z) of the bone cut (medial/lateral) which corresponds to the Varus/Valgus of the bone to the mechanical axis. Note that rotation back and forth can continue until one get measurements that are within a ½ degree of the average.

Figure 90:
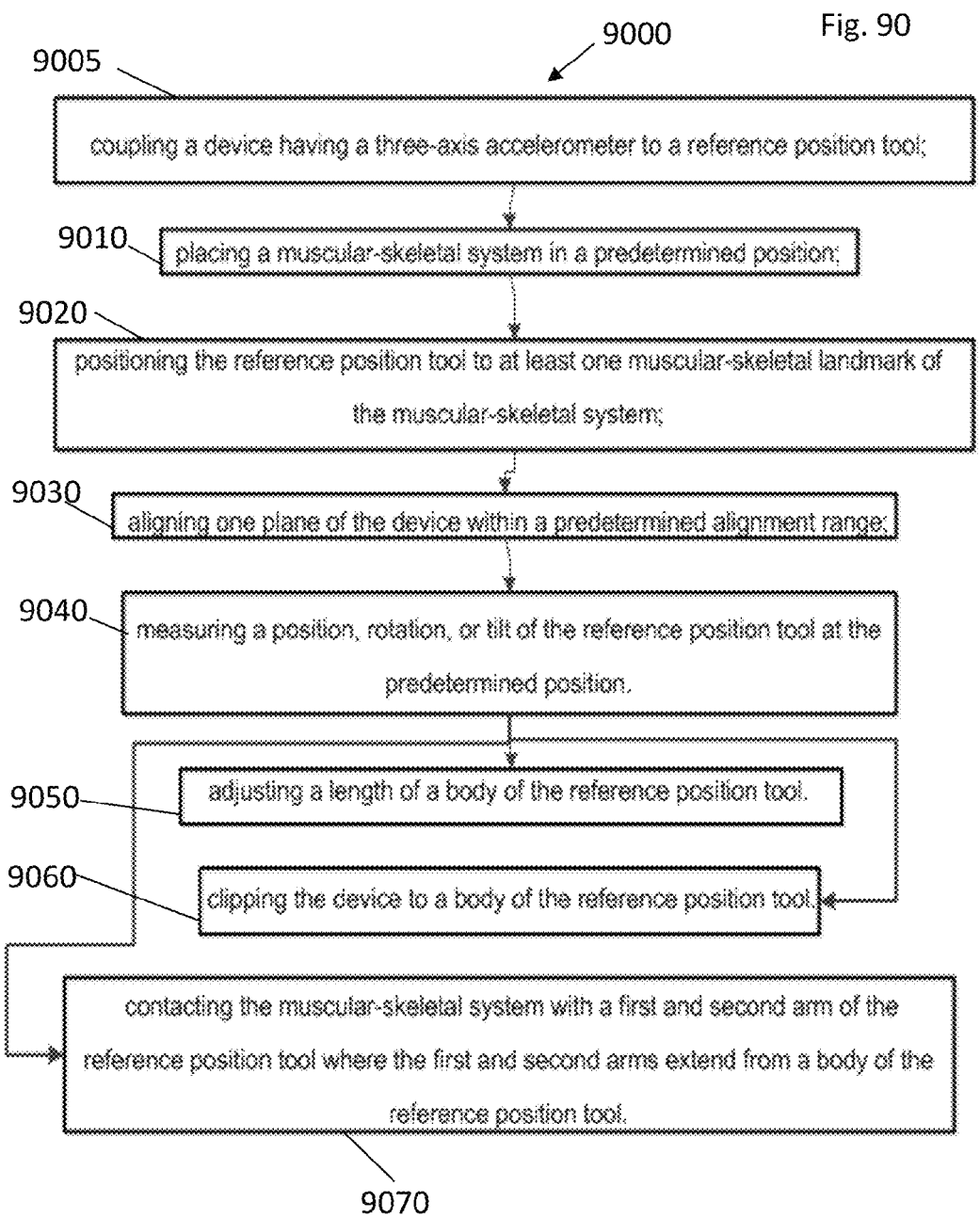
FIG. 90 illustrates a method of generating a reference position.

FIG. 90 illustrates at least one embodiment that is directed to a method 9000 of generating a reference position comprising the steps of: 9005 coupling a device 3070 having a three-axis accelerometer to a reference position tool 5010; 9010 placing a muscular-skeletal system in a predetermined position; 9020 positioning the reference position tool 5010 to at least one muscular-skeletal landmark of the muscular-skeletal system; 9030 aligning one plane (e.g., 5010A or 5010B) of the device within a predetermined alignment range; and 9040 measuring a position, rotation, or tilt of the reference position tool at the predetermined position. A further embodiment includes a step 9050 of adjusting a length (e.g., 5040) of a body of the reference position tool. A further embodiment includes 9060 clipping the device to a body of the reference position tool. A further embodiment includes a step 9070 of contacting the muscular-skeletal system with a first and second arm of the reference position tool where the first and second arms extend from a body of the reference position tool.

Note that the non-limiting description describing aspects of the invention for use in a total knee replacement (TKA) surgery, the invention is not limited to TKA but can be used in orthopedic surgery in general or for any joint repair, spine surgery, bone, or portions of the muscular-skeletal system that incorporates bony cuts and soft tissue balance for an optimized outcome, with or without implants.

Additional Embodiments

Additional non-limiting examples of embodiments will be discussed herein.

Figure 53:
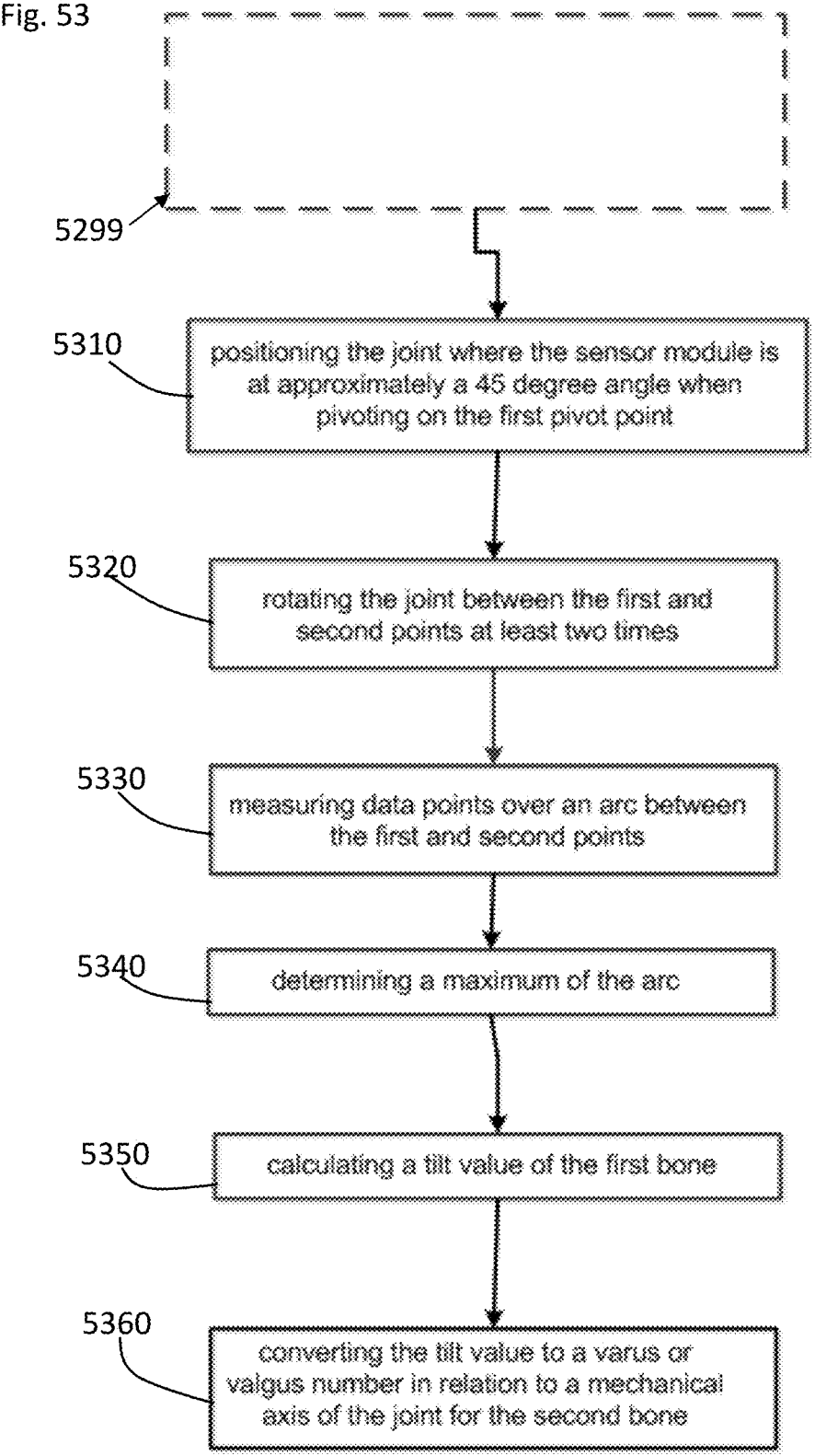
FIG. 53 illustrates another method of measuring joint alignment between first and second bones.

FIG. 52 illustrates at least one embodiment 5299 is directed to methods and devices using kinetic measurements for joint alignment. For example at least one embodiment 5200 is directed to a method of measuring joint alignment between first (e.g., femur) and second bones (e.g., tibia) comprising the steps of: positioning a joint to a target flexion value (e.g. a chosen knee bent) as measured by a sensored module within the joint 5210; rotating the joint 5220 between a first point and a second point where the first and second points are on opposing sides of the joint 5220. For example referring to FIG. 1A the first point can be along path 102A, while the second point is along 101A and the act of rotating is moving along the paths 101A and 102A. For example, as displayed in FIG. 53, 5310 the first point can be about 45 degrees medially along 101A measured with respect to the vertical axis 100A, while the second point can be about 45 degrees laterally along 102A measured with respect to the vertical axis 100A. A first alignment value is saved 5230, where the first alignment value is related to the position of the first bone, for example the first alignment value can be the angular relationship between an axis along the first bone and the tibia crest 345. Then positioning 5240 the joint to a second target flexion value (e.g., moving a leg to extension). When the joint is at the second target flexion value the joint can then be rotated back and forth to obtain the alignment of the second bone. For example one can rotate 5250 the joint about a third point and a fourth point where the third and fourth points are on opposite sides of the joint, for example with the leg in extension the leg can be rotated along the path 101A and 102A with a pivot point at the heel to acquire the second alignment value. The second alignment value is saved 5260 (e.g., computer readable memory), where the second alignment value is related to the position of the second bone, for example the second alignment value can be the angular relationship between an axis along the second bone and the tibia crest 345. The first and second alignment values can be used by a processor to calculate alignment 5270 of the first bone with regards to the mechanical axis and/or calculate the alignment of the second bone (e.g., angle between an axis through the second bone and the mechanical axis) with regards to the mechanical axis. Note that alignment can be with regards to other axes, for example the tibia crest 345 instead of the mechanical axis.

Note that the rotation 5280 between the first and second points or the third and fourth points 5290 can be about a pivot point for example the heel or some other chosen pivot point, where the pivot points for either can be different but relate to the mechanics of the joint. Note that the process of alignment can use a sensor as described above, where the sensor can be zero'd 5295 with respect to a first reference plane and a second reference plane (e.g., horizontal, vertical planes). For example as described above the horizontal plane can be a table top and the vertical plane perpendicular to the table top.

Note that during rotation, measurements 5330 can be taken along the paths (e.g., along 101A and 102A). The amount of measurements depends on the sampling rate and the speed of rotation. The measurements can be used by the processor to calculate 5340 the maximum of the arc of motion, for example the highest point above the table.

In addition to alignment the measurements can be used to calculate a tilt value 5350 that is related to vargus or valgus misalignment. For example the measurements 5360 can determine the angles 193A or 195A, which can be measured with respect to various axis (e.g., mechanical axis, tibia crest).

Note that the sensor can determine flexion position, for example prior to rotation between the third and fourth points the sensor can provide feedback to a user to flex the joint until an axis of the sensor acquires a desired orientation, for example the horizontal plane of the sensor intersecting the table plane by an angle (e.g., 45 degrees).

Figure 54:
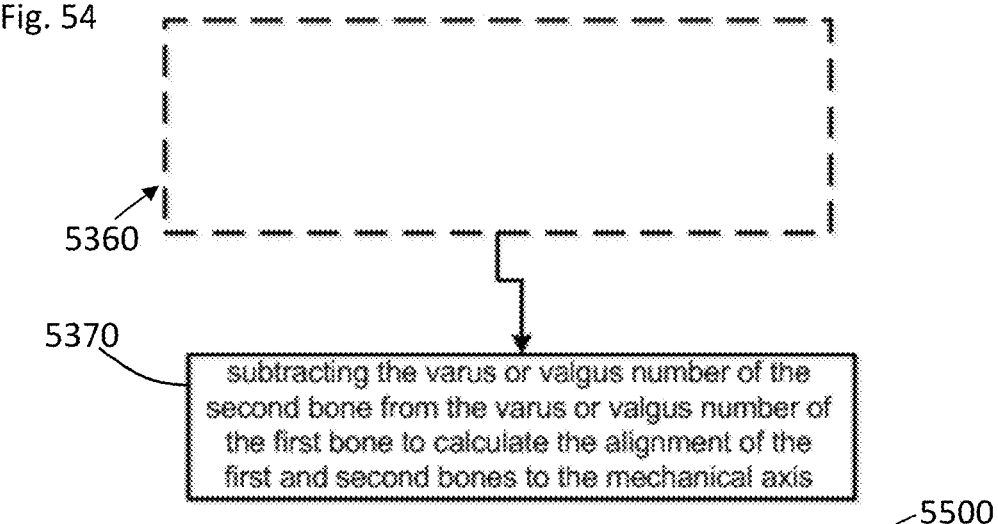
FIG. 54 illustrates another method of measuring joint alignment between first and second bones.

FIG. 54 illustrates steps according to an embodiment where the vargus/valgus angle of the first bone can be compared to the vargus/valgus angle of the second bone to calculate 5370 the alignment of the first and second bones to a reference axis (e.g., mechanical axis, tibia crest).

Figure 55:
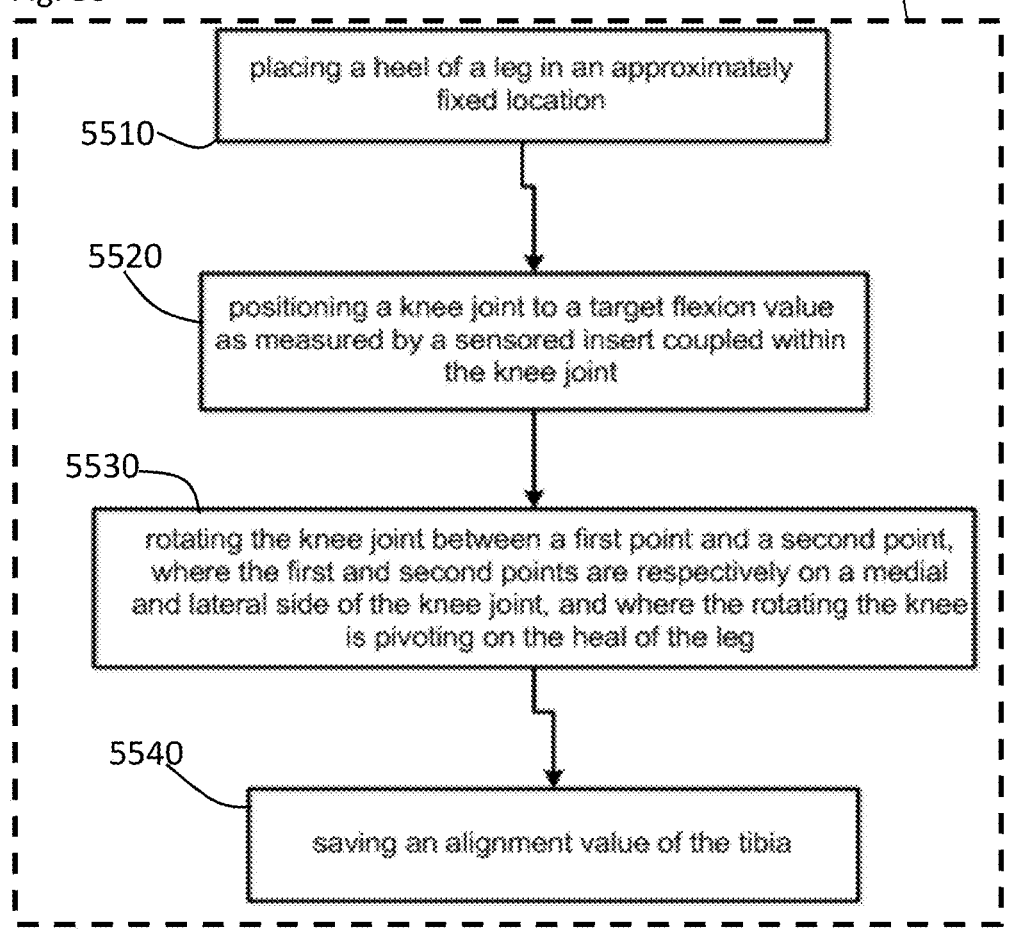
FIG. 55 illustrates a method of measuring alignment of a tibia to a mechanical axis of a leg.
Figure 56:
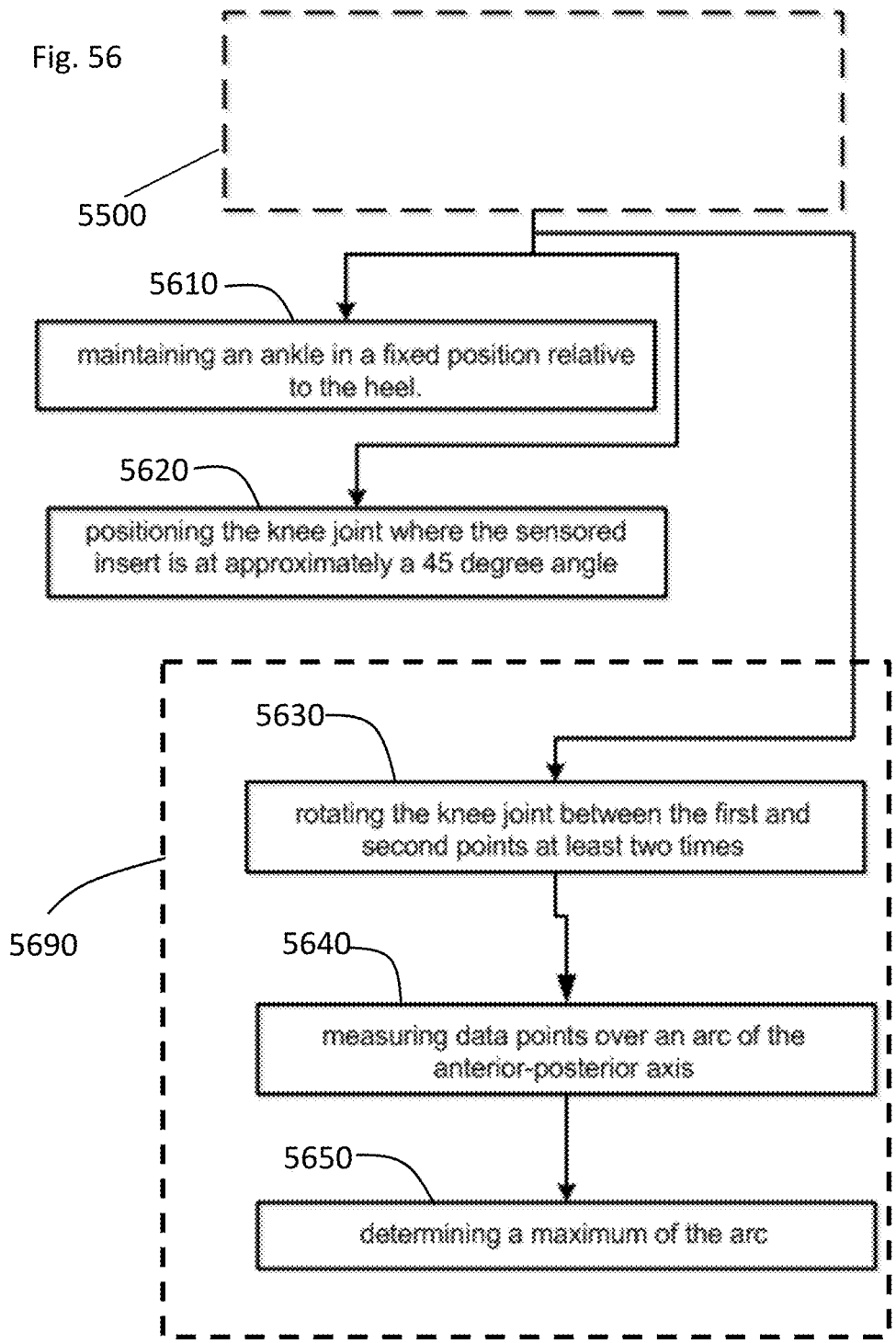
FIG. 56 illustrates another method of measuring alignment of a tibia to a mechanical axis of a leg.

FIG. 55 illustrates a block diagram of at least one embodiment is directed to a method of measuring alignment 5500 of a tibia to a mechanical axis or a tibia crest of a leg which includes the steps of: placing a heel 5510 of a leg in an approximately fixed location; positioning a knee joint 5520 to a target flexion value as measured by a sensored insert coupled within the knee joint; rotating the knee joint 5530 between a first point and a second point (e.g., as described above), where the first and second points are respectively on a medial and lateral side of the knee joint, and where rotating the knee is pivoting on the heal of the leg; and saving an alignment value 5540 of the tibia. Additional embodiments, as illustrated in FIG. 56, can further include a step of maintaining an ankle in a fixed position 5610 relative to the heel. Additional embodiments can further include a step of positioning the knee joint 5620 where the sensored insert (e.g., an insert with sensors) is at approximately a 45 degree angle. Additional embodiments 5690 can further include the steps of rotating the knee joint 5630 between the first and second points at least two times; measuring data points 5640 over an arc of the anterior-posterior axis; and determining a maximum of the arc 5650 (e.g., as discussed above).

Figure 57:
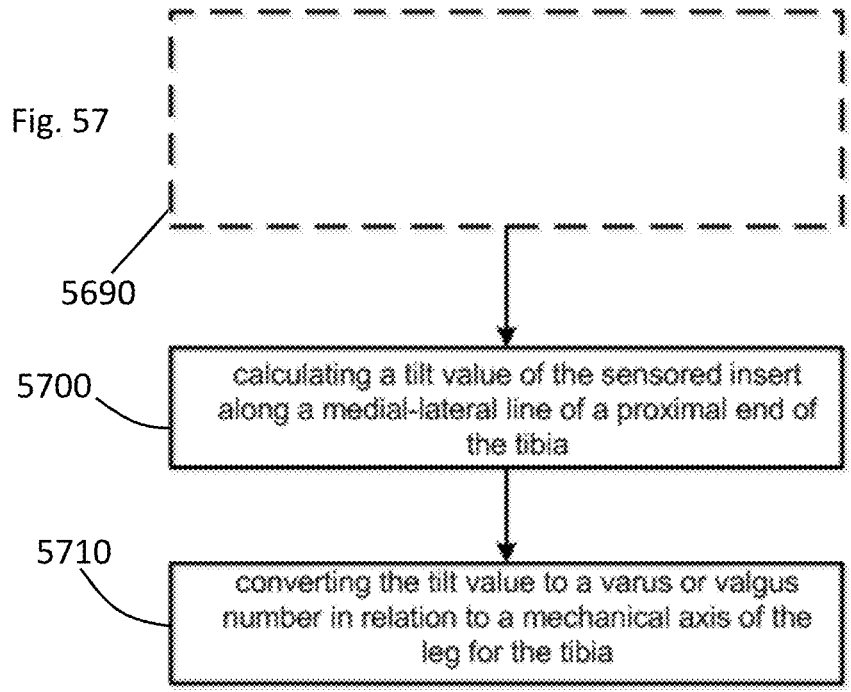
FIG. 57 illustrates another method of measuring alignment of a tibia to a mechanical axis of a leg.

Additional embodiments, for example as illustrated in FIG. 57, can further include the steps of calculating a tilt value 5700 of the sensored insert along a medial-lateral line (e.g., in direction 101 and 102 respectively) of a proximal end of the tibia; converting the tilt value 5710 to a varus or valgus number in relation to a mechanical axis or a tibia crest of the leg for the tibia.

Figure 58:
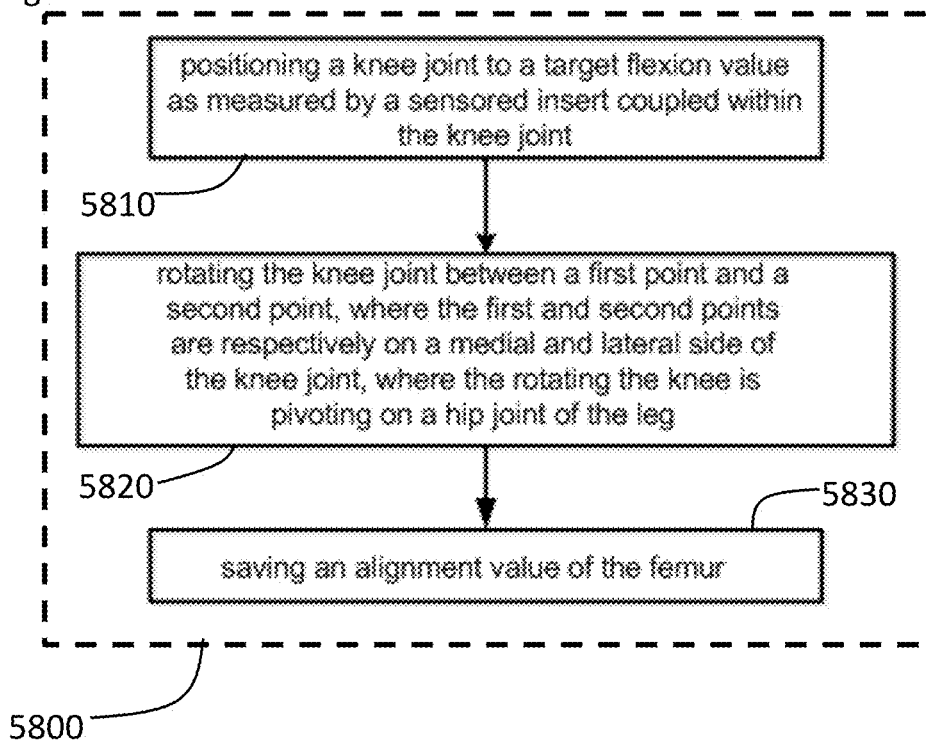
FIG. 58 illustrates method of measuring alignment of a femur.

Additional embodiments 5800, for example as illustrated in FIG. 58, can further measure the alignment of the femur, for example the process can include the steps of positioning a knee joint 5810 to a target flexion value (e.g., so that the leg is bent or in extension) as measured by a sensored insert coupled within the knee joint; rotating the knee joint 5820 between a first point and a second point, where the first and second points are respectively on a medial and lateral side of the knee joint, where rotating the knee is pivoting on a hip joint of the leg; and saving an alignment value 5830 of the femur.

Figure 59:
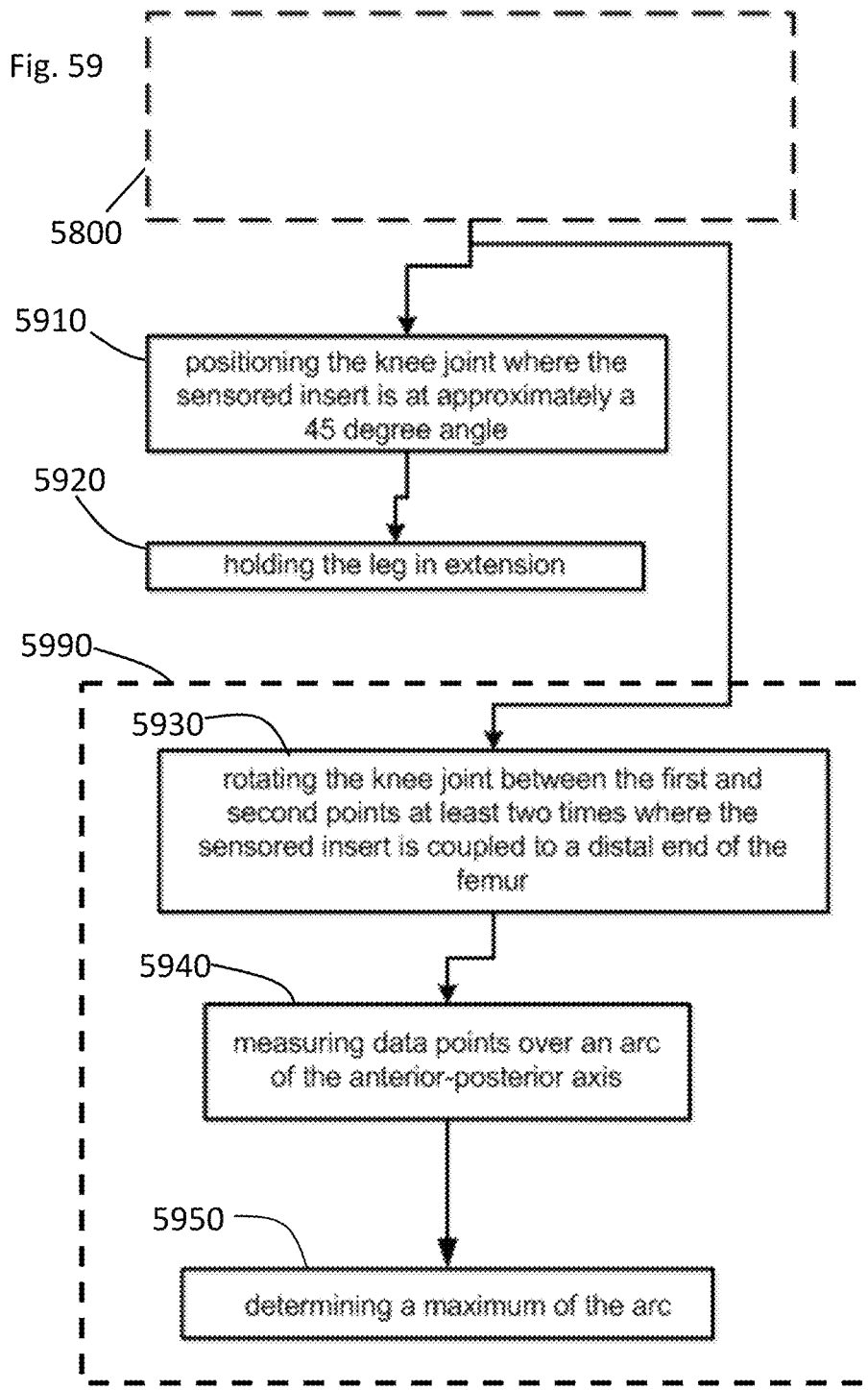
FIG. 59 illustrates another method of measuring alignment of a femur.

Note that additional embodiments, for example as illustrated in FIG. 59, can include positioning the knee joint 5910 to various orientations for example where the sensored insert (e.g., coupled to the knee) is at approximately a 45 degree angle or positioning the leg 5920 in extension.

Figure 60:
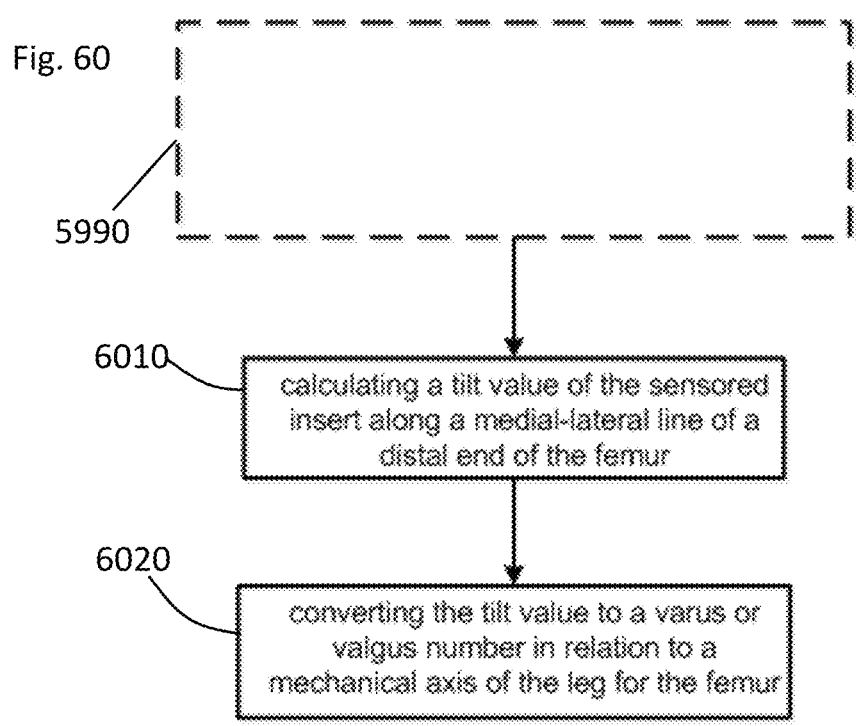
FIG. 60 illustrates another method of measuring alignment of a femur.

Additional embodiments 5990, for example as illustrated in FIG. 59, for femur alignment can include the steps of: rotating the knee joint 5930 between the first and second points at least two times where the sensored insert is coupled to a distal end of the femur; measuring data points 5940 over an arc of the anterior-posterior axis; and determining 5950 a maximum of the arc. Additional embodiments, for example as illustrated in FIG. 60, for femur alignment can include the steps of: calculating a tilt value 6010 of the sensored insert along a medial-lateral line of a distal end of the femur; and converting the tilt value 6020 to a varus or valgus number in relation to a mechanical axis of the leg for the femur.

At least one embodiment is directed to methods and devices for displaying information to a user to provide information. The information can have multiple uses, for example provide feedback for alignment and/or surgery.

For example at least one embodiment is directed to a graphical user interface (e.g., 100) on an electronic display (e.g., 105, smart phone screen, electronic screen, tablet screen, touch screen, projected display, heads-up display), a memory (e.g., RAM, hard drive, USB removable memory), and one or more processors (e.g., single processor, RISC, multiply linked processors such as dual processors) to execute one or more programs (e.g., the software system controlling the feedback display) stored in the memory, the graphical user interface comprising: a portion of an orthopedic system (e.g., leg, knee joint, hip joint, elbow joint) displayed on the electronic display; a parameter (e.g., CP rotation, A-P slope, flexion angle, tibial rotation, tibia angle, medial load on a sensor, lateral load on a sensor, sensor rotation angle, load locations) of the orthopedic system displayed on the electronic display; a portion of an orthopedic insert displayed on the electronic display; and a parameter of the orthopedic insert displayed on the electronic display, where in response to detecting movement of the orthopedic system the displayed portion of the orthopedic system (e.g., 162) is moved, a change of the parameter of the orthopedic system is displayed, and a change in parameter of the orthopedic insert is displayed.

In at least one embodiment the parameter of the orthopedic insert is a medial contact location displayed as a symbol or area of contact (e.g., 158A and 158B) on the displayed portion of the orthopedic insert (e.g., 157). In at least one embodiment the parameter of the orthopedic insert is a lateral contact location displayed as a symbol or area of contact on the displayed portion of the orthopedic insert. In at least one embodiment the parameter of the orthopedic insert is a medial contact load displayed as a range on a display (e.g., BB.BB and AA.AA, in FIG. 24). In at least one embodiment the parameter of the orthopedic insert is a lateral contact load displayed as a range (e.g., BB.BB and AA.AA, in FIG. 24) on a display.

At least one embodiment further includes the steps of displaying a dial (e.g., 2900, 3000) that moves in response to movement of the orthopedic system. The embodiment can change the color (e.g., from white to blue, yellow to white) of the displayed parameter of the orthopedic system when the value of the parameter of the orthopedic system is within a predetermined range (e.g., +/−1 to 3 degrees of an angular target, +/−1 to 5 mm of a translational location) of a target value of the parameter of the orthopedic system. At least one embodiment further includes the steps of changing the color of the displayed parameter of the orthopedic insert when the value of the parameter of the orthopedic insert is within a predetermined range of a target value of the parameter of the orthopedic insert. Additionally embodiment can change the border (e.g., 3290) around a value when that value has been fixed.

At least one embodiment can combine the GUI system with the measurement system. For example at least one embodiment can be directed to a method of providing feedback of an orthopedic alignment system coupled to display comprising: displaying a portion of an orthopedic system on a display; displaying a parameter of the orthopedic system in the display; displaying a portion of an orthopedic insert (e.g., a tibia insert) in the display (e.g., 157); displaying a parameter of the orthopedic insert in the display (e.g., 154D); detecting movement of the orthopedic system (e.g., using accelerometers, magnetometers, GPS, acoustics, mechanical measurements), and moving the displayed portion of the orthopedic system in response to the movement of the orthopedic system; detecting a change of the parameter of the orthopedic insert during movement of the orthopedic system; detecting a change of the parameter of the orthopedic system during movement of the orthopedic system; displaying the change in parameter of the orthopedic insert in the display; and displaying the change in parameter of the orthopedic system in the display.

At least one embodiment is directed to measurement of the anterior-posterior slope/tilt. The measurement can be used, for example to obtain the A-P slope of a bone cut or of a prosthetic component (e.g., tibial insert) inserted into an orthopedic system. The A-P slope can provide user (e.g., a surgeon) information to determine the prosthetic component has been placed correctly. For example if, during a knee surgery, all the ligaments are in place the bone cut would not have any slope. If the PCL were removed, for example, a supporting post is on the insert and has been found to require an A-P tilt to allow movement in flexion, thus identifying the A-P tilt or angle can be important for more accurate fitting of the prosthetic component.

Figure 61:
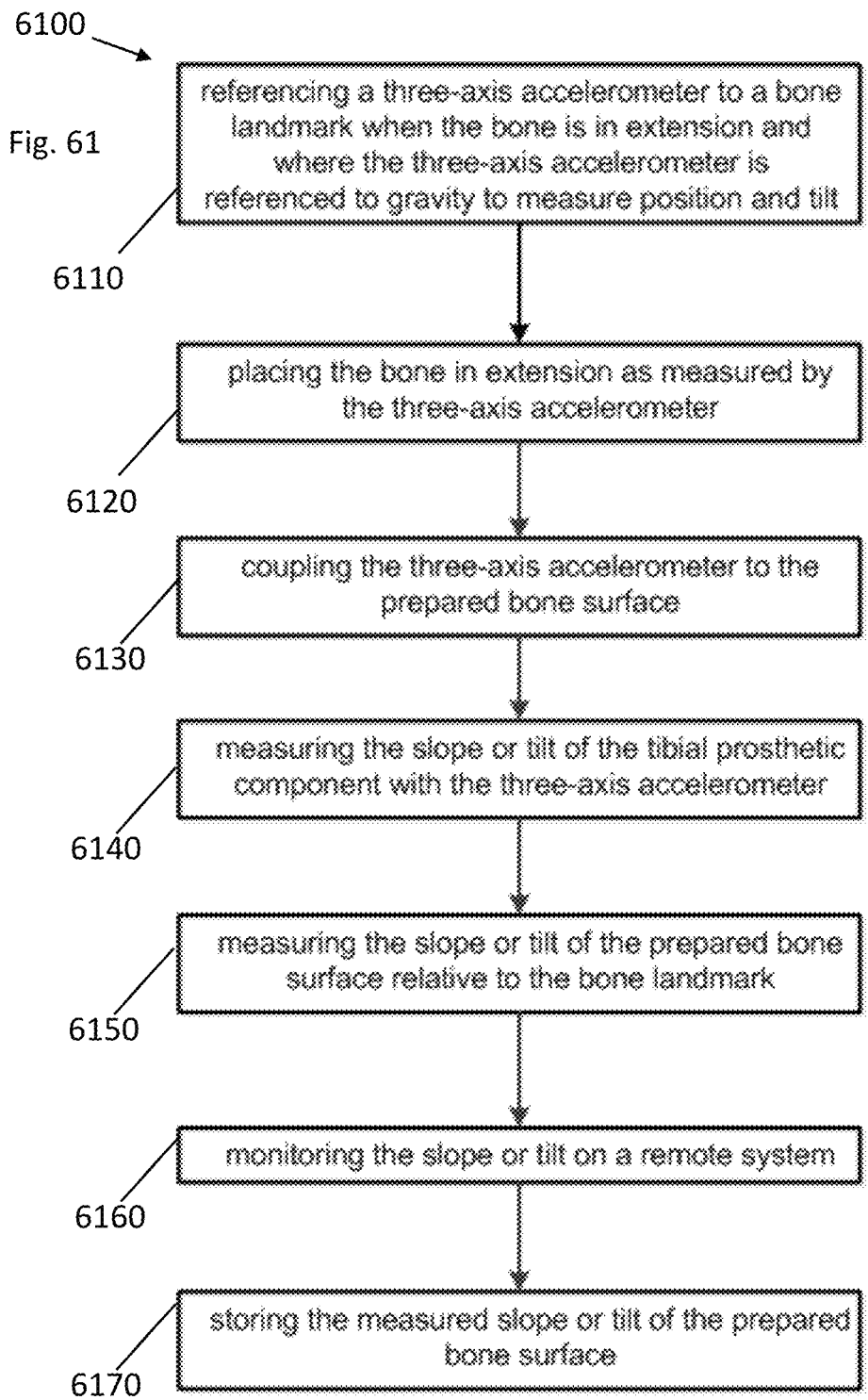
FIG. 61 illustrates a method of measuring slope or tilt of a prepared bone surface of a bone.

Thus, for example one embodiment, as illustrated in FIG. 61, can be directed to a method 6100 of measuring slope or tilt of a prepared bone surface of a bone comprising the steps of: referencing a three-axis accelerometer 6110 to a bone landmark (e.g., tibia crest) when the bone is in extension and where the three-axis accelerometer is referenced to gravity to measure position and tilt; placing the bone in extension 6120 as measured by the three-axis accelerometer; coupling the three-axis accelerometer 6130 to the prepared bone surface; and measuring the slope or tilt of the tibial prosthetic component with the three-axis accelerometer. Note that the accelerometer can be calibrated with respect to a horizontal and vertical reference. The horizontal reference can be a table top, while the vertical reference can be perpendicular to the table top. A detailed discussion of accelerometers is not included since it is well known by one of ordinary skill in the arts; however U.S. patent application Ser. No. 13/673,921, "Motion and Orientation Sensing Module or Device for Positioning of Implants", contains discussion of sensors, bit and memory discussions, and accelerometers, and the Applications content is incorporated by reference in its entirety.

Note that measuring the slope or tilt 6140 of the tibial prosthetic component includes the steps of: measuring the slope or tilt 6150 of the prepared bone surface relative to a bone landmark (e.g., tibia crest, mechanical axis); monitoring the slope or tilt 6160 on a remote system; and storing 6170 (e.g., in computer readable memory) the measured slope or tilt of the prepared bone surface.

Figure 62:
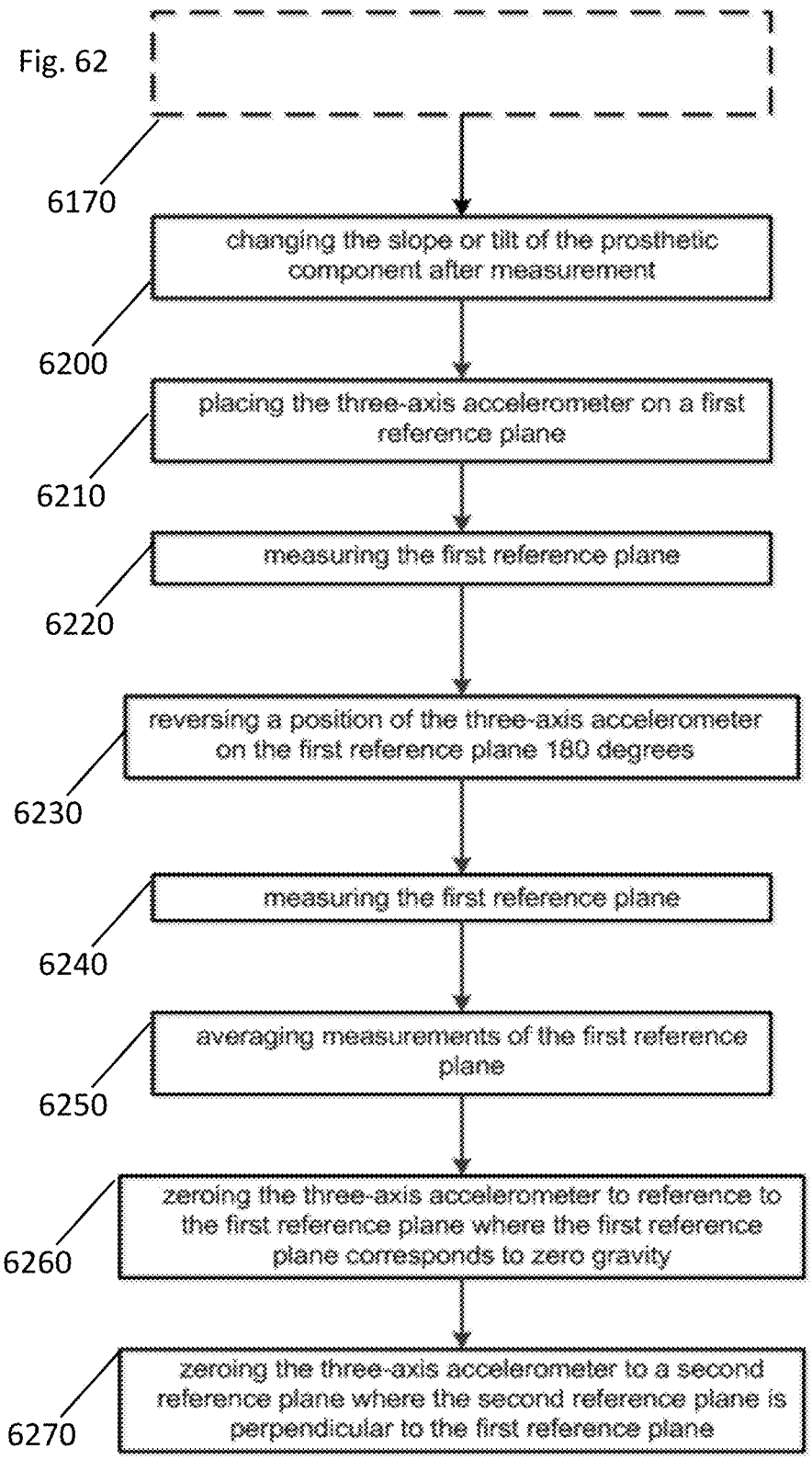
FIG. 62 illustrates another method of measuring slope or tilt of a prepared bone surface of a bone.

Additional embodiments, as illustrated in FIG. 62, can further include the step of changing the slope or tilt 6200 of the prosthetic component after measurement. Additional embodiments can further include the step of placing 6210 the three-axis accelerometer (e.g., where the accelerometer is in a sensor) on a first reference plane (e.g., a horizontal plane such as a table top); and measuring 6220 the first reference plane (e.g., recording a first set of data measured by the accelerometer); reversing a position 6230 of the three-axis accelerometer on the first reference plane 180 degrees; measuring 6240 the first reference plane (e.g., recording a second set of data measured by the accelerometer); averaging measurements 6250 of the first reference plane (e.g., averaging the values of the first data set and second data set); and zeroing 6260 the three-axis accelerometer to reference to the first reference plane where the first reference plane corresponds to zero acceleration (e.g., gravity). For example the first and second data sets can include x, y, z values, and the averaging step can include averaging all of the x, y, and z values of both data sets. Then to zero the processor can obtain offset x, y, and z values to apply to any measurement so that when a sensor (e.g., with the accelerometer included) lies on the first reference plane, the x, y, and z values read about zero.

As discussed above additional embodiments can include the step of zeroing 6270 the three-axis accelerometer to a second reference plane (e.g. a plane perpendicular of the first plane).

Figure 63:
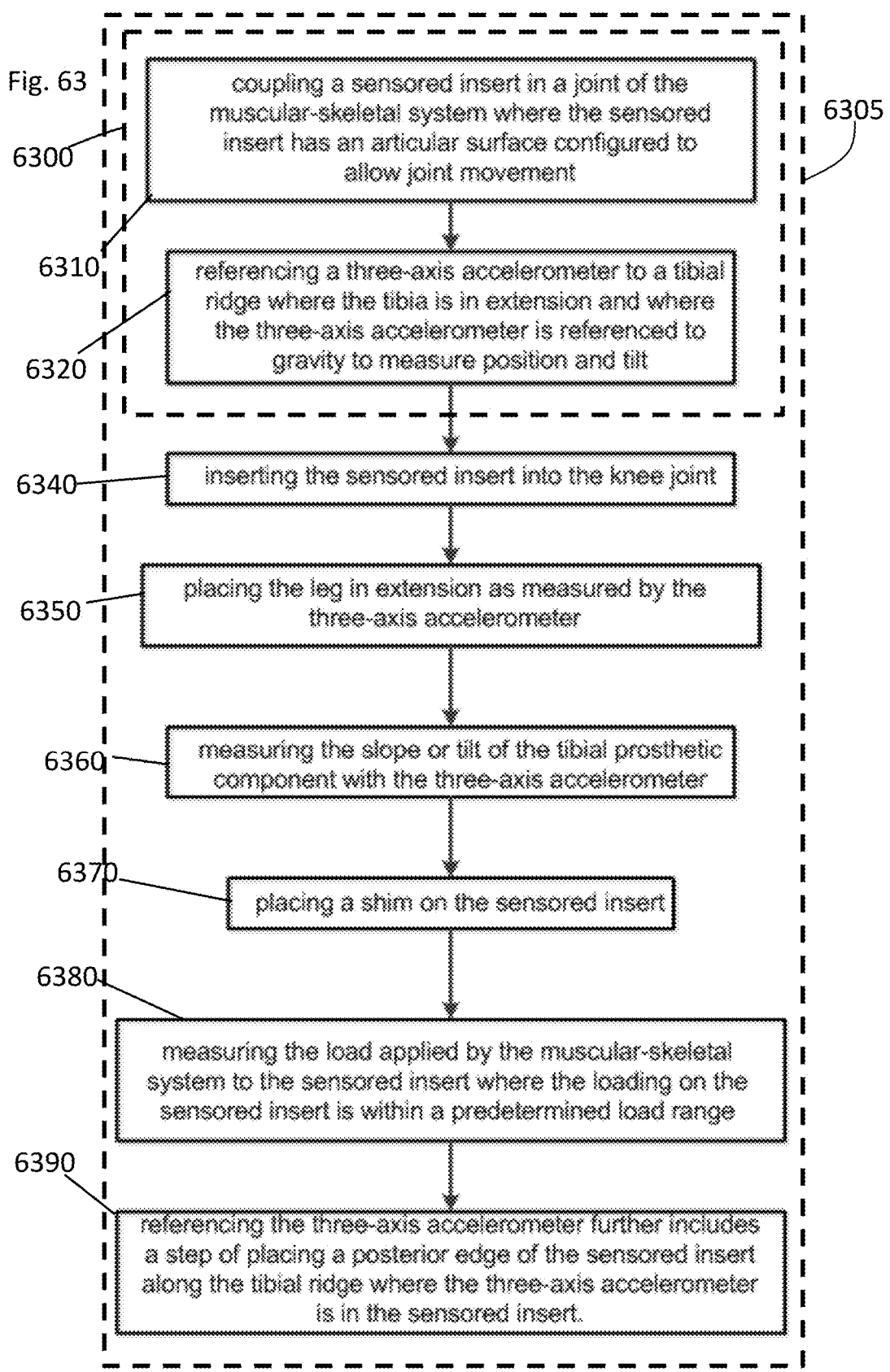
FIG. 63 illustrates a method of measuring slope or tilt of a tibial prosthetic component coupled to a tibia.

Additional embodiments 6300, as illustrated in FIG. 63, include the steps of coupling 6310 a sensored insert in a joint of the muscular-skeletal system where the sensored insert has an articular surface configured to allow joint movement; and referencing 6320 a three-axis accelerometer to a tibial ridge (e.g., or tibia crest) where the tibia is in extension and where the three-axis accelerometer is used to measure position and tilt.

Additional embodiments 6305 include the steps of inserting 6340 the sensored insert into the knee joint; placing the leg 6350 in extension as measured by the three-axis accelerometer; and measuring the slope or tilt 6360 of the tibial prosthetic component with the three-axis accelerometer.

Additional embodiments include the steps of placing a shim 6370 on the sensored insert; and measuring the load applied 6380 by the muscular-skeletal system to the sensored insert where the loading on the sensored insert is within a predetermined load range.

Additional embodiments include the steps of referencing the three-axis accelerometer 6390 further includes a step of placing a posterior edge of the sensored insert along the tibial ridge where the three-axis accelerometer is in the sensored insert.

Figure 64:
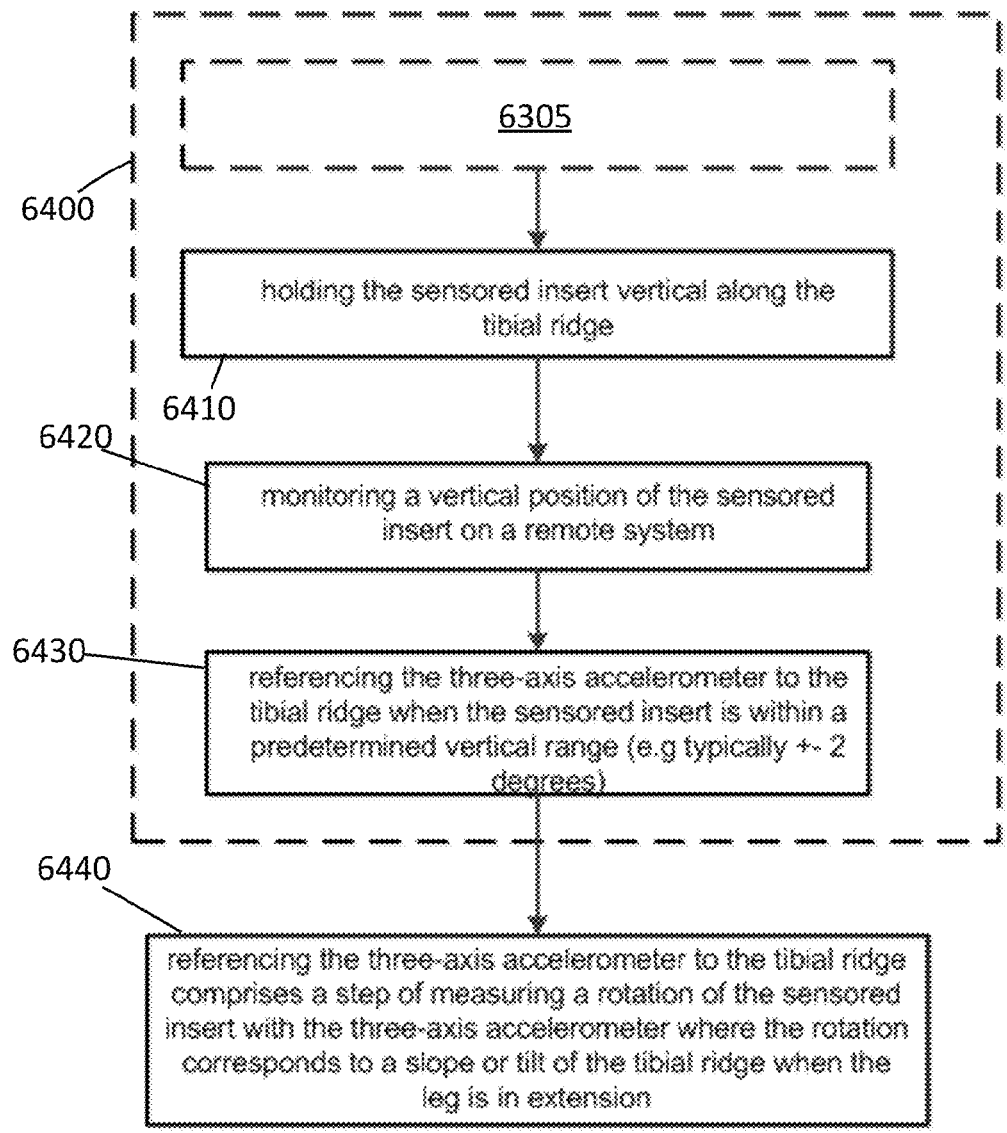
FIG. 64 illustrates another method of measuring slope or tilt of a tibial prosthetic component coupled to a tibia.

Additional embodiments 6400, illustrating FIG. 64, include the steps of holding 6410 the sensored insert vertical along the tibial ridge; monitoring 6420 a vertical position of the sensored insert on a remote system; referencing the three-axis accelerometer 6430 to the tibial ridge when the sensored insert is within a predetermined vertical range (e.g., typically +−2 degrees).

Additional embodiments include the steps of referencing the three-axis accelerometer 6440 to the tibial ridge comprises a step of measuring a rotation of the sensored insert with the three-axis accelerometer where the rotation corresponds to a slope or tilt of the tibial ridge when the leg is in extension.

Figure 65:
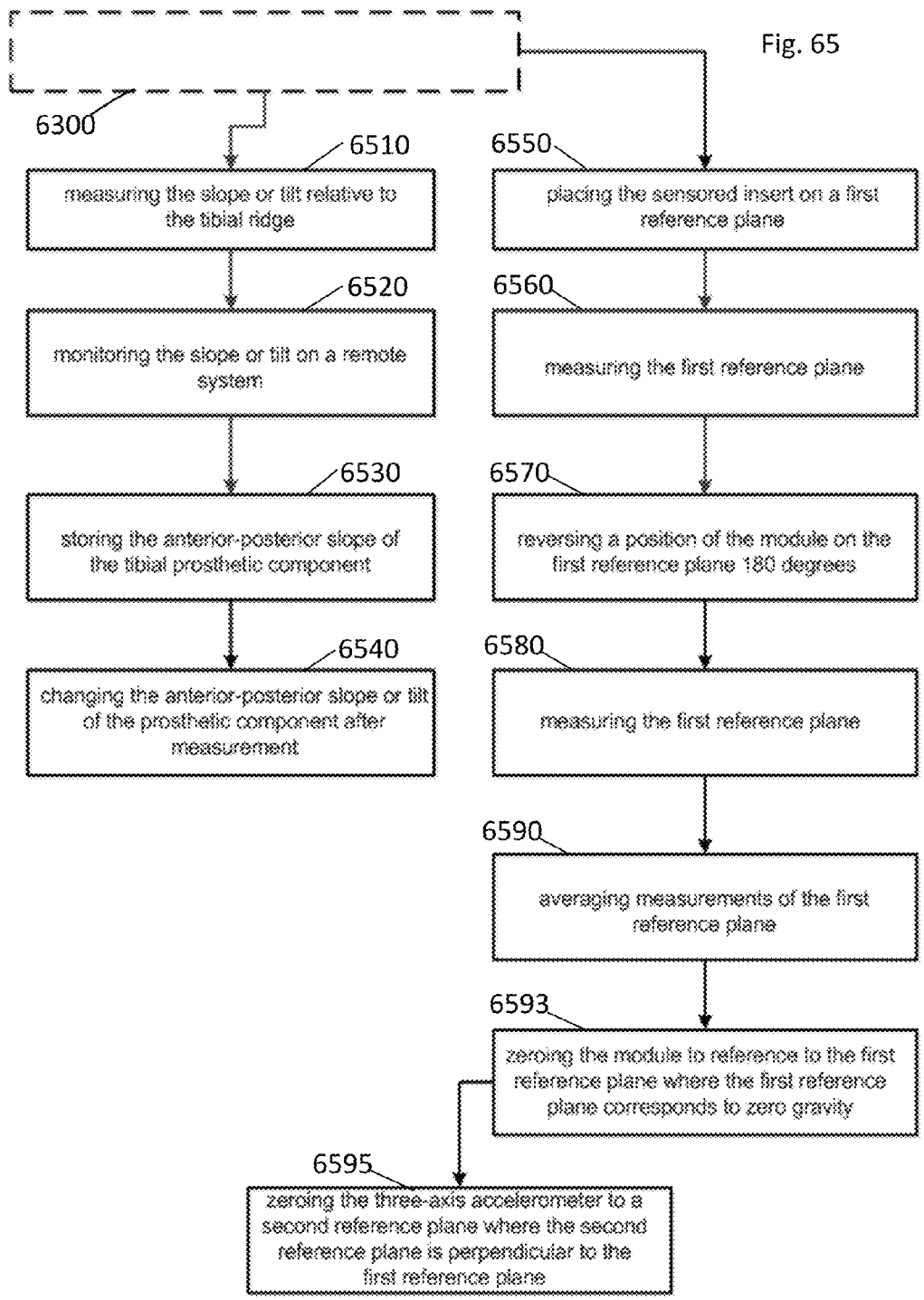
FIG. 65 illustrates another method of measuring slope or tilt of a tibial prosthetic component coupled to a tibia.

Additional embodiments, illustrated in FIG. 65, include the steps of measuring the slope or tilt of the tibial prosthetic component includes the steps of: measuring the slope or tilt 6510 relative to the tibial ridge; monitoring the slope or tilt 6520 on a remote system; and storing the anterior-posterior slope 6530 of the tibial prosthetic component.

Additional embodiments include the step of changing the anterior-posterior (A-P) slope or tilt 6540 of the prosthetic component after measurement.

Additional embodiments include the steps of placing the sensored insert 6550 on a first reference plane; and measuring 6560 the first reference plane; reversing 6570 a position of the module on the first reference plane 180 degrees; measuring 6580 the first reference plane; averaging 6590 measurements of the first reference plane; and zeroing 6593 the module to reference to the first reference plane where the first reference plane corresponds to zero gravity.

Additional embodiments include the step of zeroing 6595 the three-axis accelerometer to a second reference plane where the second reference plane is perpendicular to the first reference plane.

Figure 66:
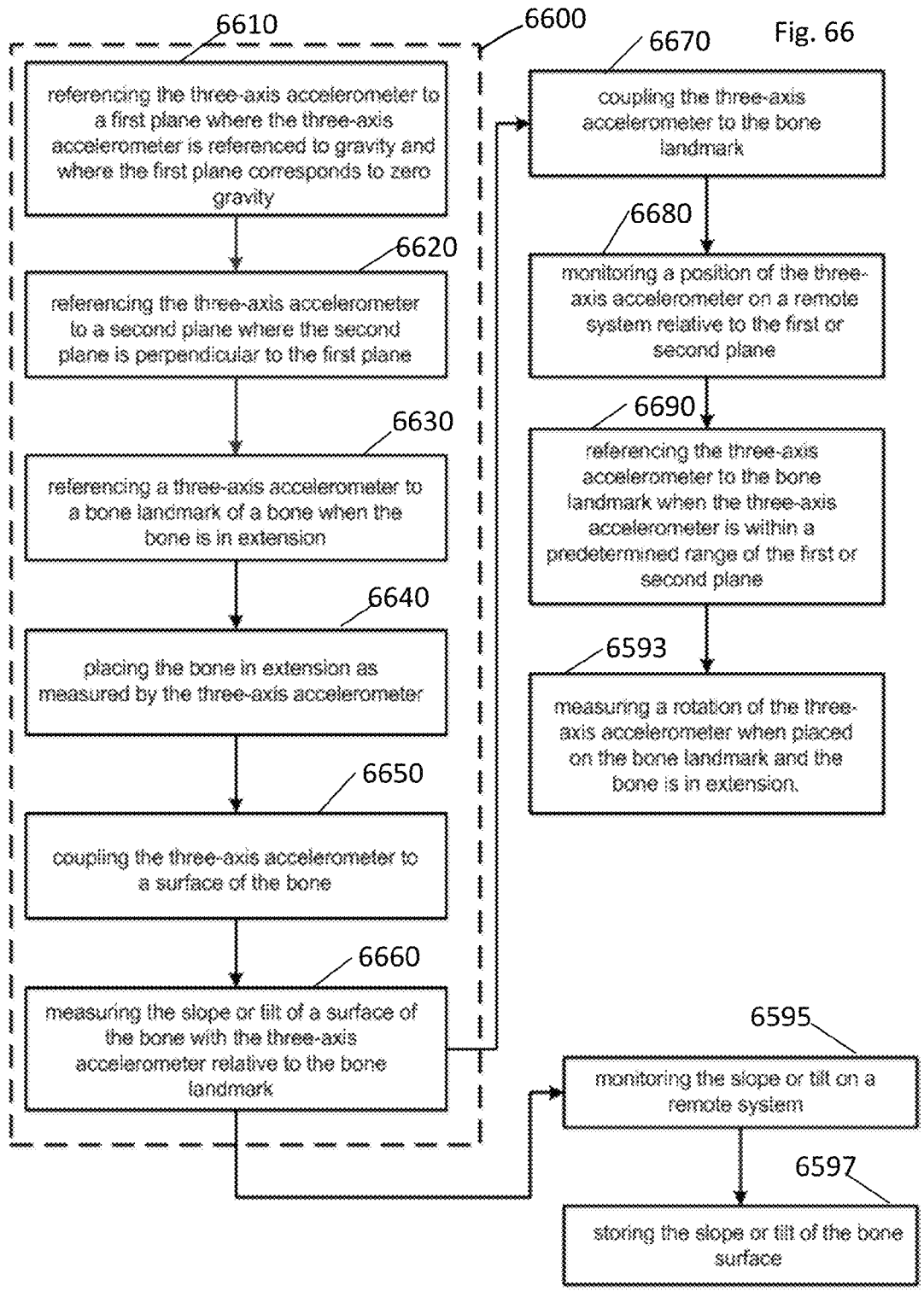
FIG. 66 illustrates a method of referencing a three-axis accelerometer to measure location, tilt, and rotation of the muscular-skeletal system.

At least one embodiment, as illustrated in FIG. 66, is directed to a method 6600 of referencing a three-axis accelerometer to measure location, tilt, and rotation of the muscular-skeletal system comprising the steps of: referencing the three-axis accelerometer 6610 to a first plane where the three-axis accelerometer is referenced to gravity and where the first plane corresponds to zero gravity; referencing the three-axis accelerometer 6620 to a second plane where the second plane is perpendicular to the first plane; referencing a three-axis accelerometer 6630 to a bone landmark of a bone when the bone is in extension; placing the bone in extension 6640 as measured by the three-axis accelerometer; coupling 6650 the three-axis accelerometer to a surface of the bone; and measuring the slope or tilt 6660 of a surface of the bone with the three-axis accelerometer relative to the bone landmark.

Additional embodiments include the steps of coupling 6670 the three-axis accelerometer to the bone landmark; monitoring 6680 a position of the three-axis accelerometer on a remote system relative to the first or second plane; and referencing 6690 the three-axis accelerometer to the bone landmark when the three-axis accelerometer is within a predetermined range of the first or second plane.

Additional embodiments include the step of measuring 6593 a rotation of the three-axis accelerometer when placed on the bone landmark and the bone is in extension. In at least one embodiment the step of measuring the slope or tilt of the bone surface can include the steps of: monitoring 6595 the slope or tilt on a remote system; and storing 6597 the slope or tilt of the bone surface.

Figure 67:
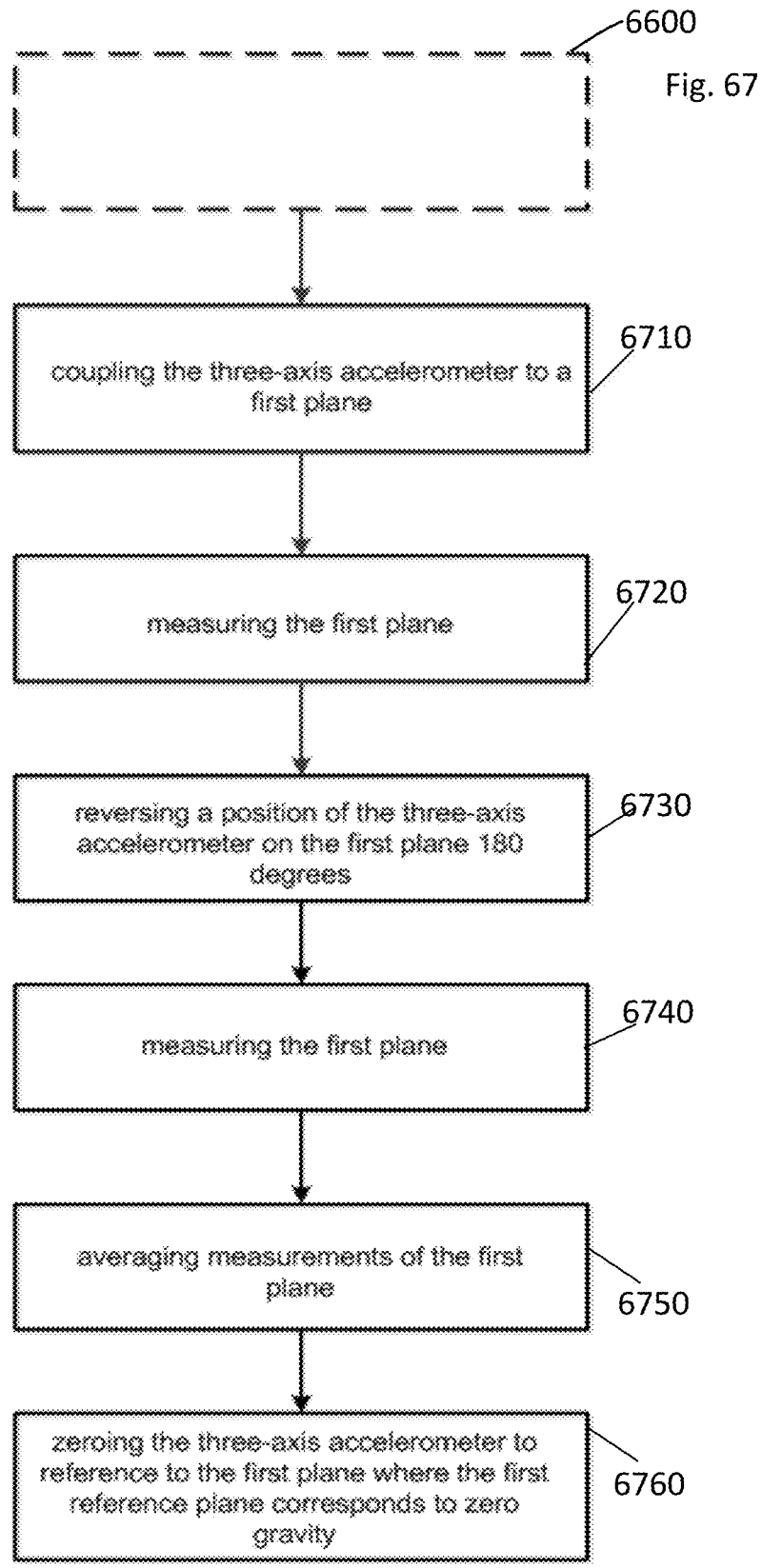
FIG. 67 illustrates another method of referencing a three-axis accelerometer to measure location, tilt, and rotation of the muscular-skeletal system.

Additional embodiments, illustrated in FIG. 67, include the steps of coupling 6710 the three-axis accelerometer to a first plane; measuring 6720 the first plane; reversing a position 6730 of the three-axis accelerometer on the first plane 180 degrees; measuring 6740 the first plane; averaging 6750 measurements of the first plane; and zeroing 6760 the three-axis accelerometer to reference to the first plane where the first reference plane corresponds to zero acceleration (e.g. gravity).

Figure 81:
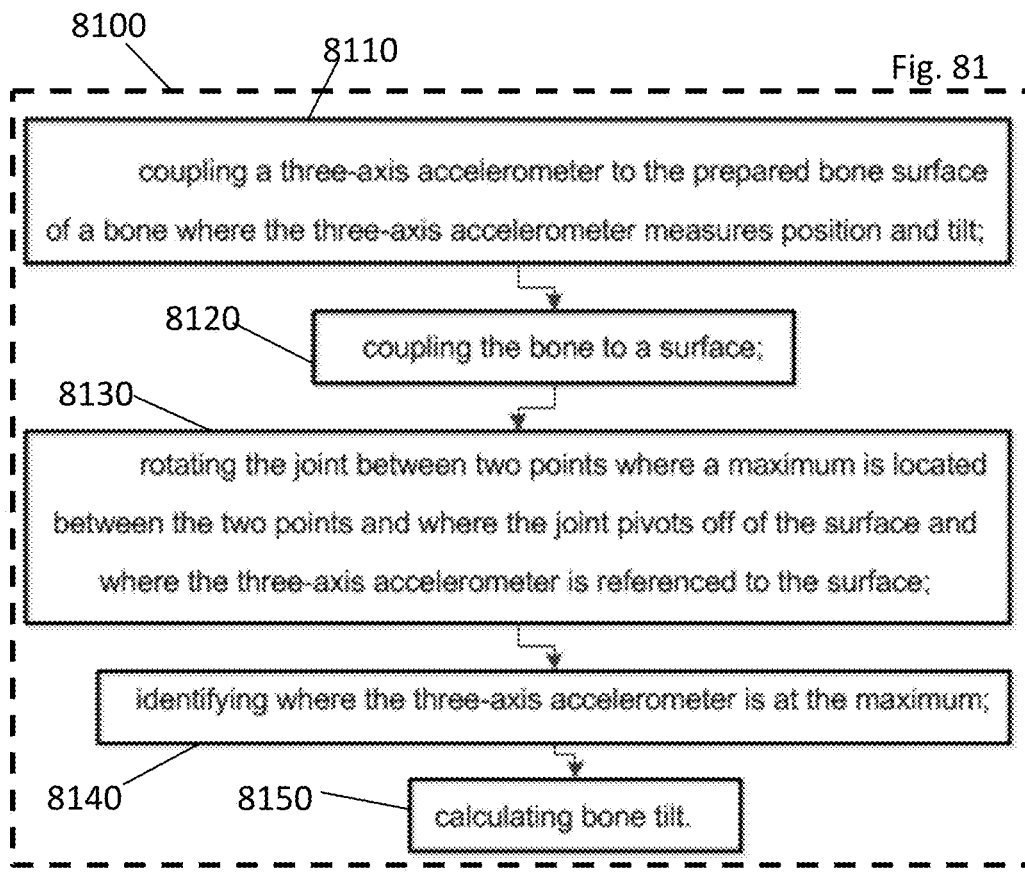
FIG. 81 illustrates method of measuring tilt of a prepared bone surface of a muscular-skeletal joint.

At least one further embodiment is directed to the determination of the medial-lateral tilt of a bone coupled to a joint. A method of measuring tilt 8100, as illustrated in FIG. 81, of a prepared bone surface of a muscular-skeletal joint comprising the steps of: coupling 8110 a three-axis accelerometer to the prepared bone surface of a bone where the three-axis accelerometer measures position and tilt; coupling 8120 the bone to a surface; rotating 8130 the joint between two points where a maximum is located between the two points and where the joint pivots off of the surface and where the three-axis accelerometer is referenced to the surface; identifying 8140 where the three-axis accelerometer is at the maximum; and calculating 8150 bone tilt.

Figure 82:
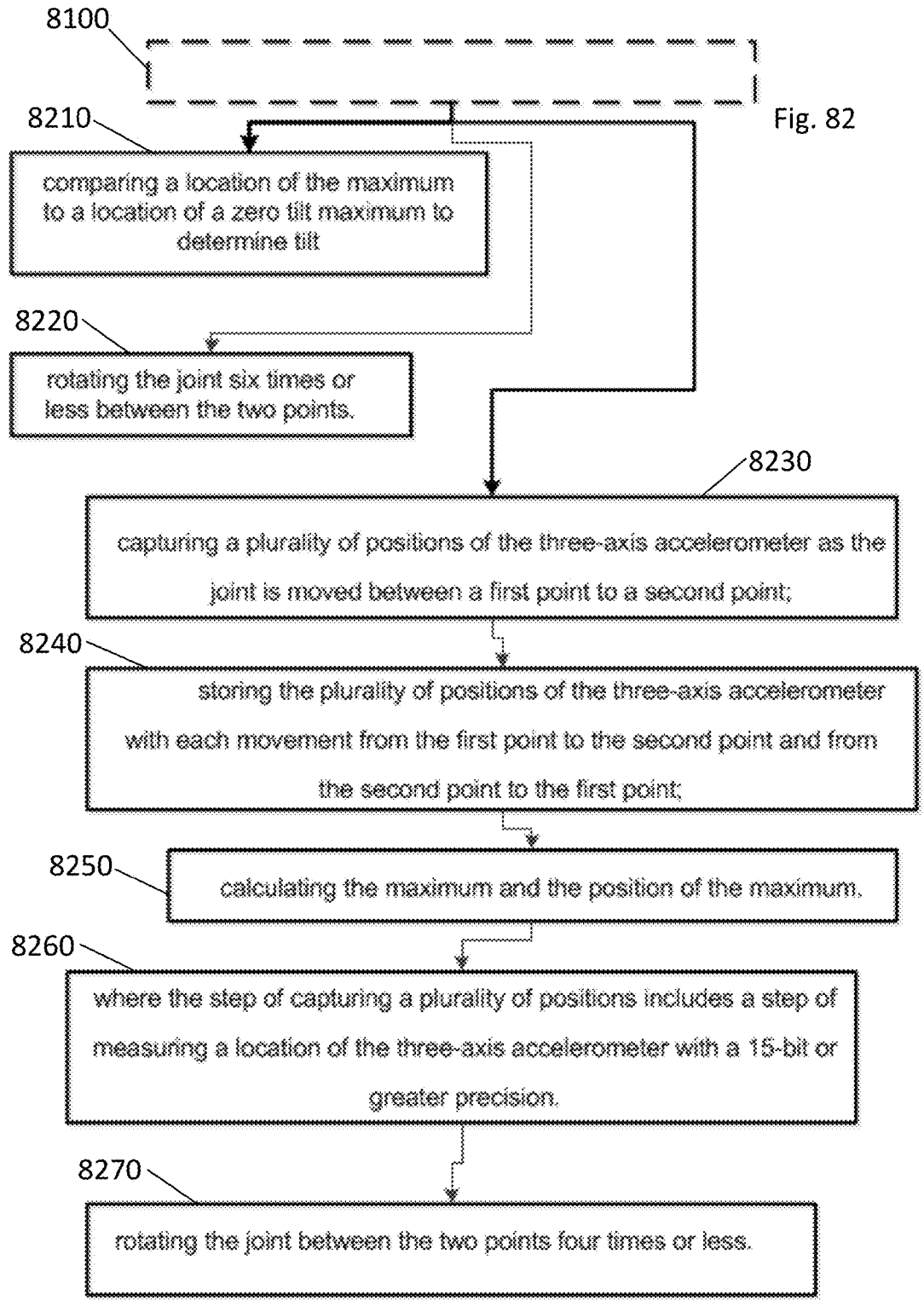
FIG. 82 illustrates another method of measuring tilt of a prepared bone surface of a muscular-skeletal joint.

Additional embodiments, as illustrated in FIG. 82, include the step of comparing 8210 a location of the maximum to a location of a zero tilt maximum to determine tilt.

Additional embodiments include the step of rotating 8220 the joint six times or less between the two points. Note that there is no limit to the number of times rotating the joint can occur.

Additional embodiments include the steps of: capturing 8230 a plurality of positions of the three-axis accelerometer as the joint is moved between a first point to a second point; storing 8240 the plurality of positions of the three-axis accelerometer with each movement from the first point to the second point and from the second point to the first point; and calculating 8250 the maximum and the position of the maximum.

Additional embodiments include the steps of capturing a plurality of positions includes a step of measuring 8260 a location of the three-axis accelerometer with a 15-bit or greater precision.

Additional embodiments include the steps of rotating 8270 the joint between the two points four times or less.

Figure 83:
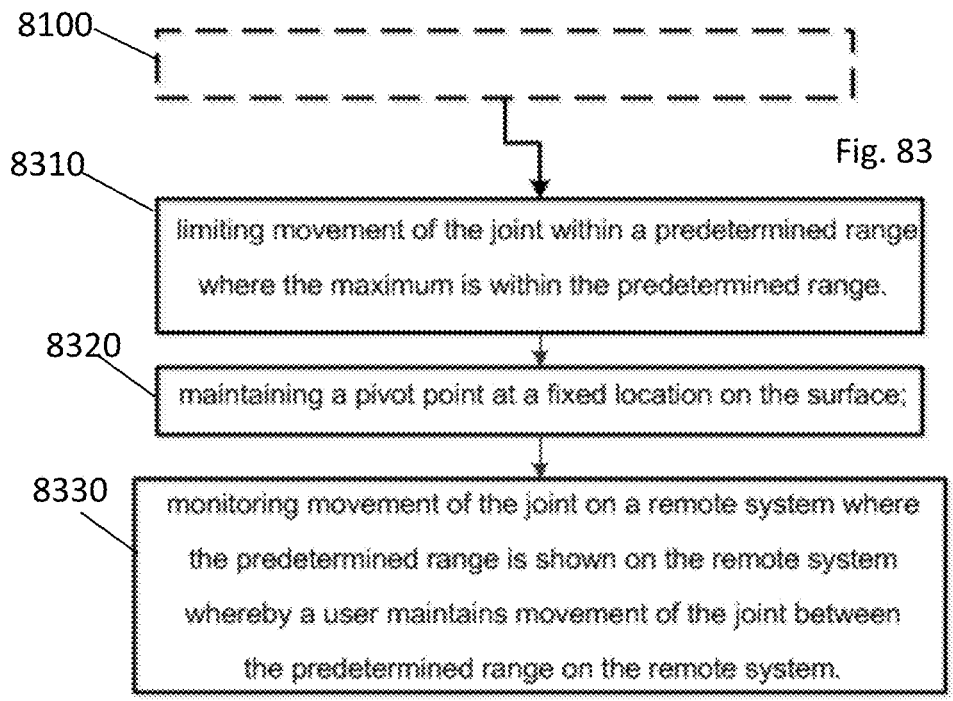
FIG. 83 illustrates another method of measuring tilt of a prepared bone surface of a muscular-skeletal joint.

Additional embodiments, as illustrated in FIG. 83, include the step of limiting movement 8310 of the joint within a predetermined range where the maximum is within the predetermined range. For example if one moves a knee about a pivot point from a medial to a lateral side along the path the knee is at the zenith location, which in this non-limiting example would be the maximum.

Additional embodiments include the steps of: maintaining 8320 a pivot point at a fixed location on the surface; and monitoring 8330 movement of the joint on a remote system where the predetermined range is shown on the remote system whereby a user maintains movement of the joint between the predetermined range on the remote system.

Figure 84:
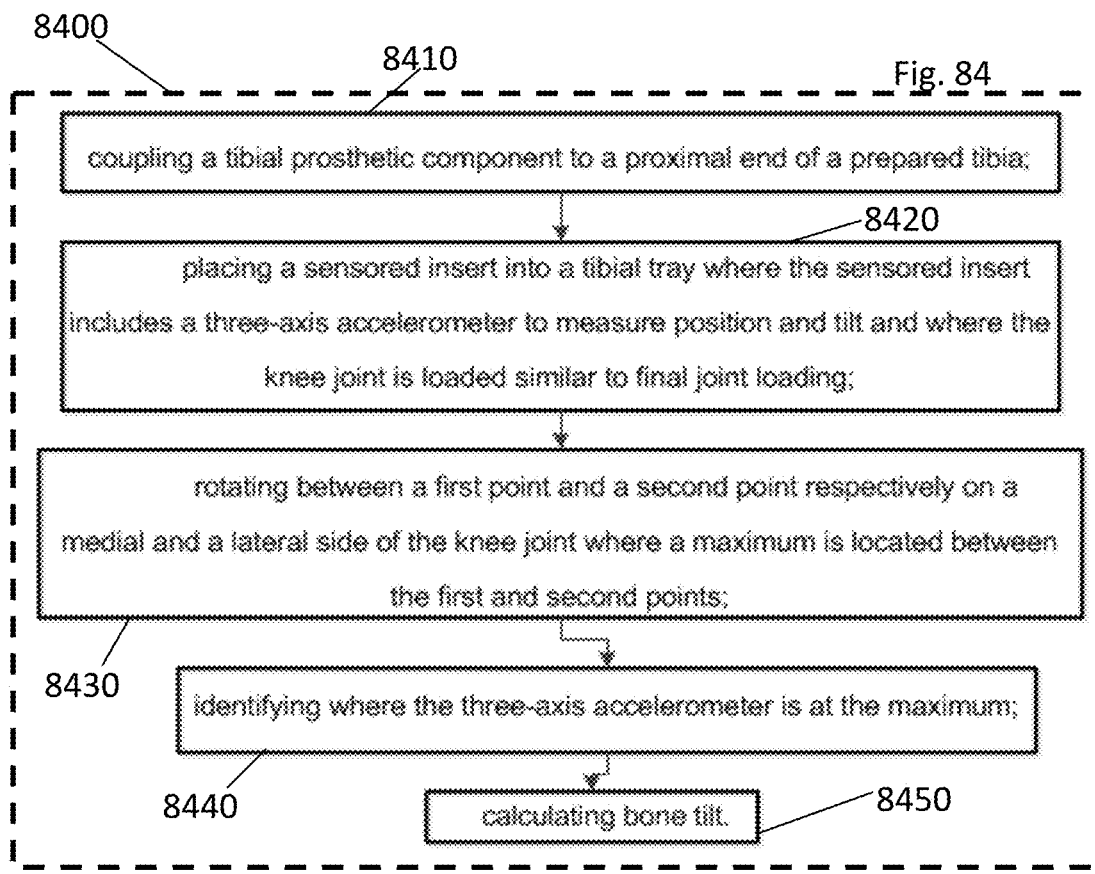
FIG. 84 illustrates a method of measuring medial-lateral tilt of a prepared bone surface of a knee joint.

At least one embodiment 8400, as illustrated in FIG. 84, is directed to a method of measuring medial-lateral tilt of a prepared bone surface of a knee joint comprising the steps of: coupling 8410 a tibial prosthetic component to a proximal end of a prepared tibia; placing 8420 a sensored insert into a tibial tray where the sensored insert includes a three-axis accelerometer to measure position and tilt and where the knee joint is loaded similar to final joint loading; rotating 8430 between a first point and a second point respectively on a medial and a lateral side of the knee joint where a maximum is located between the first and second points; identifying 8440 where the three-axis accelerometer is at the maximum; and calculating 8450 bone tilt. Additional embodiments, as illustrated in FIG. 85, include the steps of: referencing 8510 the three-axis accelerometer to a surface; maintaining 8520 a heel of a leg on the surface; and pivoting 8530 the knee joint off of the heel of the leg. Additional embodiments include the step of: comparing 8540 a location of the maximum to a location of a zero tilt maximum to determine tilt. Additional embodiments include the steps of: rotating 8550 the joint six times or less between the first point and the second point.

Figure 87:
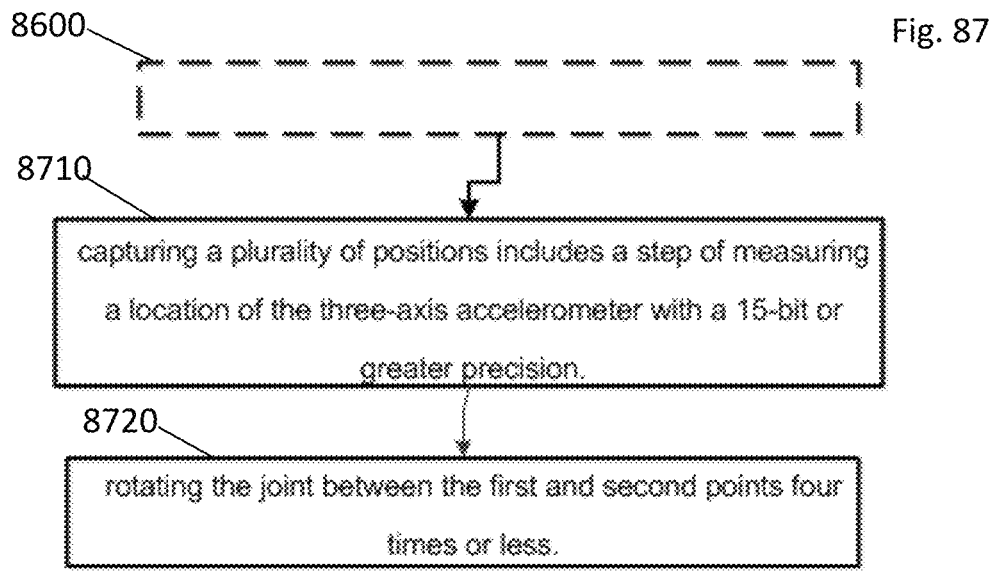
FIG. 87 illustrates another method of measuring tilt of a prepared bone surface of a muscular-skeletal joint.
Figure 88:
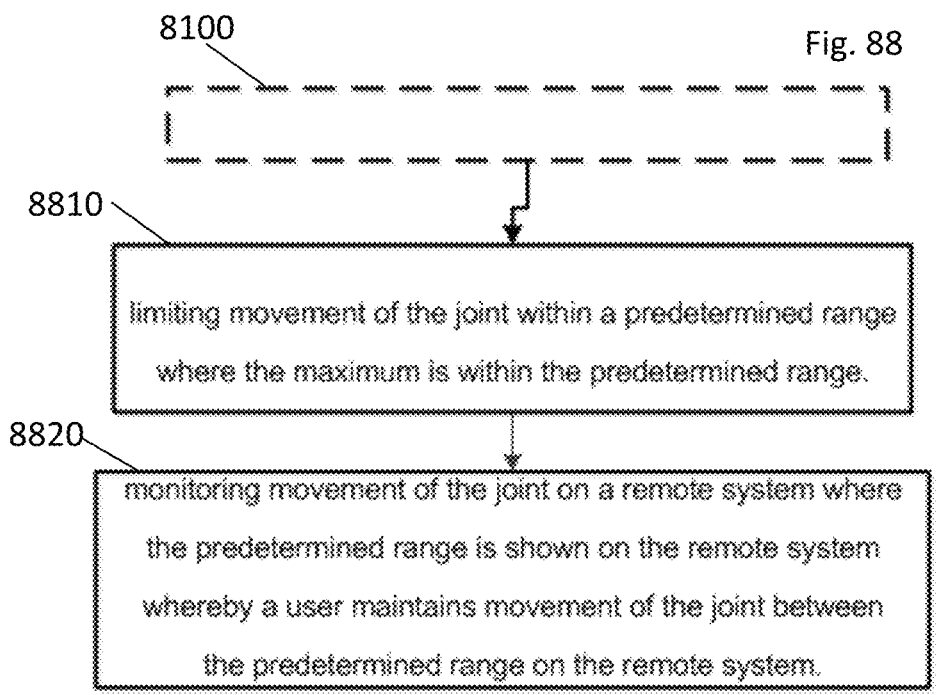
FIG. 88 illustrates another method of measuring tilt of a prepared bone surface of a muscular-skeletal joint.

Additional embodiments 8600, as illustrated in FIG. 86, include the steps of: capturing 8610 a plurality of positions of the three-axis accelerometer as the knee joint is moved between a first point to a second point; storing 8620 the plurality of positions of the three-axis accelerometer with each movement from the first point and the second point and from the second point to the first point; and calculating 8630 maximum and the position of the maximum. In additional embodiments, as illustrated in FIG. 87, the step of capturing 8710 a plurality of positions includes a step of measuring a location of the three-axis accelerometer with a 15-bit or greater precision. Additional embodiments include the step of: rotating 8720 the joint between the first and second points four times or less. Additional embodiments, illustrated in FIG. 88, include the step of: limiting 8810 movement of the joint within a predetermined range where the maximum is within the predetermined range. Additional embodiments include the steps of: monitoring 8820 movement of the joint on a remote system where the predetermined range is shown on the remote system whereby a user maintains movement of the joint between the predetermined range on the remote system.

Figure 89:
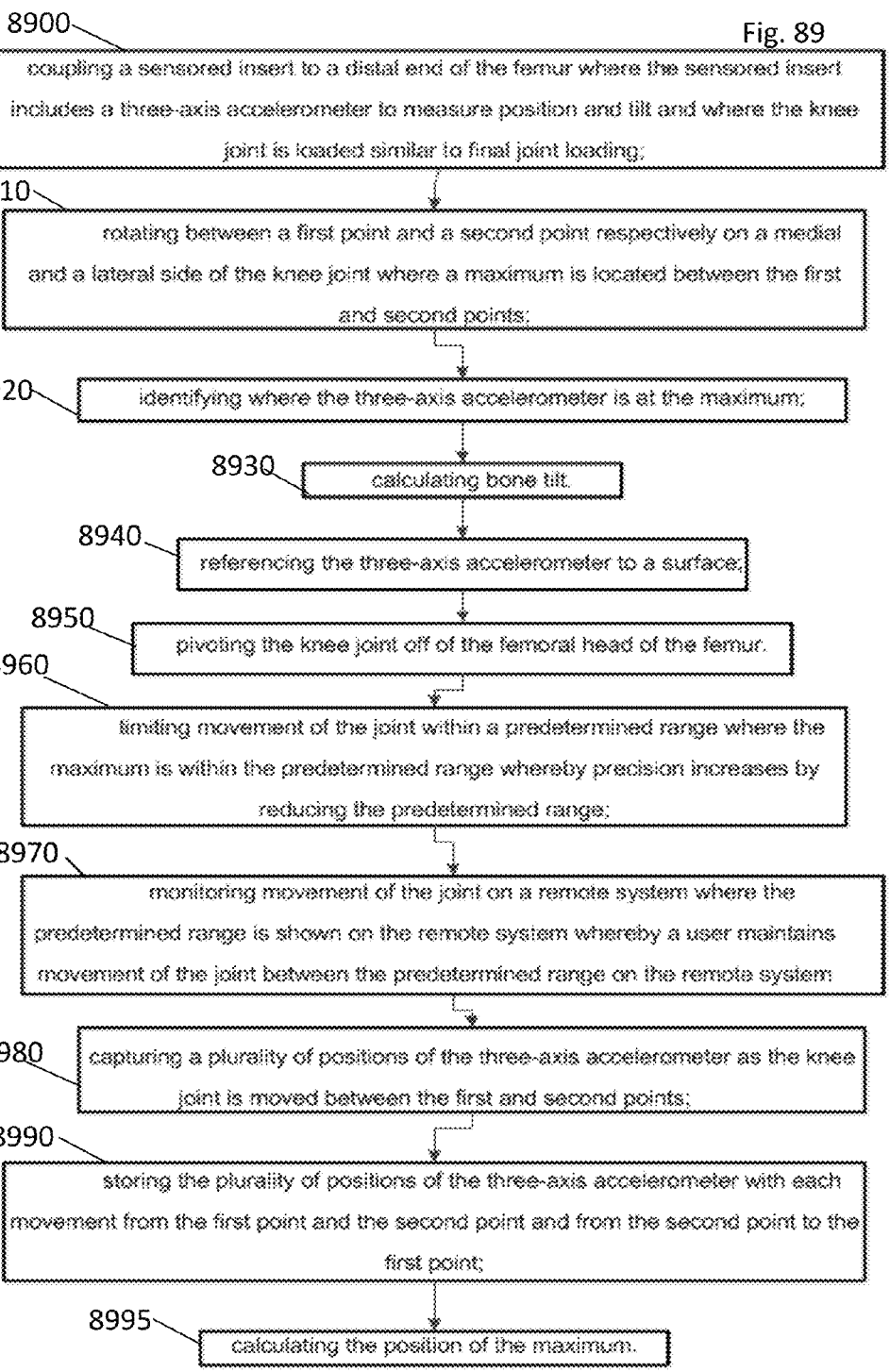
FIG. 89 illustrates a method of measuring medial-lateral tilt of a distal end of a femur of a knee joint.

At least one embodiment, as illustrated in FIG. 89, is directed to a method of measuring medial-lateral tilt of a distal end of a femur of a knee joint comprising the steps of: coupling 8900 a sensored insert to a distal end of the femur where the sensored insert includes a three-axis accelerometer to measure position and tilt and where the knee joint is loaded similar to final joint loading; rotating 8910 between a first point and a second point respectively on a medial and a lateral side of the knee joint where a maximum is located between the first and second points; identifying 8920 where the three-axis accelerometer is at the maximum; and calculating 8930 bone tilt.

Additional embodiments include the steps of: referencing 8940 the three-axis accelerometer to a surface; and pivoting 8950 the knee joint off of the femoral head of the femur. Additional embodiments include the steps of: limiting 8960 movement of the joint within a predetermined range where the maximum is within the predetermined range whereby precision increases by reducing the predetermined range; monitoring 8970 movement of the joint on a remote system where the predetermined range is shown on the remote system whereby a user maintains movement of the joint between the predetermined range on the remote system; capturing 8980 a plurality of positions of the three-axis accelerometer as the knee joint is moved between the first and second points; storing 8990 the plurality of positions of the three-axis accelerometer with each movement from the first point and the second point and from the second point to the first point; and calculating 8995 the position of the maximum.

At least one embodiment is directed to system to support kinetic assessment, joint modification, and installation of a final prosthetic joint comprising: a sensing insert configured to measure load, position of load, and joint alignment; a remote system coupled to the sensing insert configured to receive measurement data from the sensing insert where a joint assessment and subsequent changes to affect load, position of load, and joint alignment are performed under muscular-skeletal loading whereby a final joint installation has similar loading, position of load, and alignment.

Additional embodiments include: at least one articular surface; a plurality of load sensors underlying the articular surface configured to measure load and position of load; and a three axis accelerometer configured to referenced to a table or an acceleration value where the three axis accelerometer is configured to measure tilt and location. In at least one embodiment the remote system is configured to monitor position of load on a display and where a correction comprising one of rotating a prosthetic component or soft tissue tensioning can be performed under muscular-skeletal loading to move position of load on the at least one articular surface within a predetermined area range.

In at least one embodiment the sensing insert is configured to measure an offset of a first bone of the joint relative to a mechanical axis and where the three-axis accelerometer is configured to provide measurement data to determine the offset of the first bone. In at least one embodiment the sensing insert is configured to measure an offset of a second bone relative to a mechanical axis and where the three-axis accelerometer is configured to provide measurement data to determine the offset of the second bone. In at least one embodiment the system is configured to determine a total offset relative to a mechanical axis and if the total offset is within a predetermined offset range.

In at least one embodiment the sensored insert is configured to be referenced to a first plane, where the sensored insert is configured to be referenced to a second plane that is perpendicular to the first plane and where the first plane corresponds to a zero orientation in that plane or a zeroed acceleration with respect to that plane.

Figure 68:
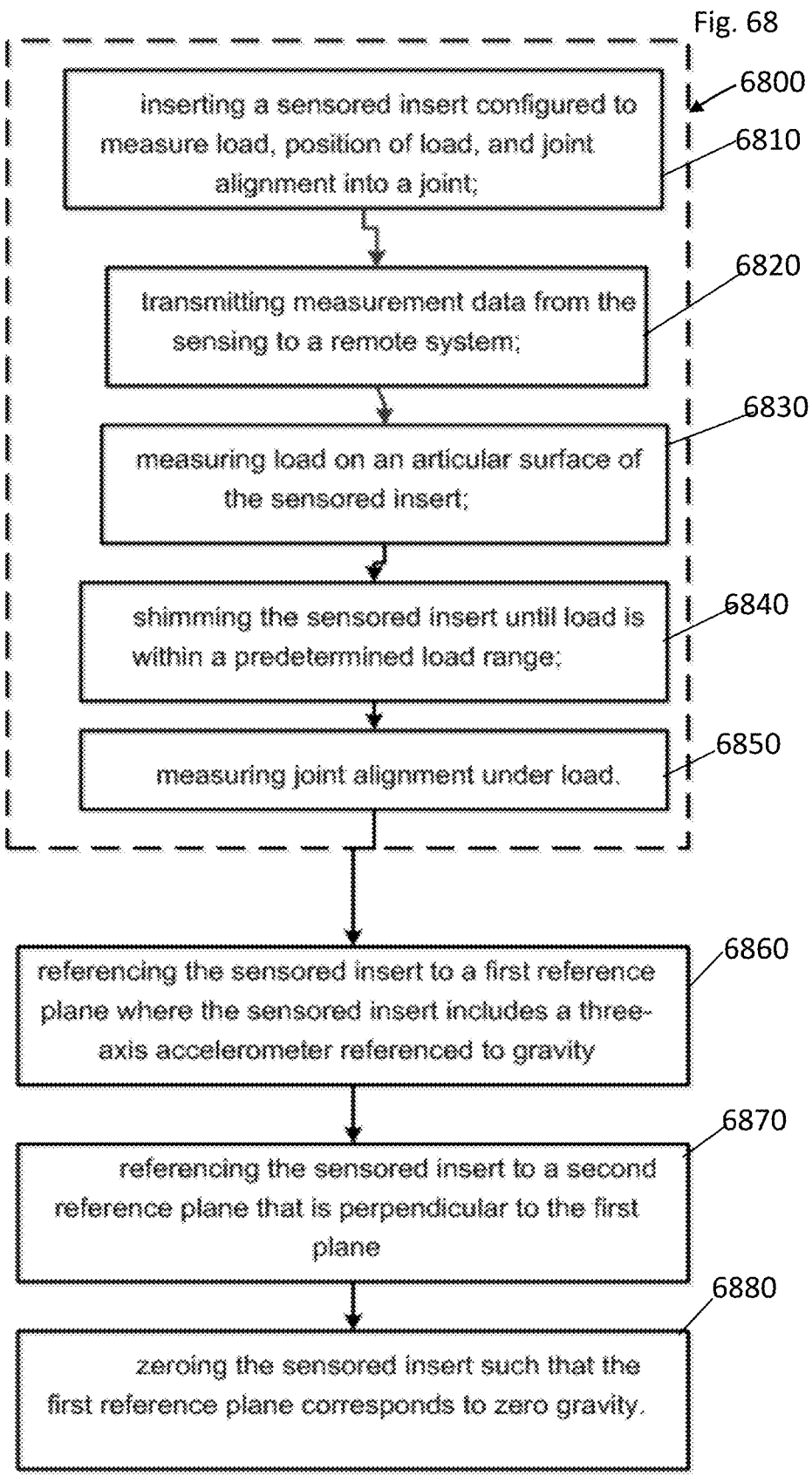
FIG. 68 illustrates a method of kinetic assessment, joint modification, and installation of a final prosthetic joint.

At least one embodiment 6800, as illustrated in FIG. 68, is directed to a method of kinetic assessment, joint modification, and installation of a final prosthetic joint comprising: inserting a sensored insert 6810 configured to measure load, position of load, and joint alignment into a joint; transmitting measurement data 6820 from the sensing to a remote system; measuring load 6830 on an articular surface of the sensored insert; and shimming 6840 the sensored insert until load is within a predetermined load range; and measuring 6850 joint alignment under load.

At least one embodiment further includes the steps of: referencing 6860 the sensored insert to a first reference plane where the sensored insert includes a three-axis accelerometer referenced to gravity; referencing 6870 the sensored insert to a second reference plane that is perpendicular to the first plane; and zeroing 6880 the sensored insert such that the first reference plane corresponds to zero gravity.

Figure 69:
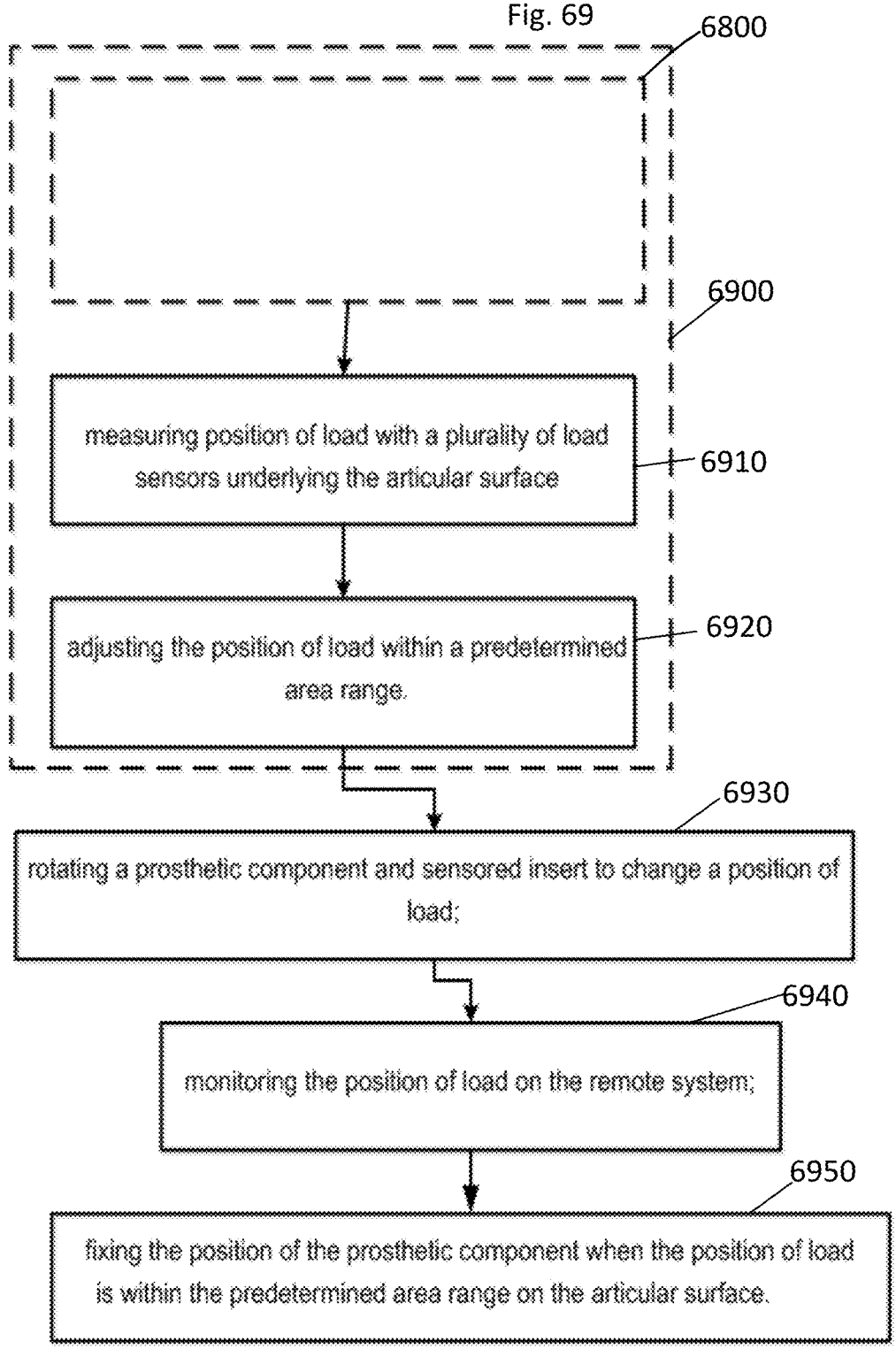
FIG. 69 illustrates a method of kinetic assessment, joint modification, and installation of a final prosthetic joint.

At least one embodiment 6900, illustrating FIG. 69, further includes the steps of: measuring 6910 position of load with a plurality of load sensors underlying the articular surface; and adjusting 6920 the position of load within a predetermined area range. At least one embodiment further includes the steps of: rotating 6930 a prosthetic component and sensored insert to change a position of load; monitoring 6940 the position of load on the remote system; and fixing 6950 the position of the prosthetic component when the position of load is within the predetermined area range on the articular surface.

At least one embodiment, as illustrated in FIG. 70, further includes a step of performing a step of soft tissue tensioning 7010 to change the load applied to the articular surface or to change a position of load applied to the articular surface. At least one embodiment, as illustrated in FIG. 71, further includes a step of measuring 7110 bone slope of a prepared bone surface. At least one embodiment further includes a step of modifying 7120 the prepared bone surface to be within a predetermined slope range. At least one embodiment further includes the steps of: measuring 7130 anterior-posterior slope of the prepared bone surface; and measuring 7140 the medial-lateral slope of the prepared bone surface.

At least one embodiment, as illustrated in FIG. 72, further includes the steps of: measuring 7210 an offset of a first bone of the joint relative to the mechanical axis where the three-axis accelerometer is configured to provide measurement data to determine the offset of the first bone; and measuring 7220 an offset of a second bone of the joint relative to a mechanical axis and where the three-axis accelerometer is configured to provide measurement data to determine the offset of the second bone.

At least one embodiment further includes adjusting joint alignment 7230 within a predetermined alignment range where a joint assessment and subsequent changes to affect load, position of load, and joint alignment are performed under muscular-skeletal loading whereby a final joint installation has similar loading, position of load, and alignment.

Figure 73:
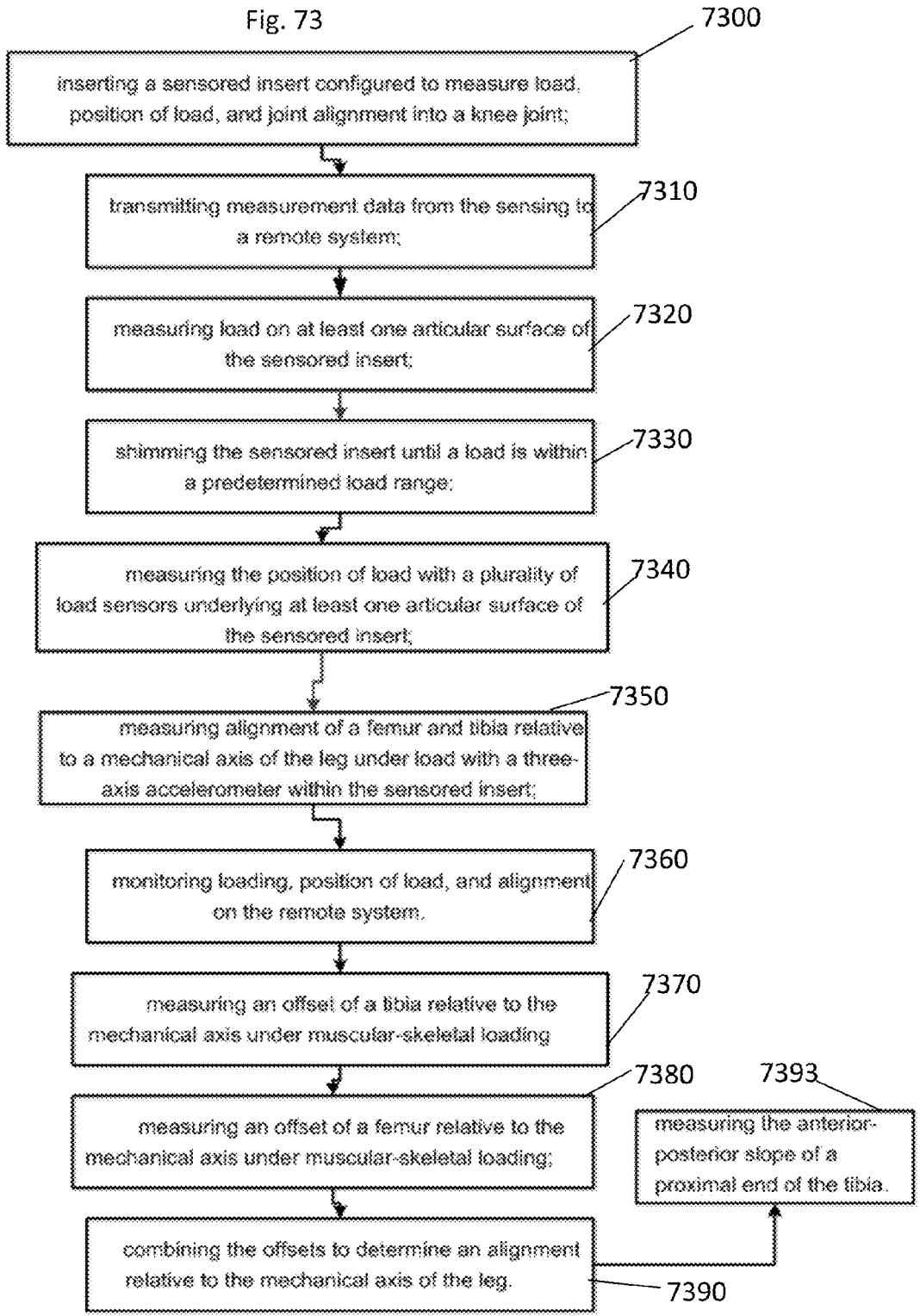
FIG. 73 illustrates a method of kinetic knee assessment for installing a prosthetic knee joint.

At least one embodiment, as illustrated in FIG. 73, is directed to a method of kinetic knee assessment for installing a prosthetic knee joint comprising: inserting 7300 a sensored insert configured to measure load, position of load, and joint alignment into a knee joint; transmitting 7310 measurement data from the sensing to a remote system; measuring 7320 load on at least one articular surface of the sensored insert; and shimming 7330 the sensored insert until a load is within a predetermined load range; measuring 7340 the position of load with a plurality of load sensors underlying at least one articular surface of the sensored insert; measuring 7350 alignment of a femur and tibia relative to a mechanical axis of the leg under load with a three-axis accelerometer within the sensored insert; and monitoring 7360 loading, position of load, and alignment on the remote system.

At least one embodiment further includes the steps of: measuring 7370 an offset of a tibia relative to the mechanical axis under muscular-skeletal loading; measuring 7380 an offset of a femur relative to the mechanical axis under muscular-skeletal loading; and combining 7390 the offsets to determine an alignment relative to the mechanical axis of the leg. At least one embodiment further includes a step of measuring 7393 the anterior-posterior slope of a proximal end of the tibia.

At least one further embodiment is directed to measuring and/or displaying contact information. The contact information can be useful since the prosthetic component can be rotated to change the position of load. Therefore the amount of rotation can be recorded, displayed and used. In at least one embodiment the contact information is recorded. Note that contact information can affect subsequent measurements.

Figure 74:
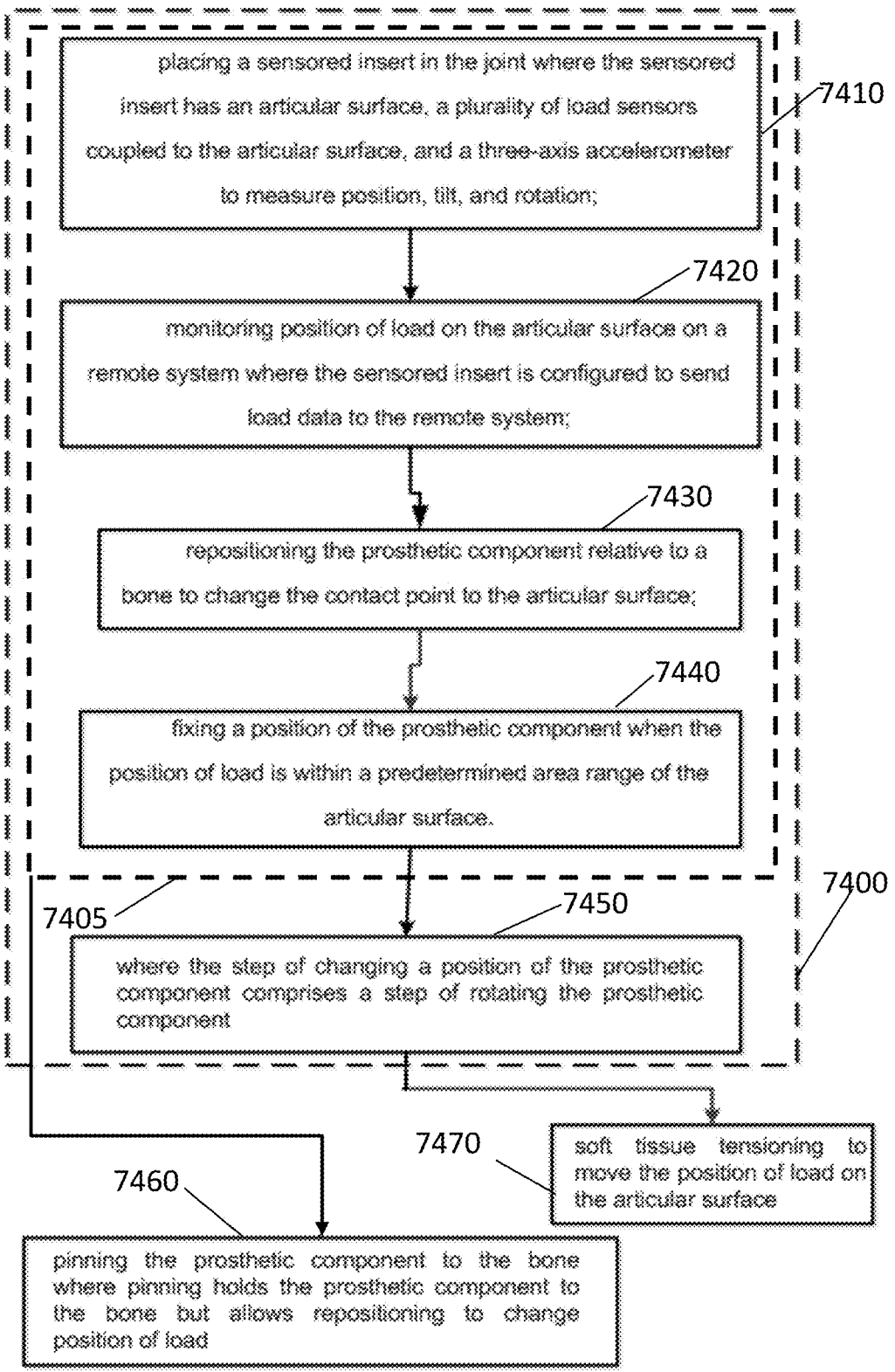
FIG. 74 illustrates a method of adjusting a contact point of a joint system where a prosthetic component is coupled to a bone.

For example at least one embodiment, as illustrating in FIG. 74, is directed to a method 7405 of adjusting a contact point of a joint system where a prosthetic component is coupled to a bone comprising the steps of: placing a sensored insert 7410 in the joint where the sensored insert has an articular surface, a plurality of load sensors coupled to the articular surface, and a three-axis accelerometer to measure position, tilt, and rotation; monitoring 7420 position of load on the articular surface on a remote system where the sensored insert is configured to send load data to the remote system; repositioning 7430 the prosthetic component relative to a bone to change the contact point to the articular surface; and fixing a position 7440 of the prosthetic component when the position of load is within a predetermined area range of the articular surface.

At least one embodiment further includes the step 7450 of changing a position of the prosthetic component. At least one embodiment further includes a step of rotating the prosthetic component. At least one embodiment further includes a step of soft tissue tensioning 7470 to move the position of load on the articular surface. At least one embodiment further includes a step of pinning 7460 the prosthetic component to the bone where pinning holds the prosthetic component to the bone but allows repositioning to change position of load.

Figure 75:
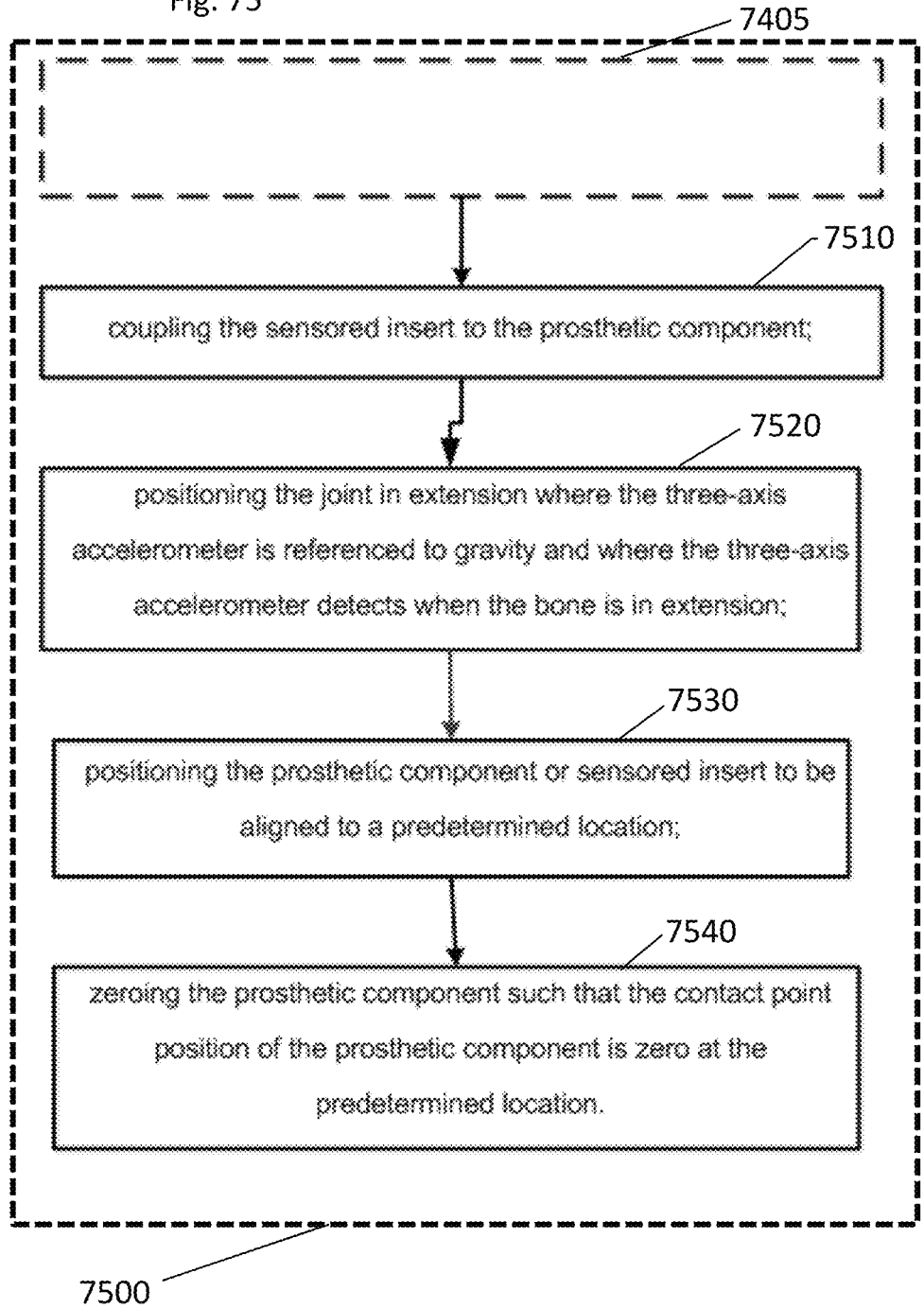
FIG. 75 illustrates another method of adjusting a contact point of a joint system where a prosthetic component is coupled to a bone.

At least one embodiment 7500, as illustrated in FIG. 75, further includes the steps of: coupling 7510 the sensored insert to the prosthetic component; positioning 7520 the joint in extension where the three-axis accelerometer is referenced to gravity and where the three-axis accelerometer detects when the bone is in extension; positioning 7530 the prosthetic component or sensored insert to be aligned to a predetermined location; and zeroing 7540 the prosthetic component such that the contact point position of the prosthetic component is zero at the predetermined location.

Figure 76:
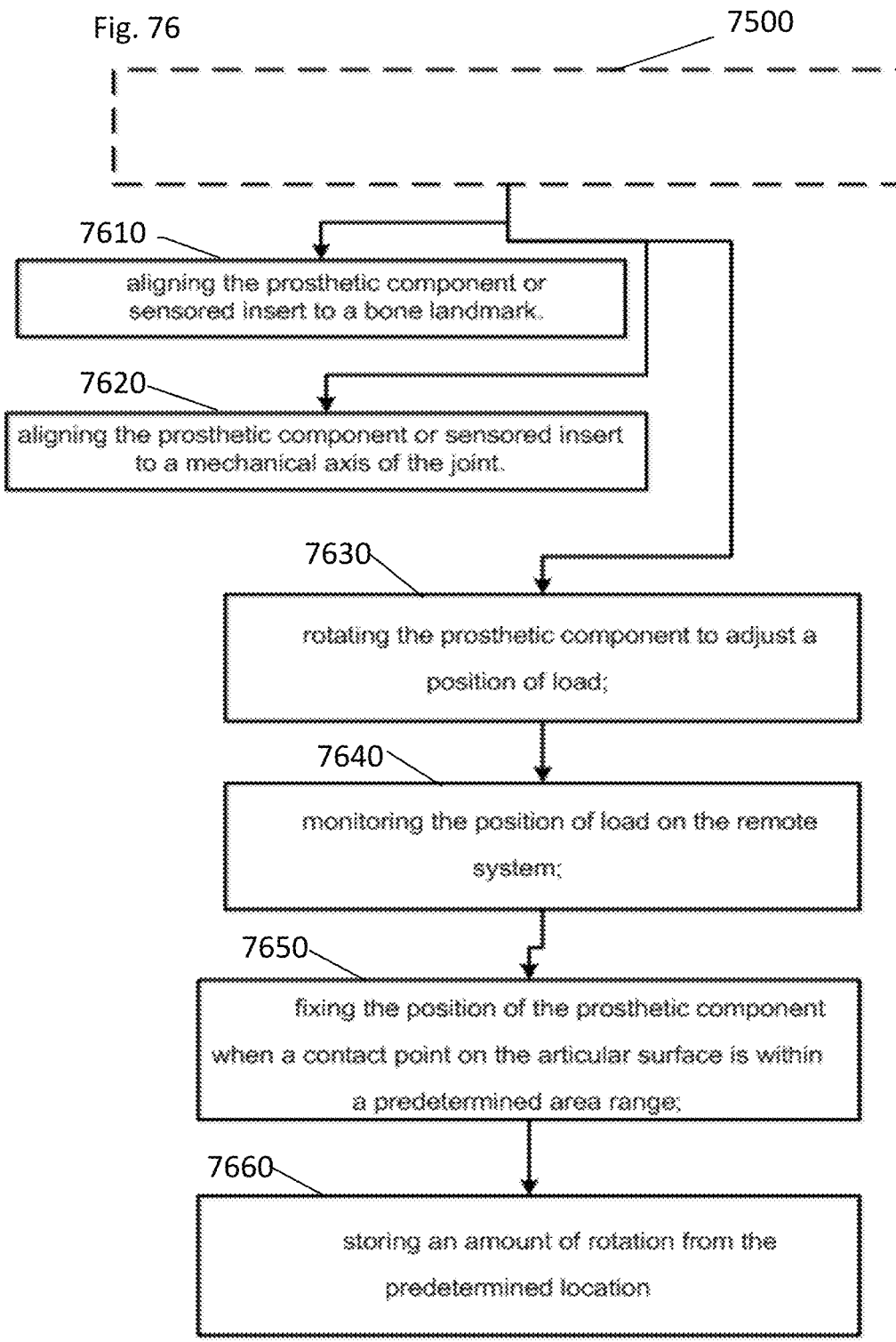
FIG. 76 illustrates another method of adjusting a contact point of a joint system where a prosthetic component is coupled to a bone.

At least one embodiment, as illustrated in FIG. 76, further includes a step of aligning 7610 the prosthetic component or sensored insert to a bone landmark. At least one embodiment further includes a step of aligning 7620 the prosthetic component or sensored insert to a mechanical axis of the joint. At least one embodiment further includes the steps of: rotating 7630 the prosthetic component to adjust a position of load; monitoring 7640 the position of load on the remote system; fixing 7650 the position of the prosthetic component when a contact point on the articular surface is within a predetermined area range; and storing 7660 an amount of rotation from the predetermined location.

Figure 77:
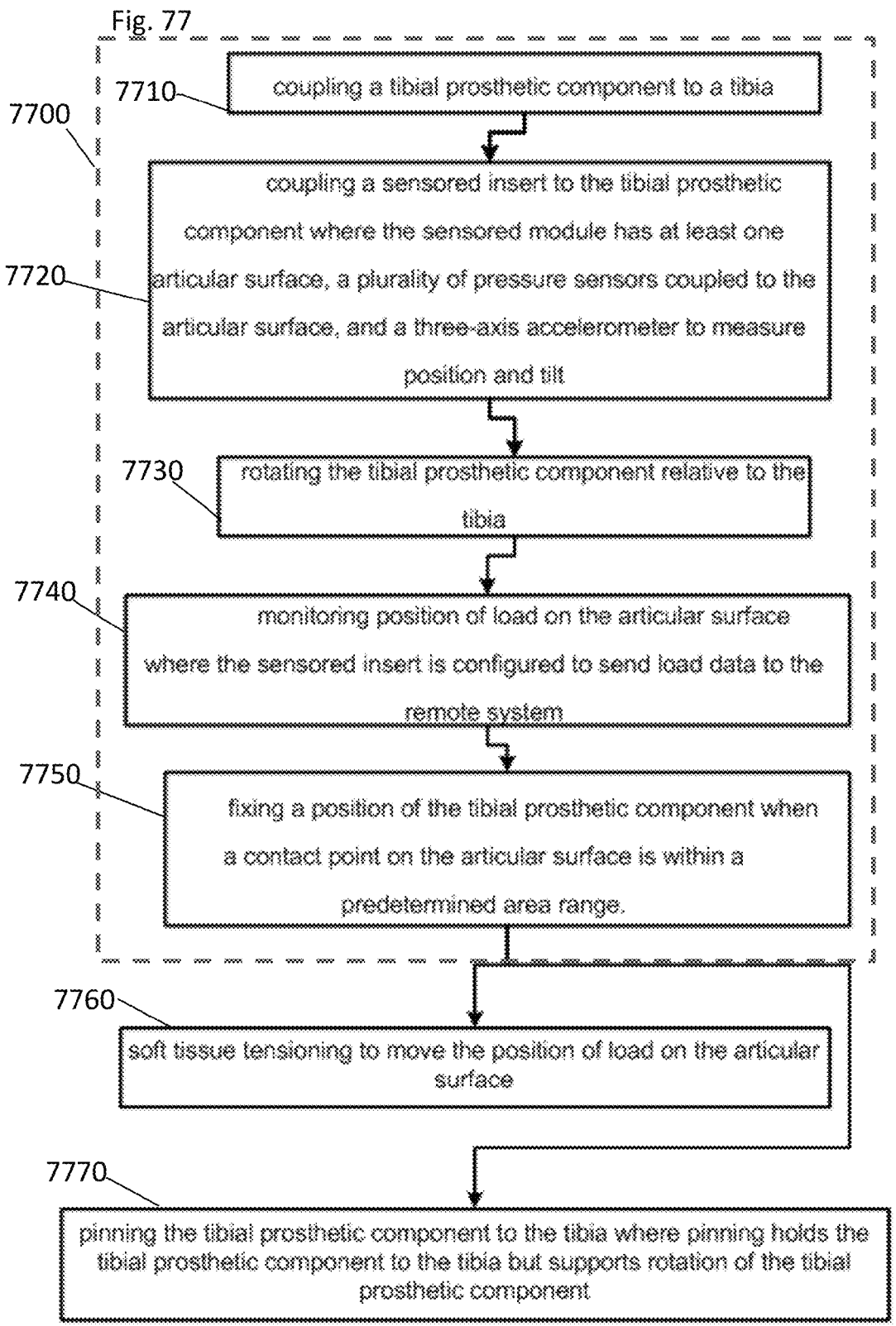
FIG. 77 illustrates a method of adjusting a tibial prosthetic component in a knee joint.

At least one embodiment 7700, as illustrated in FIG. 77, is directed to a method of adjusting a tibial prosthetic component in a knee joint comprising the steps of: coupling 7710 a tibial prosthetic component to a tibia; coupling 7720 a sensored insert to the tibial prosthetic component where the sensored module has at least one articular surface, a plurality of pressure sensors coupled to the articular surface, and a three-axis accelerometer to measure position and tilt; rotating 7730 the tibial prosthetic component relative to the tibia; monitoring 7740 position of load on the articular surface where the sensored insert is configured to send load data to the remote system; and fixing 7750 a position of the tibial prosthetic component when a contact point on the articular surface is within a predetermined area range.

At least one embodiment further includes a step of soft tissue tensioning 7760 to move the position of load on the articular surface. At least one embodiment further includes a step of pinning 7770 the tibial prosthetic component to the tibia where pinning holds the tibial prosthetic component to the tibia but supports rotation of the tibial prosthetic component.

Figure 78:
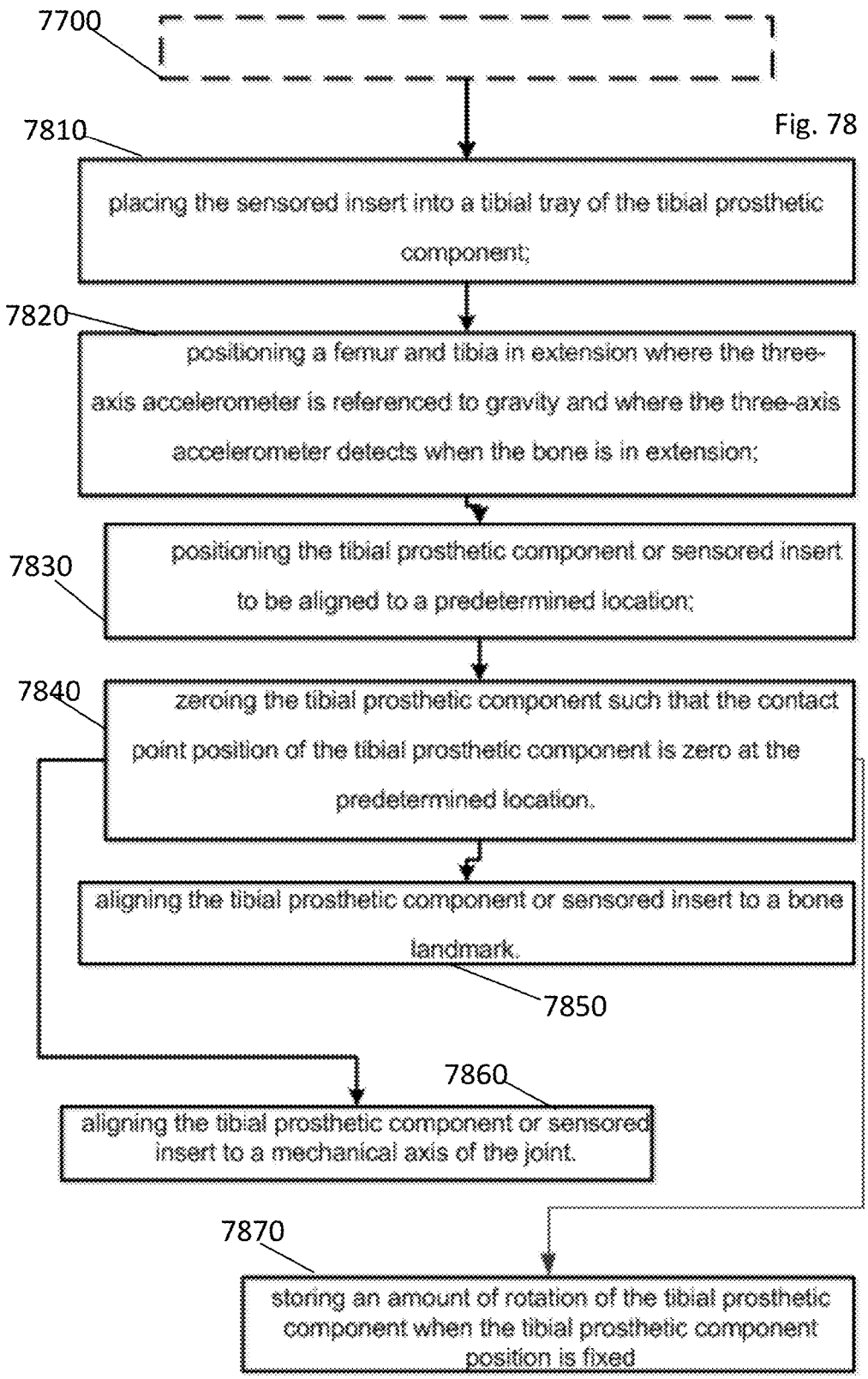
FIG. 78 illustrates another method of adjusting a tibial prosthetic component in a knee joint.

At least one embodiment, as illustrated in FIG. 78, further includes the steps of: placing 7810 the sensored insert into a tibial tray of the tibial prosthetic component; positioning 7820 a femur and tibia in extension where the three-axis accelerometer is referenced to gravity and where the three-axis accelerometer detects when the bone is in extension; positioning 7830 the tibial prosthetic component or sensored insert to be aligned to a predetermined location; and zeroing 7840 the tibial prosthetic component such that the contact point position of the tibial prosthetic component is about zero at the predetermined location.

At least one embodiment further includes a step of aligning 7850 the tibial prosthetic component or sensored insert to a bone landmark. At least one embodiment further includes a step of aligning 7860 the tibial prosthetic component or sensored insert to a mechanical axis of the joint.

At least one embodiment further includes a step of storing 7870 an amount of rotation of the tibial prosthetic component when the tibial prosthetic component position is fixed.

Figure 79:
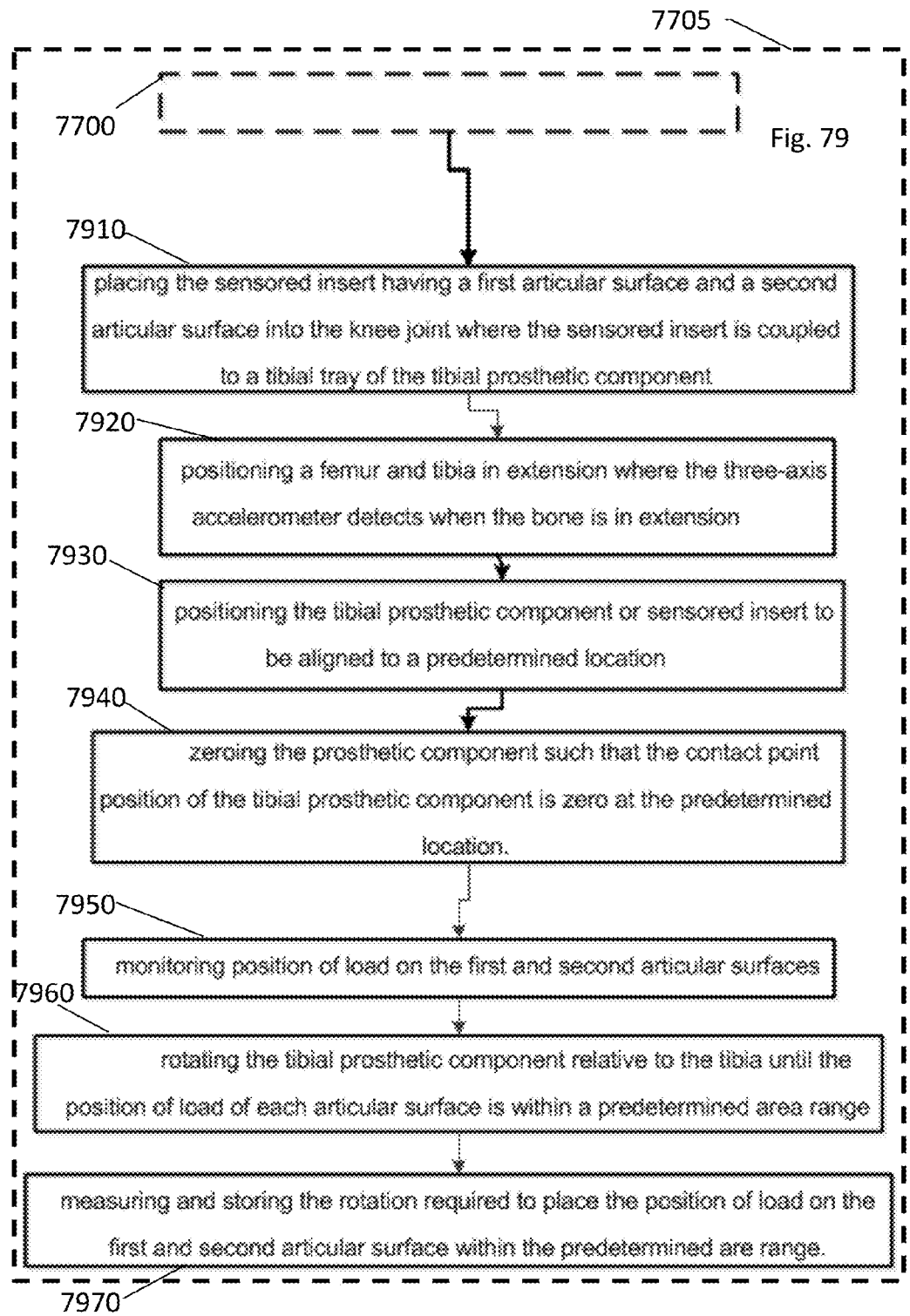
FIG. 79 illustrates another method of adjusting a tibial prosthetic component in a knee joint.

At least one embodiment 7705, as illustrated in FIG. 79, further includes the steps of: placing 7910 the sensored insert having a first articular surface and a second articular surface into the knee joint where the sensored insert is coupled to a tibial tray of the tibial prosthetic component; positioning 7920 a femur and tibia in extension where the three-axis accelerometer detects when the bone is in extension; positioning 7930 the tibial prosthetic component or sensored insert to be aligned to a predetermined location; and zeroing 7940 the prosthetic component such that the contact point position of the tibial prosthetic component is zero at the predetermined location.

At least one embodiment further includes the steps of: monitoring 7950 position of load on the first and second articular surfaces; and rotating 7960 the tibial prosthetic component relative to the tibia until the position of load of each articular surface is within a predetermined area range; and measuring 7970 and storing the rotation required to place the position of load on the first and second articular surface within the predetermined are range.

Figure 80:
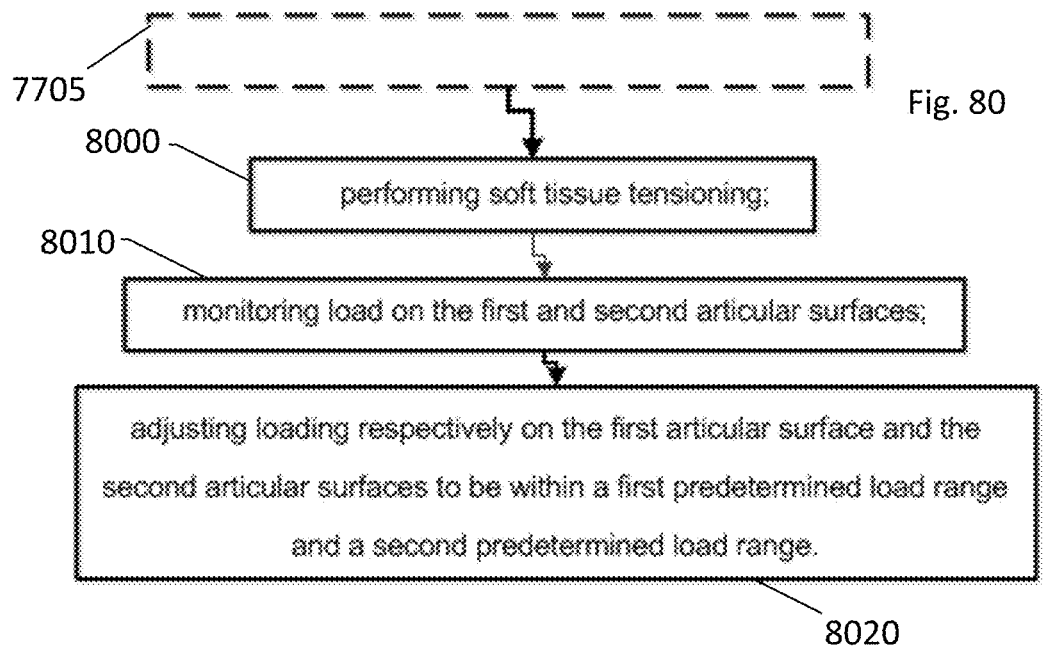
FIG. 80 illustrates another method of adjusting a tibial prosthetic component in a knee joint.

At least one embodiment, as illustrated in FIG. 80, further includes the steps of: performing soft tissue tensioning 8000; monitoring 8010 load on the first and second articular surfaces; and adjusting 8020 loading respectively on the first articular surface and the second articular surfaces to be within a first predetermined load range and a second predetermined load range.

At least one embodiment is directed to a system for adjusting contact position of a muscular-skeletal joint comprising: a prosthetic component configured to rotate after being coupled to a bone; a sensored insert having an articular surface where the sensored insert is configured to couple to the prosthetic component, where the sensored insert has a plurality of pressure sensors coupled to the articular surface and a three-axis accelerometer to measure position and tilt, and where the three-axis accelerometer is referenced to gravity; a remote system configured to wirelessly receive position of load data from the sensored insert where the remote system is configured to display the articular surface, where the remote system is configured to display position of applied load to the articular surface, and where the remote system is configured to store a zero contact point where the bone and prosthetic component are aligned.

In at least one embodiment the remote system is configured to display a predetermined area range on the articular surface, where the remote system is configured to indicate positions of flexion of the bone, where the remote system is configured to store an amount of rotation of the prosthetic component relative to the zero contact point where rotating the prosthetic component changes a position of applied load to the articular surface.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A method of measuring alignment to a mechanical axis of a muscular-skeletal system comprising the steps of:
   moving a joint through a first movement wherein a single tracking device is coupled to the joint, wherein the joint is moved between a first point and a second wherein the first movement pivots from a first pivot point, wherein a reference position of the joint is approximately centered between the first point and the second point, wherein the first point is 45 degrees or less from the reference position, and wherein the second point is 45 degrees or less from the reference position;
   sending tracking measurement data to a computer wherein a joint position is tracked and wherein the tracking measurement data comprises a plurality of position measurements throughout the first movement;
   moving the joint through a second movement;
   sending tracking measurement data to the computer wherein a joint position is tracked and wherein the tracking measurement data comprises a plurality of position measurements from throughout the second movement; and
   calculating alignment relative to a mechanical axis wherein the computer uses the tracking measurement data from the first and second movements to calculate alignment wherein the first movement measures a varus or valgus number relative to the mechanical axis of the first bone and wherein the second movement measures a varus or valgus number of the second bone relative to the mechanical axis; and
   subtracting the varus or valgus number of the second bone from the varus or valgus number of the first bone to calculate the alignment of the first and second bones to the mechanical axis.

2. The method of claim 1 further including a step of rotating the joint between the first point and the second point wherein the joint moves in an arc.

3. The method of claim 1 further including moving the joint through the second movement wherein the single tracking device is coupled to the joint, wherein the joint is moved between a third point and a fourth point and wherein the second movement pivots from a second pivot point.

4. The method of claim 1 further including a step of zeroing the tracking device to a first reference plane and a second reference plane.

5. The method of claim 1 further including a step of positioning the joint at approximately a 45 degree angle when pivoting on the first pivot point where the tracking device and electronic circuitry are housed in a prosthetic component of the joint.

6. The method of claim 1 further including the steps of:
   rotating the joint between the first and second points at least two times;
   measuring points of an arc generated as the joint is moved between the first and second points; and
   determining a maximum of the arc.

7. The method of claim 6 further including the steps of:
   calculating a tilt value of a bone cut of a first bone wherein the tracking measurement data is used by the computer to calculate the tilt value;
   converting the tilt value to a varus or valgus number in relation to a mechanical axis the joint for the first bone wherein the computer calculates the varus or valgus number.

8. The method of claim 7 further including a step of positioning the joint wherein the tracking device is at approximately 45 degree angle to a plane of a surface when pivoting on the first pivot point and wherein the first pivot point couples to the surface.

9. The method of claim 8 further including the steps of:
   calculating a tilt value of a bone cut of a second bone wherein the tracking measurement data is used by the computer to calculate the tilt value;
   converting the tilt value to a varus or valgus number in relation to a mechanical axis of the joint for the second bone wherein the computer calculates the varus or valgus number.

10. The method of claim 9 further including a step of subtracting the varus or valgus number of the second bone from the varus or valgus number of the first bone to calculate the alignment of the first and second bones to the mechanical axis.

11. A method of measuring alignment to a mechanical axis of a muscular-skeletal system comprising the steps of:
    moving a joint through a first movement wherein a single tracking device is coupled to the joint, wherein the joint is moved between a first point and a second at least two times, wherein the first movement pivots from a first pivot point, wherein a reference position of the joint is approximately centered between the first point and the second point, wherein the first point is 45 degrees or less from the reference position, wherein the second point is 45 degrees or less from the reference position, wherein the joint is positioned such that the tracking device is at approximately a 45 degree angle to a plane of a surface when pivoting on the first pivot point, wherein the first pivot point couples to the surface;

measuring points of an arc generated as the joint is moved between the first and second points;

sending tracking measurement data to a computer wherein a joint position is tracked and wherein the tracking measurement data comprises a plurality of position measurements throughout the first movement;

determining a maximum of the arc;

moving the joint through a second movement;

sending tracking measurement data to the computer wherein a joint position is tracked and wherein the tracking measurement data comprises a plurality of position measurements from throughout the second movement;

calculating a tilt value of a bone cut of a first bone wherein the tracking measurement data is used by the computer to calculate the tilt value;

converting the tilt value to a varus or valgus number in relation to a mechanical axis the joint for the first bone wherein the computer calculates the varus or valgus number;

calculating a tilt value of a bone cut of a second bone wherein the tracking measurement data is used by the computer to calculate the tilt value;

converting the tilt value to a varus or valgus number in relation to a mechanical axis of the joint for the second bone wherein the computer calculates the varus or valgus number; and subtracting the varus or valgus number of the second bone from the varus or valgus number of the first bone to calculate the alignment of the first and second bones to the mechanical axis.

12. The method of claim 11 further including a step of rotating the joint between the first point and the second point wherein the joint moves in an arc.

13. The method of claim 11 further including moving the joint through the second movement wherein the single tracking device is coupled to the joint, wherein the joint is moved between a third point and a fourth point and wherein the second movement pivots from a second pivot point.

14. The method of claim 11 further including a step of zeroing the tracking device to a first reference plane and a second reference plane.

15. The method of claim 11 further including a step of positioning the joint at approximately a 45 degree angle when pivoting on the first pivot point where the tracking device and electronic circuitry are housed in a prosthetic component of the joint.

* * * * *